(12) United States Patent
Moore et al.

(10) Patent No.: US 7,947,469 B2
(45) Date of Patent: May 24, 2011

(54) MODULATION OF HIV INFECTION

(75) Inventors: Michael Moore, Amersham (GB); Mark Isalan, London (GB); Lindsey Reynolds, Stevenage (GB); Christopher Ullman, Maidstone (GB); John Girdlestone, Cambridge (GB); Christophe Demaison, London (GB); Yen Choo, London (GB)

(73) Assignee: Gendaq, Ltd., London (GB)

( * ) Notice: Subject to any disclaimer, the term of this patent is extended or adjusted under 35 U.S.C. 154(b) by 1458 days.

(21) Appl. No.: 10/470,065

(22) PCT Filed: Jan. 22, 2002

(86) PCT No.: PCT/GB02/00246

§ 371 (c)(1),
(2), (4) Date: Feb. 5, 2004

(87) PCT Pub. No.: WO02/057308

PCT Pub. Date: Jul. 25, 2002

(65) Prior Publication Data

US 2004/0110923 A1    Jun. 10, 2004

(30) Foreign Application Priority Data

Jan. 22, 2001 (GB) .................................. 0101576.7
Feb. 7, 2001 (GB) .................................. 0103032.9

(51) Int. Cl.
*C12P 21/04* (2006.01)
*C12P 21/06* (2006.01)
*C12Q 1/68* (2006.01)
*C12N 5/00* (2006.01)
*C07H 21/04* (2006.01)

(52) U.S. Cl. ......... 435/69.1; 435/6; 435/325; 536/23.5; 536/24.1

(58) Field of Classification Search .......................... None
See application file for complete search history.

(56) References Cited

U.S. PATENT DOCUMENTS

| 5,789,538 | A | 8/1998 | Rebar et al. |
|---|---|---|---|
| 6,007,988 | A | 12/1999 | Choo et al. |
| 6,013,453 | A | 1/2000 | Choo et al. |
| 6,140,081 | A | 10/2000 | Barbas |
| 6,140,466 | A | 10/2000 | Barbas, III et al. |
| 6,242,568 | B1 | 6/2001 | Barbas, III et al. |
| 6,453,242 | B1 | 9/2002 | Eisenberg et al. |
| 6,534,261 | B1 | 3/2003 | Cox, III et al. |
| 6,607,882 | B1 | 8/2003 | Cox, III et al. |
| 6,689,877 | B2 * | 2/2004 | Ikezu et al. .................. 536/23.5 |
| 7,067,317 | B2 | 6/2006 | Rebar et al. |
| 2002/0061512 | A1 * | 5/2002 | Kim et al. ........................ 435/4 |
| 2002/0165356 | A1 | 11/2002 | Barbas, III et al. |
| 2003/0082561 | A1 | 5/2003 | Sera |
| 2003/0134350 | A1 | 7/2003 | Sera |

FOREIGN PATENT DOCUMENTS

| WO | WO 96/06166 A1 | 2/1996 |
|---|---|---|
| WO | WO 96/32475 A2 | 10/1996 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 99/42474 A2 | 8/1999 |
| WO | WO 99/45132 A1 | 9/1999 |
| WO | WO 99/47656 A2 | 9/1999 |
| WO | WO 00/23464 A2 | 4/2000 |
| WO | WO 00/27878 A1 | 5/2000 |
| WO | WO 00/41566 A1 | 7/2000 |
| WO | WO 00/42219 A1 | 7/2000 |
| WO | WO 02/42459 A2 | 5/2002 |
| WO | WO 02/066640 A2 | 8/2002 |
| WO | WO 03/016496 A2 | 2/2003 |

OTHER PUBLICATIONS

Connor et al. 1997. J Exp Med. 185:621-628.*
Pohlman et al. 2006. Current Pharm Design. 12:1963-1973.*
Phillips, A. 2001 J Pharm Pharmacology 53: 1169-1174.*
Starr-Spires et al. 2002. Clin Lab Med 22:681-701.*
Thiesen, H. 1996. Gene Expression. 5:229-243.*
Romano 2003. Drug News Perspect. 16:267-276.*
Hosokawa et al. 2001. BBRC 283:563-568.*
Unutmaz et al. 1998. Seminars in Immunology.*
Hunt et al 2002. Science 297:415-416.*
U.S. Appl. No. 09/718,538, filed Nov. 22, 2000, Choo et al.
Sangamo BioSciences Signs Definitive Agreement to Acquire Gendaq Ltd., Richmond, CA, Jun. 28, 2001.
Sangamo BioSciences, Inc. Completes Gendaq Ltd. Acquisition, Richmond, CA, Jul. 5, 2001.
Dai, et al., "Engineered Zinc Finger-Activating Vascular Endothelial Growth Factor Transcription Factor Plasmid DNA Induces Therapeutic Angiogenesis in Rabbits With Hindlimb Ischemia," *Circulation* 110:2467-2475 (2004).
Price, et al., "Gene Transfer of an Engineered Transcription Factor Promoting Expression of VEGF-A Protects Against Experimental Diabetic Neuropathy," *Diabetes* 55:1847-1854 (2006).
Rebar, et al., "Induction of Angiogenesis in a Mouse Model Using Engineered Transcription Factors," *Nature Medicine* 8:1427-1432 (2002).

* cited by examiner

*Primary Examiner* — Shulamith H Shafer
(74) *Attorney, Agent, or Firm* — Dahna S. Pasternak; Robins & Pasternak LLP

(57) ABSTRACT

Disclosed herein are methods and compositions for modulating HIV infection by regulating expression of one or more receptors.

2 Claims, 13 Drawing Sheets

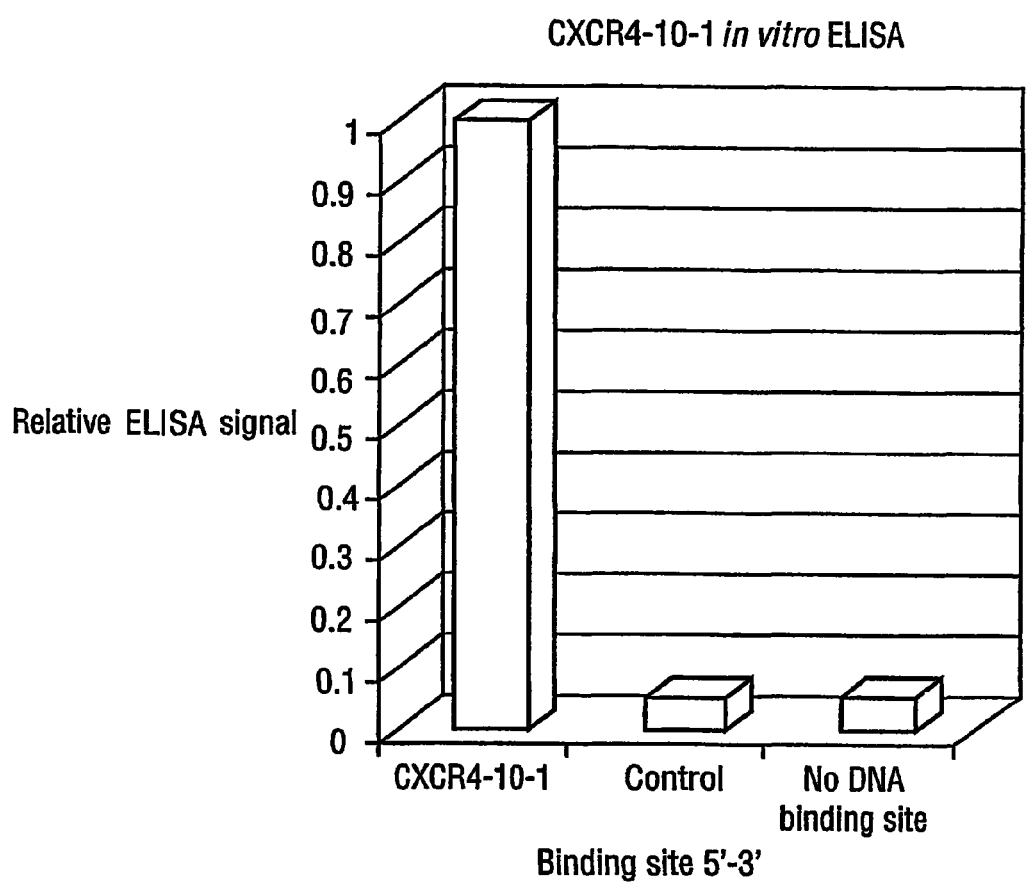

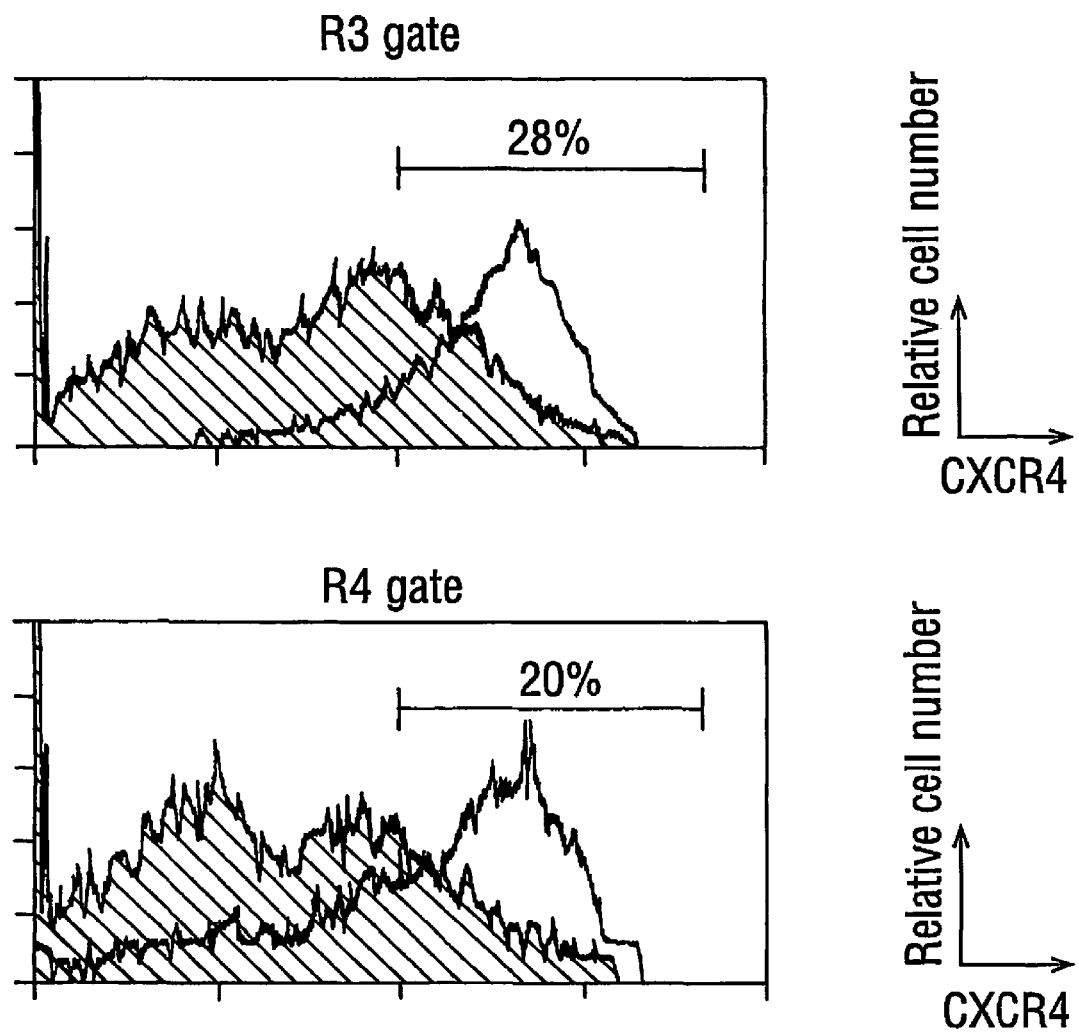
FIG. 2B(contd.)

TNFR1-4-2 in vitro ELISA

Sequences of binding sites used for TNFR1 ELISA

| | | |
|---|---|---|
| 4-2 | gtcgg(attggtgggttgggggca)caaggca | SEQ ID NO. 111 |
| 7-9 | tggag(gaggaggcc)a(caggaggcg)ggagga | SEQ ID NO. 112 |
| 9-12 | cagga(agagctgg)a(ggaggaggcc)acagga | SEQ ID NO. 113 |

TNFR1-7-9 in vitro ELISA

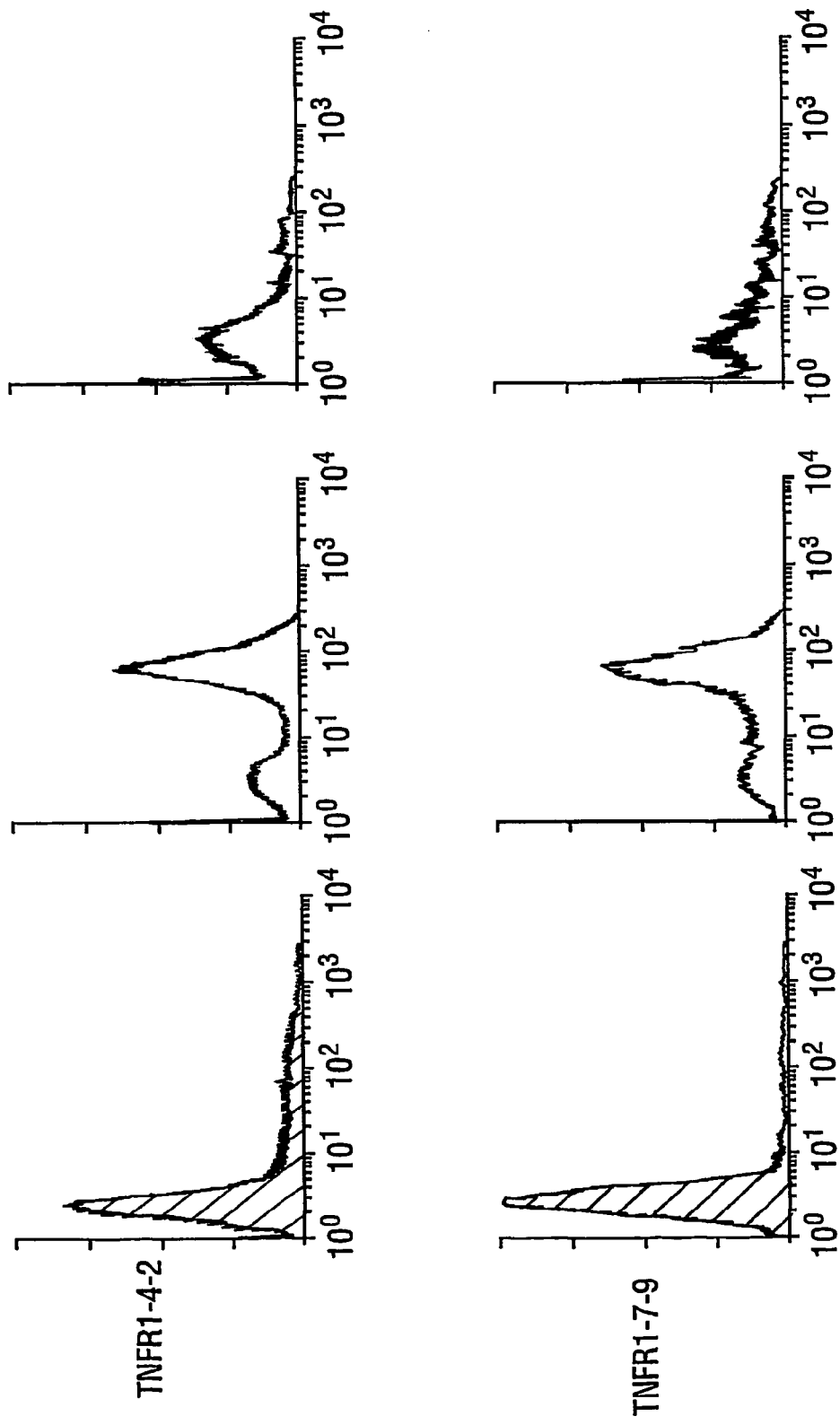
FIG. 4B(contd)

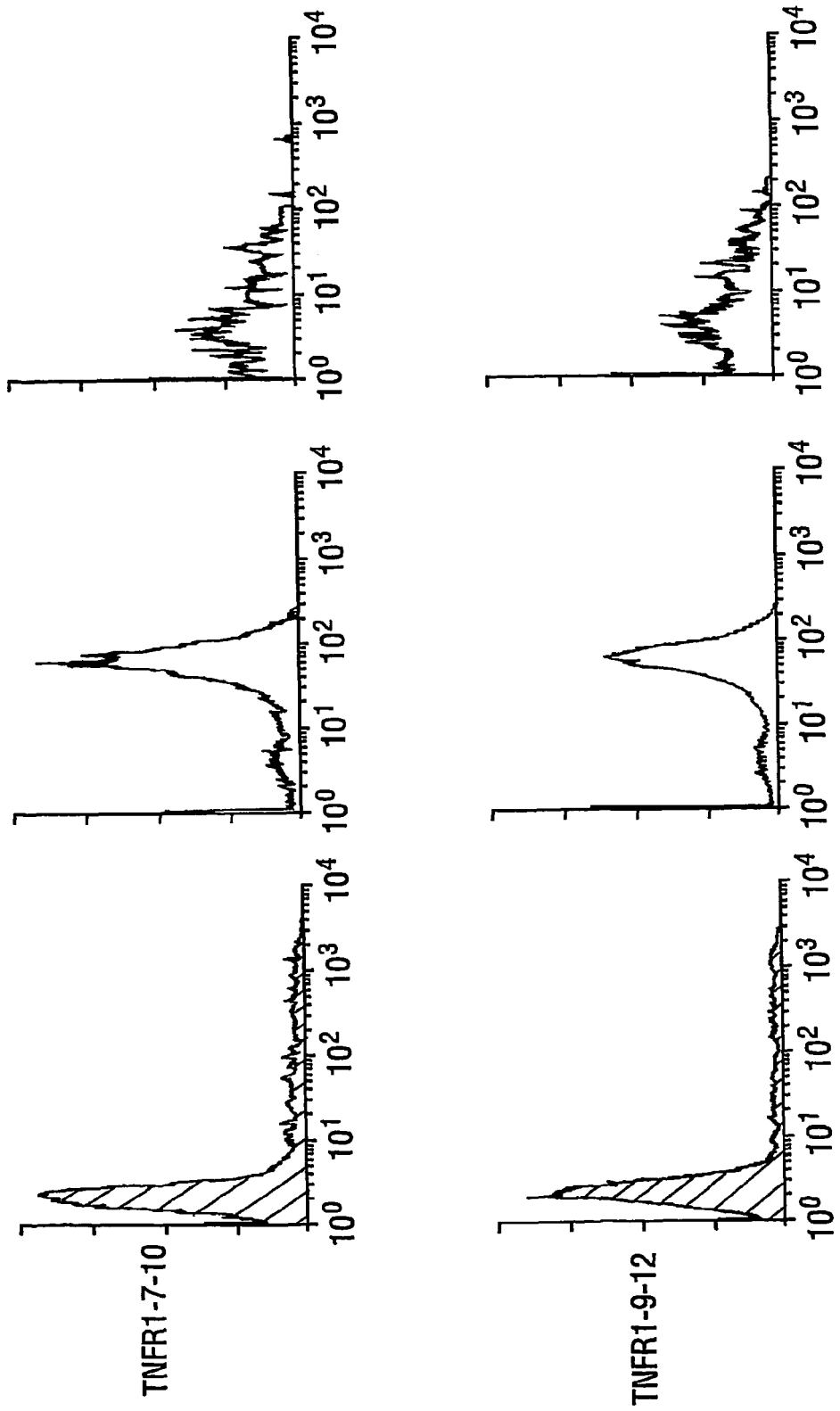
FIG. 4B(contd.)

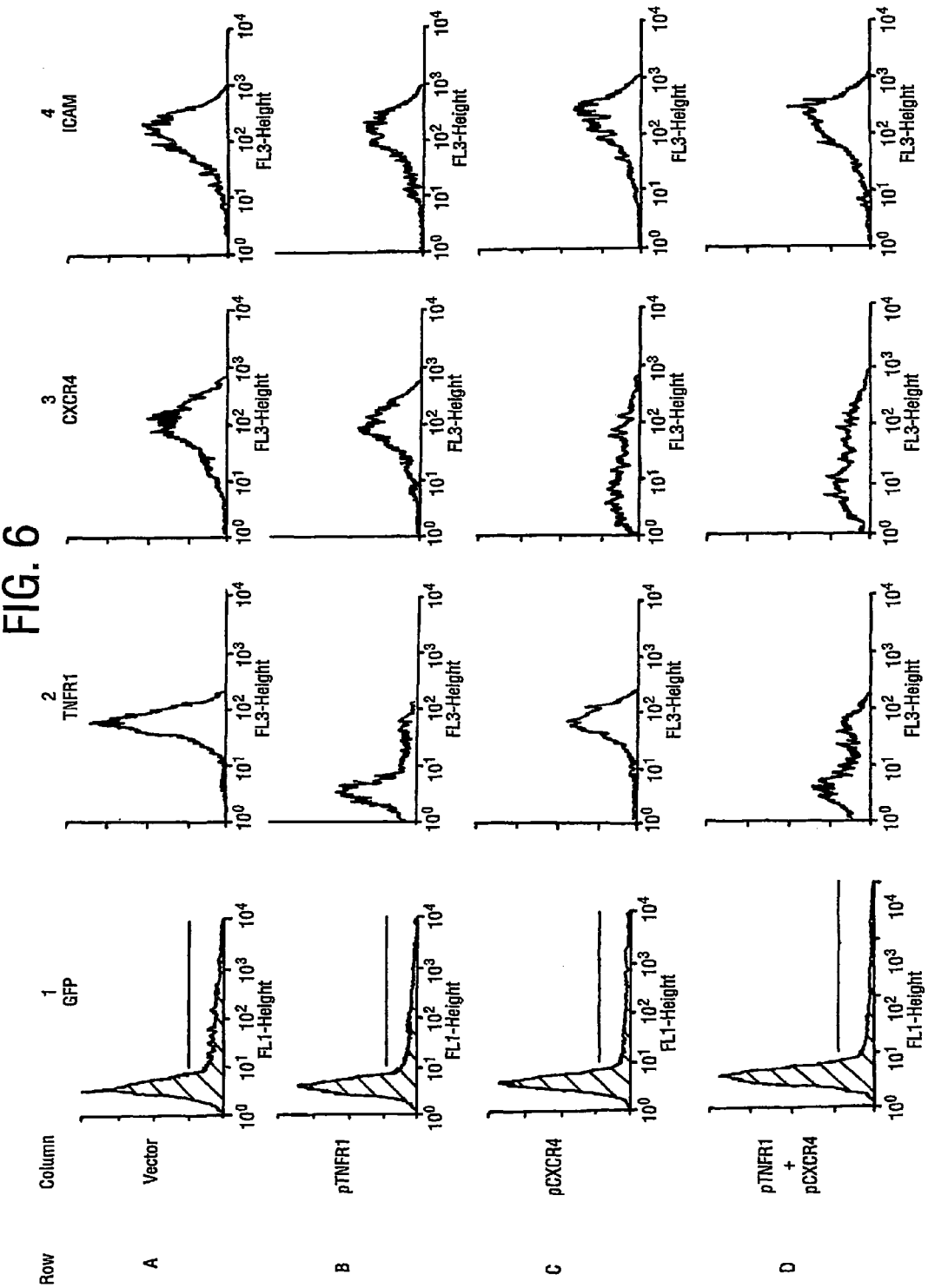

SEQUENCE LISTING

<160> NUMBER OF SEQ ID NOS: 123

<210> SEQ ID NO 1
<211> LENGTH: 4
<212> TYPE: PRT
<213> ORGANISM: Artificial
<220> FEATURE:
<223> OTHER INFORMATION: Flexible Linker Sequence

<400> SEQUENCE: 1

Gly Glu Arg Pro
1

<210> SEQ ID NO 2
<211> LENGTH: 14
<212> TYPE: PRT
<213> ORGANISM: Artificial
<220> FEATURE:
<223> OTHER INFORMATION: Flexible Linker Sequence

<400> SEQUENCE: 2

Gly Gly Gly Gly Ser Gly Gly Ser Gly Gly Ser Glu Arg Pro
1               5                   10

<210> SEQ ID NO 3
<211> LENGTH: 20
<212> TYPE: PRT
<213> ORGANISM: Artificial
<220> FEATURE:
<223> OTHER INFORMATION: Flexible Linker Sequence

<400> SEQUENCE: 3

Gly Gly Gly Gly Ser Gly Gly Ser Gly Gly Ser Gly Gly Ser Gly Gly
1               5                   10                  15

Ser Glu Arg Pro
            20

<210> SEQ ID NO 4
<211> LENGTH: 47
<212> TYPE: DNA
<213> ORGANISM: Homo sapiens

<400> SEQUENCE: 4
tccccgcccc agcggcgcat gcgccgcgct cggagcgtgt ttttata          47

<210> SEQ ID NO 5
<211> LENGTH: 38
<212> TYPE: DNA
<213> ORGANISM: Homo sapiens

<400> SEQUENCE: 5
ccgccccagc ggcgcatgcg ccgcgctcgg agcgtgtt                    38

<210> SEQ ID NO 6
<211> LENGTH: 38
<212> TYPE: DNA
<213> ORGANISM: Homo sapiens

<400> SEQUENCE: 6
ccgccccagc ggcgcatgcg ccgcgctcgg agcgtgtt                    38

<210> SEQ ID NO 7
<211> LENGTH: 38
<212> TYPE: DNA
<213> ORGANISM: Homo sapiens

<400> SEQUENCE: 7
ccgccccagc ggcgcatgcg ccgcgctcgg agcgtgtt                    38

<210> SEQ ID NO 8
<211> LENGTH: 30
<212> TYPE: DNA
<213> ORGANISM: Homo sapiens

<400> SEQUENCE: 8

```
gtcggattgg tgggttgggg gcacaaggca                                  30
```

<210> SEQ ID NO 9
<211> LENGTH: 30
<212> TYPE: DNA
<213> ORGANISM: Homo sapiens

<400> SEQUENCE: 9

```
tggaggagga ggccacagga ggcgggagga                                  30
```

<210> SEQ ID NO 10
<211> LENGTH: 31
<212> TYPE: DNA
<213> ORGANISM: Homo sapiens

<400> SEQUENCE: 10

```
caggaagagc tggaggagga ggcccacagg a                                31
```

<210> SEQ ID NO 11
<211> LENGTH: 1582
<212> TYPE: DNA
<213> ORGANISM: Homo sapiens

<400> SEQUENCE: 11

```
ttgcagatat acacttcaga taactacacc gaggaaatgg gctcagggga ctatgactcc   60
atgaaggaac cctgtttccg tgaagaaaat gctaatttca ataaaatctt cctgcccacc  120
atctactcca tcatcttctt aactggcatt gtgggcaatg gattggtcat cctggtcatg  180
ggttaccaga agaaactgag aagcatgacg gacaagtaca ggctgcacct gtcagtggcc  240
gacctcctct ttgtcatcac gcttcccttc tgggcagttg atgccgtggc aaactggtac  300
tttgggaact tcctatgcaa ggcagtccat gtcatctaca cagtcaacct ctacagcagt  360
gtcctcatcc tggccttcat cagtctggac cgctacctgg ccatcgtcca cgccaccaac  420
agtcagaggc caaggaagct gttggctgaa aaggtggtct atgttggcgt ctggatccct  480
gccctcctgc tgactattcc cgacttcatc tttgccaacg tcagtgaggc agatgacaga  540
tatatctgtg accgcttcta ccccaatgac ttgtgggtgg ttgtgttcca gtttcagcac  600
atcatggttg ccttatcct gcctggtatt gtcatcctgt cctgctattg cattatcatc  660
tccaagctgt cacactccaa gggccaccag aagcgcaagg ccctcaagac cacagtcatc  720
ctcatcctgg ctttcttcgc ctgttggctg ccttactaca ttgggatcag catcgactcc  780
ttcatcctcc tggaaatcat caagcaaggg tgtgagtttg agaacactgt gcacaagtgg  840
atttccatca ccgaggccct agcttttctt cactgttgtc tgaaccccat cctctatgct  900
ttccttggag ccaaatttaa aacctctgcc agcacgcac tcacctctgt gagcagaggg  960
tccagcctca agatcctctc caaaggaaag cgaggtggac attcatctgt ttccactgag 1020
tctgagtctt caagttttca ctccagctaa cacagatgta aaagactttt ttttatacga 1080
taaataactt ttttttaagt tacacatttt tcagatataa aagactgacc aatattgtac 1140
agttttatt gcttgttgga ttttgtctt gtgtttcttt agttttgtg aagtttaatt 1200
gacttattta tataaatttt ttttgtttca tattgatgtg tgtctaggca ggacctgtgg 1260
ccaagttctt agttgctgta tgtctcgtgg taggactgta gaaagggaa ctgaacattc 1320
cagagcgtgt agtgaatcac gtaaagctag aaatgatccc cagctgttta tgcatagata 1380
atctctccat tcccgtggaa cgttttcct gttcttaaga cgtgatttg ctgtagaaga 1440
tggcacttat aaccaaagcc caaagtggta tagaaatgct ggttttcag ttttcaggag 1500
```
tgggttgatt tcagcaccta cagtgtacag tcttgtatta agttgttaat aaaagtacat    1560
gttaaactta cttagtgtta tg                                             1582

<210> SEQ ID NO 12
<211> LENGTH: 9
<212> TYPE: DNA
<213> ORGANISM: Artificial
<220> FEATURE:
<223> OTHER INFORMATION: Homo Sapiens

<400> SEQUENCE: 12 gcggacgcg                                                                  9

<210> SEQ ID NO 13
<211> LENGTH: 25
<212> TYPE: PRT
<213> ORGANISM: Artificial
<220> FEATURE:
<223> OTHER INFORMATION: Consensus Sequence

<400> SEQUENCE: 13

Pro Tyr Lys Cys Pro Glu Cys Gly Lys Ser Phe Ser Gln Lys Ser Asp
1               5                   10                  15

Leu Val Lys His Gln Arg Thr His Thr
            20                  25

<210> SEQ ID NO 14
<211> LENGTH: 25
<212> TYPE: PRT
<213> ORGANISM: Artificial
<220> FEATURE:
<223> OTHER INFORMATION: Consensus Sequence

<400> SEQUENCE: 14

Pro Tyr Lys Cys Ser Glu Cys Gly Lys Ala Phe Ser Gln Lys Ser Asn
1               5                   10                  15

Leu Thr Arg His Gln Arg Ile His Thr
            20                  25

<210> SEQ ID NO 15
<211> LENGTH: 6
<212> TYPE: PRT
<213> ORGANISM: Artificial
<220> FEATURE:
<223> OTHER INFORMATION: Leader Peptide

<400> SEQUENCE: 15

Met Ala Glu Glu Lys Pro
1               5

<210> SEQ ID NO 16
<211> LENGTH: 4
<212> TYPE: PRT
<213> ORGANISM: Homo sapiens

<400> SEQUENCE: 16

Gly Glu Lys Pro
1

<210> SEQ ID NO 17
<211> LENGTH: 4
<212> TYPE: PRT
<213> ORGANISM: Homo sapiens

<400> SEQUENCE: 17

Gly Glu Arg Pro
1

<210> SEQ ID NO 18
<211> LENGTH: 4
<212> TYPE: PRT
<213> ORGANISM: Homo sapiens

<400> SEQUENCE: 18

Gly Gln Lys Pro
1

<210> SEQ ID NO 19
<211> LENGTH: 4
<212> TYPE: PRT
<213> ORGANISM: Homo sapiens

<400> SEQUENCE: 19

Gly Gln Arg Pro
1

<210> SEQ ID NO 20
<211> LENGTH: 5
<212> TYPE: PRT
<213> ORGANISM: Homo sapiens

<400> SEQUENCE: 20

Gly Gly Glu Lys Pro
1               5

<210> SEQ ID NO 21
<211> LENGTH: 5
<212> TYPE: PRT
<213> ORGANISM: Homo sapiens

<400> SEQUENCE: 21

Gly Gly Gln Lys Pro
1               5

<210> SEQ ID NO 22
<211> LENGTH: 7
<212> TYPE: PRT
<213> ORGANISM: Homo sapiens

<400> SEQUENCE: 22

Gly Gly Ser Gly Glu Lys Pro
1               5

<210> SEQ ID NO 23
<211> LENGTH: 7
<212> TYPE: PRT
<213> ORGANISM: Homo sapiens

<400> SEQUENCE: 23

Gly Gly Ser Gly Gln Lys Pro
1               5

<210> SEQ ID NO 24
<211> LENGTH: 10
<212> TYPE: PRT
<213> ORGANISM: Homo sapiens

<400> SEQUENCE: 24

Gly Gly Ser Gly Gly Ser Gly Glu Lys Pro
1               5                   10

```
<210> SEQ ID NO 25
<211> LENGTH: 10
<212> TYPE: PRT
<213> ORGANISM: Homo sapiens

<400> SEQUENCE: 25

Gly Gly Ser Gly Gly Ser Gly Gln Lys Pro
1               5                   10

<210> SEQ ID NO 26
<211> LENGTH: 10
<212> TYPE: DNA
<213> ORGANISM: Homo sapiens

<400> SEQUENCE: 26
gggaaattcc                                                              10

<210> SEQ ID NO 27
<211> LENGTH: 144
<212> TYPE: PRT
<213> ORGANISM: Homo sapiens

<400> SEQUENCE: 27

Ala Ala Arg Asn Ser Gly Pro Lys Lys Arg Lys Val Asp Gly Gly
1               5                   10                  15

Gly Ala Leu Ser Pro Gln His Ser Ala Val Thr Gln Gly Ser Ile Ile
                20                  25                  30

Lys Asn Lys Glu Gly Met Asp Ala Lys Ser Leu Thr Ala Trp Ser Arg
            35                  40                  45

Thr Leu Val Thr Phe Lys Asp Val Phe Val Asp Phe Thr Arg Glu Glu
        50                  55                  60

Trp Lys Leu Leu Asp Thr Ala Gln Gln Ile Val Tyr Arg Asn Val Met
65                  70                  75                  80

Leu Glu Asn Tyr Lys Asn Leu Val Ser Leu Gly Tyr Gln Leu Thr Lys
                85                  90                  95

Pro Asp Val Ile Leu Arg Leu Glu Lys Gly Glu Glu Pro Trp Leu Val
            100                 105                 110

Glu Arg Glu Ile His Gln Glu Thr His Pro Asp Ser Glu Thr Ala Phe
        115                 120                 125

Glu Ile Lys Ser Ser Val Glu Gln Lys Leu Ile Ser Glu Glu Asp Leu
    130                 135                 140

<210> SEQ ID NO 28
<211> LENGTH: 47
<212> TYPE: DNA
<213> ORGANISM: Homo sapiens

<400> SEQUENCE: 28
tccccgcccc agcggcgcat gcgccgcgct cggagcgtgt ttttata                     47

<210> SEQ ID NO 29
<211> LENGTH: 38
<212> TYPE: DNA
<213> ORGANISM: Homo sapiens

<400> SEQUENCE: 29
ccgccccagc ggcgcatgcg ccgcgctcgg agcgtgtt                               38

<210> SEQ ID NO 30
<211> LENGTH: 38
<212> TYPE: DNA
```

```
<213> ORGANISM: Homo sapiens

<400> SEQUENCE: 30
ccgccccagc ggcgcatgcg ccgcgctcgg agcgtgtt                                38

<210> SEQ ID NO 31
<211> LENGTH: 38
<212> TYPE: DNA
<213> ORGANISM: Homo sapiens

<400> SEQUENCE: 31
ccgccccagc ggcgcatgcg ccgcgctcgg agcgtgtt                                38

<210> SEQ ID NO 32
<211> LENGTH: 7
<212> TYPE: PRT
<213> ORGANISM: Artificial
<220> FEATURE:
<223> OTHER INFORMATION: Flexible Linker Sequence

<400> SEQUENCE: 32

Asp Ser Ala Thr Leu Thr Glu
1               5

<210> SEQ ID NO 33
<211> LENGTH: 7
<212> TYPE: PRT
<213> ORGANISM: Artificial
<220> FEATURE:
<223> OTHER INFORMATION: Flexible Linker Sequence

<400> SEQUENCE: 33

Arg Arg Asp Asp Leu Ser Arg
1               5

<210> SEQ ID NO 34
<211> LENGTH: 7
<212> TYPE: PRT
<213> ORGANISM: Artificial
<220> FEATURE:
<223> OTHER INFORMATION: Flexible Linker Sequence

<400> SEQUENCE: 34

Arg Lys Ser Asp Arg Thr Arg
1               5

<210> SEQ ID NO 35
<211> LENGTH: 7
<212> TYPE: PRT
<213> ORGANISM: Artificial
<220> FEATURE:
<223> OTHER INFORMATION: Flexible Linker Sequence

<400> SEQUENCE: 35

Arg Ser Asp Glu Leu Thr Arg
1               5

<210> SEQ ID NO 36
<211> LENGTH: 7
<212> TYPE: PRT
<213> ORGANISM: Artificial
<220> FEATURE:
<223> OTHER INFORMATION: Flexible Linker Sequence

<400> SEQUENCE: 36

Arg Ser Asp Thr Leu Ser Lys
1               5
```

<210> SEQ ID NO 37
<211> LENGTH: 7
<212> TYPE: PRT
<213> ORGANISM: Artificial
<220> FEATURE:
<223> OTHER INFORMATION: Flexible Linker Sequence

<400> SEQUENCE: 37

Gln Lys His Asp Arg Thr Gln
1               5

<210> SEQ ID NO 38
<211> LENGTH: 7
<212> TYPE: PRT
<213> ORGANISM: Artificial
<220> FEATURE:
<223> OTHER INFORMATION: Flexible Linker Sequence

<400> SEQUENCE: 38

Lys Ser Asn Asp Leu Ile Arg
1               5

<210> SEQ ID NO 39
<211> LENGTH: 7
<212> TYPE: PRT
<213> ORGANISM: Artificial
<220> FEATURE:
<223> OTHER INFORMATION: Flexible Linker Sequence

<400> SEQUENCE: 39

Gln Ser Ala His Leu Ser Arg
1               5

<210> SEQ ID NO 40
<211> LENGTH: 7
<212> TYPE: PRT
<213> ORGANISM: Artificial
<220> FEATURE:
<223> OTHER INFORMATION: Flexible Linker Sequence

<400> SEQUENCE: 40

Asp Asn Arg Asp Arg Thr Lys
1               5

<210> SEQ ID NO 41
<211> LENGTH: 7
<212> TYPE: PRT
<213> ORGANISM: Artificial
<220> FEATURE:
<223> OTHER INFORMATION: Flexible Linker Sequence

<400> SEQUENCE: 41

Arg Ser Asp Glu Leu Thr Arg
1               5

<210> SEQ ID NO 42
<211> LENGTH: 7
<212> TYPE: PRT
<213> ORGANISM: Artificial
<220> FEATURE:
<223> OTHER INFORMATION: Flexible Linker Sequence

<400> SEQUENCE: 42

Arg Ser Asp Thr Leu Ser Lys
1               5

```
<210> SEQ ID NO 43
<211> LENGTH: 7
<212> TYPE: PRT
<213> ORGANISM: Artificial
<220> FEATURE:
<223> OTHER INFORMATION: Flexible Linker Sequence

<400> SEQUENCE: 43

Gln Lys His Asp Arg Thr Gln
1               5

<210> SEQ ID NO 44
<211> LENGTH: 7
<212> TYPE: PRT
<213> ORGANISM: Artificial
<220> FEATURE:
<223> OTHER INFORMATION: Flexible Linker Sequence

<400> SEQUENCE: 44

Lys Ser Asn Asp Leu Ile Arg
1               5

<210> SEQ ID NO 45
<211> LENGTH: 7
<212> TYPE: PRT
<213> ORGANISM: Artificial
<220> FEATURE:
<223> OTHER INFORMATION: Flexible Linker Sequence

<400> SEQUENCE: 45

Gln Ser Ala His Leu Ser Arg
1               5

<210> SEQ ID NO 46
<211> LENGTH: 7
<212> TYPE: PRT
<213> ORGANISM: Artificial
<220> FEATURE:
<223> OTHER INFORMATION: Flexible Linker Sequence

<400> SEQUENCE: 46

Asp Asn Arg Asp Arg Thr Lys
1               5

<210> SEQ ID NO 47
<211> LENGTH: 7
<212> TYPE: PRT
<213> ORGANISM: Artificial
<220> FEATURE:
<223> OTHER INFORMATION: Flexible Linker Sequence

<400> SEQUENCE: 47

Arg Ser Thr Asp Leu Ile Arg
1               5

<210> SEQ ID NO 48
<211> LENGTH: 7
<212> TYPE: PRT
<213> ORGANISM: Artificial
<220> FEATURE:
<223> OTHER INFORMATION: Flexible Linker Sequence

<400> SEQUENCE: 48

Thr Ser Ser Asn Leu Ser Ala
1               5

<210> SEQ ID NO 49
<211> LENGTH: 7
```

```
<212> TYPE: PRT
<213> ORGANISM: Artificial
<220> FEATURE:
<223> OTHER INFORMATION: Flexible Linker Sequence

<400> SEQUENCE: 49

Arg Asn Ala Asp Arg Thr Lys
1               5

<210> SEQ ID NO 50
<211> LENGTH: 5
<212> TYPE: PRT
<213> ORGANISM: Homo Sapiens

<400> SEQUENCE: 50

Thr Gly Glu Arg Pro
1               5

<210> SEQ ID NO 51
<211> LENGTH: 15
<212> TYPE: PRT
<213> ORGANISM: Artificial
<220> FEATURE:
<223> OTHER INFORMATION: Flexible Linker Sequence

<400> SEQUENCE: 51

Thr Gly Gly Gly Gly Ser Gly Gly Ser Gly Gly Ser Glu Arg Pro
1               5                   10                  15

<210> SEQ ID NO 52
<211> LENGTH: 21
<212> TYPE: PRT
<213> ORGANISM: Artificial
<220> FEATURE:
<223> OTHER INFORMATION: Flexible Linker Sequence

<400> SEQUENCE: 52

Thr Gly Gly Gly Gly Ser Gly Gly Ser Gly Gly Ser Gly Gly Ser Gly
1               5                   10                  15

Gly Ser Glu Arg Pro
            20

<210> SEQ ID NO 53
<211> LENGTH: 187
<212> TYPE: PRT
<213> ORGANISM: Artificial
<220> FEATURE:
<223> OTHER INFORMATION: Six Finger Domain Protein

<400> SEQUENCE: 53

Met Ala Glu Arg Pro Tyr Ala Cys Pro Val Glu Ser Cys Asp Arg Arg
1               5                   10                  15

Phe Ser Asp Ser Ala Thr Leu Thr Glu His Ile Arg Ile His Thr Gly
                20                  25                  30

Gln Lys Pro Phe Gln Cys Arg Ile Cys Met Arg Asn Phe Ser Arg Arg
            35                  40                  45

Asp Asp Leu Ser Arg His Ile Arg Thr His Thr Gly Glu Lys Pro Phe
    50                  55                  60

Ala Cys Asp Ile Cys Gly Arg Lys Phe Ala Arg Lys Ser Asp Arg Thr
65                  70                  75                  80

Arg His Thr Lys Ile His Thr Gly Gly Gly Gly Ser Gly Gly Ser Gly
                85                  90                  95

Gly Ser Glu Arg Pro Tyr Ala Cys Pro Val Glu Ser Cys Asp Arg Arg
                100                 105                 110
```

Phe Ser Arg Ser Asp Glu Leu Thr Arg His Ile Arg Ile His Thr Gly
            115                 120                 125

Gln Lys Pro Phe Gln Cys Arg Ile Cys Met Arg Asn Phe Ser Arg Ser
            130                 135                 140

Asp Thr Leu Ser Lys His Ile Arg Thr His Thr Gly Glu Lys Pro Phe
145                 150                 155                 160

Ala Cys Asp Ile Cys Gly Arg Lys Phe Ala Gln Lys His Asp Arg Thr
                165                 170                 175

Gln His Thr Lys Ile His Leu Arg Gln Lys Asp
            180                 185

<210> SEQ ID NO 54
<211> LENGTH: 193
<212> TYPE: PRT
<213> ORGANISM: Artificial
<220> FEATURE:
<223> OTHER INFORMATION: Six Finger Domain Protein

<400> SEQUENCE: 54

Met Ala Glu Arg Pro Tyr Ala Cys Pro Val Glu Ser Cys Asp Arg Arg
1               5                   10                  15

Phe Ser Lys Ser Asn Asp Leu Ile Arg His Ile Arg Ile His Thr Gly
                20                  25                  30

Gln Lys Pro Phe Gln Cys Arg Ile Cys Met Arg Asn Phe Ser Gln Ser
            35                  40                  45

Ala His Leu Ser Arg His Ile Arg Thr His Thr Gly Glu Lys Pro Phe
        50                  55                  60

Ala Cys Asp Ile Cys Gly Arg Lys Phe Ala Asp Asn Arg Asp Arg Thr
65                  70                  75                  80

Lys His Thr Lys Ile His Thr Gly Gly Gly Ser Gly Gly Ser Gly
                85                  90                  95

Gly Ser Gly Gly Ser Gly Ser Glu Arg Pro Tyr Ala Cys Pro Val
            100                 105                 110

Glu Ser Cys Asp Arg Arg Phe Ser Arg Ser Asp Glu Leu Thr Arg His
            115                 120                 125

Ile Arg Ile His Thr Gly Gln Lys Pro Phe Gln Cys Arg Ile Cys Met
            130                 135                 140

Arg Asn Phe Ser Arg Ser Asp Thr Leu Ser Lys His Ile Arg Thr His
145                 150                 155                 160

Thr Gly Glu Lys Pro Phe Ala Cys Asp Ile Cys Gly Arg Lys Phe Ala
                165                 170                 175

Gln Lys His Asp Arg Thr Gln His Thr Lys Ile His Leu Arg Gln Lys
            180                 185                 190

Asp

<210> SEQ ID NO 55
<211> LENGTH: 193
<212> TYPE: PRT
<213> ORGANISM: Artificial
<220> FEATURE:
<223> OTHER INFORMATION: Six Finger Domain Protein

<400> SEQUENCE: 55

Met Ala Glu Arg Pro Tyr Ala Cys Pro Val Glu Ser Cys Asp Arg Arg
1               5                   10                  15

Phe Ser Lys Ser Asn Asp Leu Ile Arg His Ile Arg Ile His Thr Gly
                20                  25                  30

Gln Lys Pro Phe Gln Cys Arg Ile Cys Met Arg Asn Phe Ser Gln Ser
                35                  40                  45

Ala His Leu Ser Arg His Ile Arg Thr His Thr Gly Glu Lys Pro Phe
 50                  55                  60

Ala Cys Asp Ile Cys Gly Arg Lys Phe Ala Asp Asn Arg Asp Arg Thr
 65                  70                  75                  80

Lys His Thr Lys Ile His Thr Gly Gly Gly Ser Gly Gly Ser Gly
                 85                  90                  95

Gly Ser Gly Gly Ser Gly Gly Ser Glu Arg Pro Tyr Ala Cys Pro Val
                100                 105                 110

Glu Ser Cys Asp Arg Arg Phe Ser Arg Ser Thr Asp Leu Ile Arg His
                115                 120                 125

Ile Arg Ile His Thr Gly Gln Lys Pro Phe Gln Cys Arg Ile Cys Met
            130                 135                 140

Arg Asn Phe Ser Thr Ser Ser Asn Leu Ser Ala His Ile Arg Thr His
145                 150                 155                 160

Thr Gly Glu Lys Pro Phe Ala Cys Asp Ile Cys Gly Arg Lys Phe Ala
                165                 170                 175

Arg Asn Ala Asp Arg Thr Lys His Thr Lys Ile His Leu Arg Gln Lys
                180                 185                 190

Asp

<210> SEQ ID NO 56
<211> LENGTH: 331
<212> TYPE: PRT
<213> ORGANISM: Artificial
<220> FEATURE:
<223> OTHER INFORMATION: Six Finger Domain Protein and Repressor

<400> SEQUENCE: 56

Met Ala Glu Arg Pro Tyr Ala Cys Pro Val Glu Ser Cys Asp Arg Arg
 1               5                  10                  15

Phe Ser Asp Ser Ala Thr Leu Thr Glu His Ile Arg Ile His Thr Gly
                20                  25                  30

Gln Lys Pro Phe Gln Cys Arg Ile Cys Met Arg Asn Phe Ser Arg Arg
                35                  40                  45

Asp Asp Leu Ser Arg His Ile Arg Thr His Thr Gly Glu Lys Pro Phe
 50                  55                  60

Ala Cys Asp Ile Cys Gly Arg Lys Phe Ala Arg Lys Ser Asp Arg Thr
 65                  70                  75                  80

Arg His Thr Lys Ile His Thr Gly Gly Gly Gly Ser Gly Gly Ser Gly
                 85                  90                  95

Gly Ser Glu Arg Pro Tyr Ala Cys Pro Val Glu Ser Cys Asp Arg Arg
                100                 105                 110

Phe Ser Arg Ser Asp Glu Leu Thr Arg His Ile Arg Ile His Thr Gly
                115                 120                 125

Gln Lys Pro Phe Gln Cys Arg Ile Cys Met Arg Asn Phe Ser Arg Ser
            130                 135                 140

Asp Thr Leu Ser Lys His Ile Arg Thr His Thr Gly Glu Lys Pro Phe
145                 150                 155                 160

Ala Cys Asp Ile Cys Gly Arg Lys Phe Ala Gln Lys His Asp Arg Thr
                165                 170                 175

Gln His Thr Lys Ile His Leu Arg Gln Lys Asp Ala Ala Arg Asn Ser
                180                 185                 190

Gly Pro Lys Lys Lys Arg Lys Val Asp Gly Gly Ala Leu Ser Pro
                195                 200                 205

Gln His Ser Ala Val Thr Gln Gly Ser Ile Ile Lys Asn Lys Glu Gly
    210                 215                 220

Met Asp Ala Lys Ser Leu Thr Ala Trp Ser Arg Thr Leu Val Thr Phe
225                 230                 235                 240

Lys Asp Val Phe Val Asp Phe Thr Arg Glu Trp Lys Leu Leu Asp
                245                 250                 255

Thr Ala Gln Gln Ile Val Tyr Arg Asn Val Met Leu Glu Asn Tyr Lys
            260                 265                 270

Asn Leu Val Ser Leu Gly Tyr Gln Leu Thr Lys Pro Asp Val Ile Leu
        275                 280                 285

Arg Leu Glu Lys Gly Glu Glu Pro Trp Leu Val Glu Arg Glu Ile His
    290                 295                 300

Gln Glu Thr His Pro Asp Ser Glu Thr Ala Phe Glu Ile Lys Ser Ser
305                 310                 315                 320

Val Glu Gln Lys Leu Ile Ser Glu Glu Asp Leu
                325                 330

<210> SEQ ID NO 57
<211> LENGTH: 337
<212> TYPE: PRT
<213> ORGANISM: Artificial
<220> FEATURE:
<223> OTHER INFORMATION: Six Finger Domain Protein and Repressor

<400> SEQUENCE: 57

Met Ala Glu Arg Pro Tyr Ala Cys Pro Val Glu Ser Cys Asp Arg Arg
1               5                   10                  15

Phe Ser Lys Ser Asn Asp Leu Ile Arg His Ile Arg Ile His Thr Gly
            20                  25                  30

Gln Lys Pro Phe Gln Cys Arg Ile Cys Met Arg Asn Phe Ser Gln Ser
        35                  40                  45

Ala His Leu Ser Arg His Ile Arg Thr His Thr Gly Glu Lys Pro Phe
    50                  55                  60

Ala Cys Asp Ile Cys Gly Arg Lys Phe Ala Asp Asn Arg Asp Arg Thr
65                  70                  75                  80

Lys His Thr Lys Ile His Thr Gly Gly Gly Gly Ser Gly Gly Ser Gly
                85                  90                  95

Gly Ser Gly Gly Ser Gly Gly Ser Glu Arg Pro Tyr Ala Cys Pro Val
            100                 105                 110

Glu Ser Cys Asp Arg Arg Phe Ser Arg Ser Asp Glu Leu Thr Arg His
        115                 120                 125

Ile Arg Ile His Thr Gly Gln Lys Pro Phe Gln Cys Arg Ile Cys Met
    130                 135                 140

Arg Asn Phe Ser Arg Ser Asp Thr Leu Ser Lys His Ile Arg Thr His
145                 150                 155                 160

Thr Gly Glu Lys Pro Phe Ala Cys Asp Ile Cys Gly Arg Lys Phe Ala
                165                 170                 175

Gln Lys His Asp Arg Thr Gln His Thr Lys Ile His Leu Arg Gln Lys
            180                 185                 190

Asp Ala Ala Arg Asn Ser Gly Pro Lys Lys Arg Lys Val Asp Gly
        195                 200                 205

Gly Gly Ala Leu Ser Pro Gln His Ser Ala Val Thr Gln Gly Ser Ile
    210                 215                 220

Ile Lys Asn Lys Glu Gly Met Asp Ala Lys Ser Leu Thr Ala Trp Ser
225                 230                 235                 240

```
Arg Thr Leu Val Thr Phe Lys Asp Val Phe Val Asp Phe Thr Arg Glu
                245                 250                 255

Glu Trp Lys Leu Leu Asp Thr Ala Gln Gln Ile Val Tyr Arg Asn Val
                260                 265                 270

Met Leu Glu Asn Tyr Lys Asn Leu Val Ser Leu Gly Tyr Gln Leu Thr
                275                 280                 285

Lys Pro Asp Val Ile Leu Arg Leu Glu Lys Gly Glu Pro Trp Leu
                290                 295                 300

Val Glu Arg Glu Ile His Gln Glu Thr His Pro Asp Ser Glu Thr Ala
305                 310                 315                 320

Phe Glu Ile Lys Ser Ser Val Glu Gln Lys Leu Ile Ser Glu Glu Asp
                325                 330                 335

Leu

<210> SEQ ID NO 58
<211> LENGTH: 337
<212> TYPE: PRT
<213> ORGANISM: Artificial
<220> FEATURE:
<223> OTHER INFORMATION: Six Finger Domain Protein and Repressor

<400> SEQUENCE: 58

Met Ala Glu Arg Pro Tyr Ala Cys Pro Val Glu Ser Cys Asp Arg Arg
1               5                   10                  15

Phe Ser Lys Ser Asn Asp Leu Ile Arg His Ile Arg Ile His Thr Gly
                20                  25                  30

Gln Lys Pro Phe Gln Cys Arg Ile Cys Met Arg Asn Phe Ser Gln Ser
                35                  40                  45

Ala His Leu Ser Arg His Ile Arg Thr His Thr Gly Glu Lys Pro Phe
            50                  55                  60

Ala Cys Asp Ile Cys Gly Arg Lys Phe Ala Asp Asn Arg Asp Arg Thr
65                  70                  75                  80

Lys His Thr Lys Ile His Thr Gly Gly Gly Ser Gly Gly Ser Gly
                85                  90                  95

Gly Ser Gly Gly Ser Gly Gly Ser Glu Arg Pro Tyr Ala Cys Pro Val
            100                 105                 110

Glu Ser Cys Asp Arg Arg Phe Ser Arg Ser Thr Asp Leu Ile Arg His
                115                 120                 125

Ile Arg Ile His Thr Gly Gln Lys Pro Phe Gln Cys Arg Ile Cys Met
130                 135                 140

Arg Asn Phe Ser Thr Ser Ser Asn Leu Ser Ala His Ile Arg Thr His
145                 150                 155                 160

Thr Gly Glu Lys Pro Phe Ala Cys Asp Ile Cys Gly Arg Lys Phe Ala
                165                 170                 175

Arg Asn Ala Asp Arg Thr Lys His Thr Lys Ile His Leu Arg Gln Lys
                180                 185                 190

Asp Ala Ala Arg Asn Ser Gly Pro Lys Lys Arg Lys Val Asp Gly
            195                 200                 205

Gly Gly Ala Leu Ser Pro Gln His Ser Ala Val Thr Gln Gly Ser Ile
            210                 215                 220

Ile Lys Asn Lys Glu Gly Met Asp Ala Lys Ser Leu Thr Ala Trp Ser
225                 230                 235                 240

Arg Thr Leu Val Thr Phe Lys Asp Val Phe Val Asp Phe Thr Arg Glu
                245                 250                 255

Glu Trp Lys Leu Leu Asp Thr Ala Gln Gln Ile Val Tyr Arg Asn Val
                260                 265                 270
```

```
Met Leu Glu Asn Tyr Lys Asn Leu Val Ser Leu Gly Tyr Gln Leu Thr
            275                 280                 285

Lys Pro Asp Val Ile Leu Arg Leu Glu Lys Gly Glu Glu Pro Trp Leu
        290                 295                 300

Val Glu Arg Glu Ile His Gln Glu Thr His Pro Asp Ser Glu Thr Ala
305                 310                 315                 320

Phe Glu Ile Lys Ser Ser Val Glu Gln Lys Leu Ile Ser Glu Glu Asp
                325                 330                 335

Leu

<210> SEQ ID NO 59
<211> LENGTH: 54
<212> TYPE: DNA
<213> ORGANISM: Homo sapiens

<400> SEQUENCE: 59
gcctcctcct cccgcctcct gtggcctcct cctccagctc ttcctgtccc gctg          54

<210> SEQ ID NO 60
<211> LENGTH: 32
<212> TYPE: DNA
<213> ORGANISM: Homo sapiens

<400> SEQUENCE: 60
tggtcggatt ggtgggttgg gggcacaagg ca                                   32

<210> SEQ ID NO 61
<211> LENGTH: 30
<212> TYPE: DNA
<213> ORGANISM: Homo sapiens

<400> SEQUENCE: 61
gtcggattgg tgggttgggg gcacaaggca                                      30

<210> SEQ ID NO 62
<211> LENGTH: 30
<212> TYPE: DNA
<213> ORGANISM: Homo sapiens

<400> SEQUENCE: 62
tggaggagga ggccacagga ggcgggagga                                      30

<210> SEQ ID NO 63
<211> LENGTH: 31
<212> TYPE: DNA
<213> ORGANISM: Homo sapiens

<400> SEQUENCE: 63
caggaagagc tggaggagga ggcccacagg a                                    31

<210> SEQ ID NO 64
<211> LENGTH: 22
<212> TYPE: DNA
<213> ORGANISM: Homo sapiens

<400> SEQUENCE: 64
ggattggtgg gttgggggca ca                                              22

<210> SEQ ID NO 65
<211> LENGTH: 21
<212> TYPE: DNA
<213> ORGANISM: Homo sapiens
```

<400> SEQUENCE: 65
ccgcctcctg tggcctcctc c						21

<210> SEQ ID NO 66
<211> LENGTH: 22
<212> TYPE: DNA
<213> ORGANISM: Homo sapiens

<400> SEQUENCE: 66
gtggcctcct cctccagctc tt						22

<210> SEQ ID NO 67
<211> LENGTH: 7
<212> TYPE: PRT
<213> ORGANISM: Artificial
<220> FEATURE:
<223> OTHER INFORMATION: Flexible Linker Sequence

<400> SEQUENCE: 67

Ala Ser Ala Asp Leu Thr Arg
1               5

<210> SEQ ID NO 68
<211> LENGTH: 7
<212> TYPE: PRT
<213> ORGANISM: Artificial
<220> FEATURE:
<223> OTHER INFORMATION: Flexible Linker Sequence

<400> SEQUENCE: 68

Arg Arg Asp His Leu Ser Glu
1               5

<210> SEQ ID NO 69
<211> LENGTH: 7
<212> TYPE: PRT
<213> ORGANISM: Artificial
<220> FEATURE:
<223> OTHER INFORMATION: Flexible Linker Sequence

<400> SEQUENCE: 69

Arg Asn Asp Ser Arg Thr Asn
1               5

<210> SEQ ID NO 70
<211> LENGTH: 7
<212> TYPE: PRT
<213> ORGANISM: Artificial
<220> FEATURE:
<223> OTHER INFORMATION: Flexible Linker Sequence

<400> SEQUENCE: 70

Arg Ser Gln His Leu Thr Glu
1               5

<210> SEQ ID NO 71
<211> LENGTH: 7
<212> TYPE: PRT
<213> ORGANISM: Artificial
<220> FEATURE:
<223> OTHER INFORMATION: Flexible Linker Sequence

<400> SEQUENCE: 71

Thr Ser Ser His Leu Ser Val
1               5

```
<210> SEQ ID NO 72
<211> LENGTH: 7
<212> TYPE: PRT
<213> ORGANISM: Artificial
<220> FEATURE:
<223> OTHER INFORMATION: Flexible Linker Sequence

<400> SEQUENCE: 72

His Ser Asn Ala Arg Lys Thr
1               5

<210> SEQ ID NO 73
<211> LENGTH: 7
<212> TYPE: PRT
<213> ORGANISM: Artificial
<220> FEATURE:
<223> OTHER INFORMATION: Flexible Linker Sequence

<400> SEQUENCE: 73

Arg Ser Asp Glu Leu Thr Arg
1               5

<210> SEQ ID NO 74
<211> LENGTH: 7
<212> TYPE: PRT
<213> ORGANISM: Artificial
<220> FEATURE:
<223> OTHER INFORMATION: Flexible Linker Sequence

<400> SEQUENCE: 74

Arg Ser Asp Asn Leu Ser Glu
1               5

<210> SEQ ID NO 75
<211> LENGTH: 7
<212> TYPE: PRT
<213> ORGANISM: Artificial
<220> FEATURE:
<223> OTHER INFORMATION: Flexible Linker Sequence

<400> SEQUENCE: 75

Arg Ser Asp Asn Arg Lys Thr
1               5

<210> SEQ ID NO 76
<211> LENGTH: 7
<212> TYPE: PRT
<213> ORGANISM: Artificial
<220> FEATURE:
<223> OTHER INFORMATION: Linker Sequence

<400> SEQUENCE: 76

Asp Asn Arg Asp Leu Ile Arg
1               5

<210> SEQ ID NO 77
<211> LENGTH: 7
<212> TYPE: PRT
<213> ORGANISM: Artificial
<220> FEATURE:
<223> OTHER INFORMATION: Linker Sequence

<400> SEQUENCE: 77

Arg Ser Asp Asp Leu Ser Arg
1               5

<210> SEQ ID NO 78
```

```
<211> LENGTH: 7
<212> TYPE: PRT
<213> ORGANISM: Artificial
<220> FEATURE:
<223> OTHER INFORMATION: Linker Sequence

<400> SEQUENCE: 78

Arg Ser Asp Asn Arg Thr Lys
1               5

<210> SEQ ID NO 79
<211> LENGTH: 7
<212> TYPE: PRT
<213> ORGANISM: Artificial
<220> FEATURE:
<223> OTHER INFORMATION: Linker Sequence

<400> SEQUENCE: 79

Asp Asn Arg Asp Leu Ile Arg
1               5

<210> SEQ ID NO 80
<211> LENGTH: 7
<212> TYPE: PRT
<213> ORGANISM: Artificial
<220> FEATURE:
<223> OTHER INFORMATION: Linker Sequence

<400> SEQUENCE: 80

Arg Ser Asp Asp Leu Ser Arg
1               5

<210> SEQ ID NO 81
<211> LENGTH: 7
<212> TYPE: PRT
<213> ORGANISM: Artificial
<220> FEATURE:
<223> OTHER INFORMATION: Linker Sequence

<400> SEQUENCE: 81

Arg Ser Asp Asn Arg Thr Lys
1               5

<210> SEQ ID NO 82
<211> LENGTH: 7
<212> TYPE: PRT
<213> ORGANISM: Artificial
<220> FEATURE:
<223> OTHER INFORMATION: Linker Sequence

<400> SEQUENCE: 82

Asp Ser Ala His Leu Ile Arg
1               5

<210> SEQ ID NO 83
<211> LENGTH: 7
<212> TYPE: PRT
<213> ORGANISM: Artificial
<220> FEATURE:
<223> OTHER INFORMATION: Linker Sequence

<400> SEQUENCE: 83

Thr Ser Ser Asp Leu Ser Arg
1               5

<210> SEQ ID NO 84
<211> LENGTH: 7
<212> TYPE: PRT
```

```
<213> ORGANISM: Artificial
<220> FEATURE:
<223> OTHER INFORMATION: Linker Sequence

<400> SEQUENCE: 84

Gln Ser Ala His Arg Lys Thr
1               5

<210> SEQ ID NO 85
<211> LENGTH: 7
<212> TYPE: PRT
<213> ORGANISM: Artificial
<220> FEATURE:
<223> OTHER INFORMATION: Linker Sequence

<400> SEQUENCE: 85

Arg Ser Asp Glu Leu Thr Arg
1               5

<210> SEQ ID NO 86
<211> LENGTH: 7
<212> TYPE: PRT
<213> ORGANISM: Artificial
<220> FEATURE:
<223> OTHER INFORMATION: Linker Sequence

<400> SEQUENCE: 86

Arg Ser Asp Asn Leu Ser Glu
1               5

<210> SEQ ID NO 87
<211> LENGTH: 7
<212> TYPE: PRT
<213> ORGANISM: Artificial
<220> FEATURE:
<223> OTHER INFORMATION: Linker Sequence

<400> SEQUENCE: 87

Arg Ser Asp Asn Arg Lys Thr
1               5

<210> SEQ ID NO 88
<211> LENGTH: 7
<212> TYPE: PRT
<213> ORGANISM: Artificial
<220> FEATURE:
<223> OTHER INFORMATION: Linker Sequence

<400> SEQUENCE: 88

Asp Asn Arg Asp Leu Ile Arg
1               5

<210> SEQ ID NO 89
<211> LENGTH: 7
<212> TYPE: PRT
<213> ORGANISM: Artificial
<220> FEATURE:
<223> OTHER INFORMATION: Linker Sequence

<400> SEQUENCE: 89

Arg Ser Asp Asp Leu Ser Arg
1               5

<210> SEQ ID NO 90
<211> LENGTH: 7
<212> TYPE: PRT
<213> ORGANISM: Artificial
<220> FEATURE:
```

```
<223> OTHER INFORMATION: Linker Sequence

<400> SEQUENCE: 90

Arg Ser Asp Asn Arg Thr Lys
1               5

<210> SEQ ID NO 91
<211> LENGTH: 178
<212> TYPE: PRT
<213> ORGANISM: Artificial
<220> FEATURE:
<223> OTHER INFORMATION: Six Finger Domain Protein

<400> SEQUENCE: 91

Met Ala Glu Arg Pro Tyr Ala Cys Pro Val Glu Ser Cys Asp Arg Arg
1               5                   10                  15

Phe Ser Ala Ser Ala Asp Leu Thr Arg His Ile Arg Ile His Thr Gly
                20                  25                  30

Gln Lys Pro Phe Gln Cys Arg Ile Cys Met Arg Asn Phe Ser Arg Arg
            35                  40                  45

Asp His Leu Ser Glu His Ile Arg Thr His Thr Gly Glu Lys Pro Phe
        50                  55                  60

Ala Cys Asp Ile Cys Gly Arg Lys Phe Ala Arg Asn Asp Ser Arg Thr
65                  70                  75                  80

Asn His Thr Lys Ile His Thr Gly Ser Glu Arg Pro Tyr Ala Cys Pro
                85                  90                  95

Val Glu Ser Cys Asp Arg Arg Phe Ser Arg Ser Gln His Leu Thr Glu
                100                 105                 110

His Ile Arg Ile His Thr Gly Gln Lys Pro Phe Gln Cys Arg Ile Cys
            115                 120                 125

Met Arg Asn Phe Ser Thr Ser Ser His Leu Ser Val His Ile Arg Thr
        130                 135                 140

His Thr Gly Glu Lys Pro Phe Ala Cys Asp Ile Cys Gly Arg Lys Phe
145                 150                 155                 160

Ala His Ser Asn Ala Arg Lys Thr His Thr Lys Ile His Leu Arg Gln
                165                 170                 175

Lys Asp

<210> SEQ ID NO 92
<211> LENGTH: 181
<212> TYPE: PRT
<213> ORGANISM: Artificial
<220> FEATURE:
<223> OTHER INFORMATION: Six Finger Domain Protein

<400> SEQUENCE: 92

Met Ala Glu Arg Pro Tyr Ala Cys Pro Val Glu Ser Cys Asp Arg Arg
1               5                   10                  15

Phe Ser Arg Ser Asp Glu Leu Thr Arg His Ile Arg Ile His Thr Gly
                20                  25                  30

Gln Lys Pro Phe Gln Cys Arg Ile Cys Met Arg Asn Phe Ser Arg Ser
            35                  40                  45

Asp Asn Leu Ser Glu His Ile Arg Thr His Thr Gly Glu Lys Pro Phe
        50                  55                  60

Ala Cys Asp Ile Cys Gly Arg Lys Phe Ala Arg Ser Asp Asn Arg Lys
65                  70                  75                  80

Thr His Thr Lys Ile His Thr Gly Gly Gly Gly Ser Glu Arg Pro Tyr
                85                  90                  95
```

```
Ala Cys Pro Val Glu Ser Cys Asp Arg Arg Phe Ser Asp Asn Arg Asp
            100                 105                 110

Leu Ile Arg His Ile Arg Ile His Thr Gly Gln Lys Pro Phe Gln Cys
        115                 120                 125

Arg Ile Cys Met Arg Asn Phe Ser Arg Ser Asp Leu Ser Arg His
    130                 135                 140

Ile Arg Thr His Thr Gly Glu Lys Pro Phe Ala Cys Asp Ile Cys Gly
145                 150                 155                 160

Arg Lys Phe Ala Arg Ser Asp Asn Arg Thr Lys His Thr Lys Ile His
                165                 170                 175

Leu Arg Gln Lys Asp
            180

<210> SEQ ID NO 93
<211> LENGTH: 181
<212> TYPE: PRT
<213> ORGANISM: Artificial
<220> FEATURE:
<223> OTHER INFORMATION: Six Finger Domain Protein

<400> SEQUENCE: 93

Met Ala Glu Arg Pro Tyr Ala Cys Pro Val Glu Ser Cys Asp Arg Arg
1               5                   10                  15

Phe Ser Asp Asn Arg Asp Leu Ile Arg His Ile Arg Ile His Thr Gly
            20                  25                  30

Gln Lys Pro Phe Gln Cys Arg Ile Cys Met Arg Asn Phe Ser Arg Ser
        35                  40                  45

Asp Asp Leu Ser Arg His Ile Arg Thr His Thr Gly Glu Lys Pro Phe
    50                  55                  60

Ala Cys Asp Ile Cys Gly Arg Lys Phe Ala Arg Ser Asn Asn Arg Thr
65                  70                  75                  80

Lys His Thr Lys Ile His Thr Gly Gly Gly Gly Ser Glu Arg Pro Tyr
                85                  90                  95

Ala Cys Pro Val Glu Ser Cys Asp Arg Arg Phe Ser Asp Ser Ala His
            100                 105                 110

Leu Ile Arg His Ile Arg Ile His Thr Gly Gln Lys Pro Phe Gln Cys
        115                 120                 125

Arg Ile Cys Met Arg Asn Phe Ser Thr Ser Asp Leu Ser Arg His
    130                 135                 140

Ile Arg Thr His Thr Gly Glu Lys Pro Phe Ala Cys Asp Ile Cys Gly
145                 150                 155                 160

Arg Lys Phe Ala Gln Ser Ala His Arg Lys Thr His Thr Lys Ile His
                165                 170                 175

Leu Arg Gln Lys Asp
            180

<210> SEQ ID NO 94
<211> LENGTH: 184
<212> TYPE: PRT
<213> ORGANISM: Artificial
<220> FEATURE:
<223> OTHER INFORMATION: Six Finger Domain Protein

<400> SEQUENCE: 94

Met Ala Glu Arg Pro Tyr Ala Cys Pro Val Glu Ser Cys Asp Arg Arg
1               5                   10                  15

Phe Ser Arg Ser Asp Glu Leu Thr Arg His Ile Arg Ile His Thr Gly
            20                  25                  30
```

```
Gln Lys Pro Phe Gln Cys Arg Ile Cys Met Arg Asn Phe Ser Arg Ser
            35                  40                  45

Asp Asn Leu Ser Glu His Ile Arg Thr His Thr Gly Glu Lys Pro Phe
    50                  55                  60

Ala Cys Asp Ile Cys Gly Arg Lys Phe Ala Arg Ser Asp Asn Arg Lys
65                  70                  75                  80

Thr His Thr Lys Ile His Thr Gly Gly Gly Ser Gly Gly Ser Glu
                85                  90                  95

Arg Pro Tyr Ala Cys Pro Val Glu Ser Cys Asp Arg Arg Phe Ser Asp
            100                 105                 110

Asn Arg Asp Leu Ile Arg His Ile Arg Ile His Thr Gly Gln Lys Pro
    115                 120                 125

Phe Gln Cys Arg Ile Cys Met Arg Asn Phe Ser Arg Ser Asp Asp Leu
    130                 135                 140

Ser Arg His Ile Arg Thr His Thr Gly Glu Lys Pro Phe Ala Cys Asp
145                 150                 155                 160

Ile Cys Gly Arg Lys Phe Ala Arg Ser Asp Asn Arg Thr Lys His Thr
                165                 170                 175

Lys Ile His Leu Arg Gln Lys Asp
                180

<210> SEQ ID NO 95
<211> LENGTH: 322
<212> TYPE: PRT
<213> ORGANISM: Artificial
<220> FEATURE:
<223> OTHER INFORMATION: Six Finger Domain Protein and Repressor

<400> SEQUENCE: 95

Met Ala Glu Arg Pro Tyr Ala Cys Pro Val Glu Ser Cys Asp Arg Arg
1               5                   10                  15

Phe Ser Ala Ser Ala Asp Leu Thr Arg His Ile Arg Ile His Thr Gly
            20                  25                  30

Gln Lys Pro Phe Gln Cys Arg Ile Cys Met Arg Asn Phe Ser Arg Arg
            35                  40                  45

Asp His Leu Ser Glu His Ile Arg Thr His Thr Gly Glu Lys Pro Phe
    50                  55                  60

Ala Cys Asp Ile Cys Gly Arg Lys Phe Ala Arg Asn Asp Ser Arg Thr
65                  70                  75                  80

Asn His Thr Lys Ile His Thr Gly Ser Glu Arg Pro Tyr Ala Cys Pro
                85                  90                  95

Val Glu Ser Cys Asp Arg Arg Phe Ser Arg Ser Gln His Leu Thr Glu
            100                 105                 110

His Ile Arg Ile His Thr Gly Gln Lys Pro Phe Gln Cys Arg Ile Cys
    115                 120                 125

Met Arg Asn Phe Ser Thr Ser Ser His Leu Ser Val His Ile Arg Thr
    130                 135                 140

His Thr Gly Glu Lys Pro Phe Ala Cys Asp Ile Cys Gly Arg Lys Phe
145                 150                 155                 160

Ala His Ser Asn Ala Arg Lys Thr His Thr Lys Ile His Leu Arg Gln
                165                 170                 175

Lys Asp Ala Ala Arg Asn Ser Gly Pro Lys Lys Arg Lys Val Asp
            180                 185                 190

Gly Gly Gly Ala Leu Ser Pro Gln His Ser Ala Val Thr Gln Gly Ser
            195                 200                 205

Ile Ile Lys Asn Lys Glu Gly Met Asp Ala Lys Ser Leu Thr Ala Trp
```

-continued

```
            210                 215                 220
Ser Arg Thr Leu Val Thr Phe Lys Asp Val Phe Val Asp Phe Thr Arg
225                 230                 235                 240

Glu Glu Trp Lys Leu Leu Asp Thr Ala Gln Gln Ile Val Tyr Arg Asn
                245                 250                 255

Val Met Leu Glu Asn Tyr Lys Asn Leu Val Ser Leu Gly Tyr Gln Leu
            260                 265                 270

Thr Lys Pro Asp Val Ile Leu Arg Leu Glu Lys Gly Glu Glu Pro Trp
        275                 280                 285

Leu Val Glu Arg Glu Ile His Gln Gly Thr His Pro Asp Ser Glu Thr
    290                 295                 300

Ala Phe Glu Ile Lys Ser Ser Val Gln Lys Leu Ile Ser Glu Glu
305                 310                 315                 320

Asp Leu

<210> SEQ ID NO 96
<211> LENGTH: 325
<212> TYPE: PRT
<213> ORGANISM: Artificial
<220> FEATURE:
<223> OTHER INFORMATION: Six Finger Domain Protein and Repressor

<400> SEQUENCE: 96

Met Ala Glu Arg Pro Tyr Ala Cys Pro Val Glu Ser Cys Asp Arg Arg
1               5                   10                  15

Phe Ser Arg Ser Asp Glu Leu Thr Arg His Ile Arg Ile His Thr Gly
                20                  25                  30

Gln Lys Pro Phe Gln Cys Arg Ile Cys Met Arg Asn Phe Ser Arg Ser
            35                  40                  45

Asp Asn Leu Ser Glu His Ile Arg Thr His Thr Gly Glu Lys Pro Phe
        50                  55                  60

Ala Cys Asp Ile Cys Gly Arg Lys Phe Ala Arg Ser Asp Asn Arg Lys
65                  70                  75                  80

Thr His Thr Lys Ile His Thr Gly Gly Gly Gly Ser Glu Arg Pro Tyr
                85                  90                  95

Ala Cys Pro Val Glu Ser Cys Asp Arg Arg Phe Ser Asp Asn Arg Asp
            100                 105                 110

Leu Ile Arg His Ile Arg Ile His Thr Gly Gln Lys Pro Phe Gln Cys
        115                 120                 125

Arg Ile Cys Met Arg Asn Phe Ser Arg Ser Asp Leu Ser Arg His
130                 135                 140

Ile Arg Thr His Thr Gly Glu Lys Pro Phe Ala Cys Asp Ile Cys Gly
145                 150                 155                 160

Arg Lys Phe Ala Arg Ser Asp Asn Arg Thr Lys His Thr Lys Ile His
                165                 170                 175

Leu Arg Gln Lys Asp Ala Ala Arg Asn Ser Gly Pro Lys Lys Lys Arg
            180                 185                 190

Lys Val Asp Gly Gly Gly Ala Leu Ser Pro Gln His Ser Ala Val Thr
        195                 200                 205

Gln Gly Ser Ile Ile Lys Asn Lys Glu Gly Met Asp Ala Lys Ser Leu
    210                 215                 220

Thr Ala Trp Ser Arg Thr Leu Val Thr Phe Lys Asp Val Phe Val Asp
225                 230                 235                 240

Phe Thr Arg Glu Glu Trp Lys Leu Leu Asp Thr Ala Gln Gln Ile Val
                245                 250                 255
```

```
Tyr Arg Asn Val Met Leu Glu Asn Tyr Lys Asn Leu Val Ser Leu Gly
            260                 265                 270

Tyr Gln Leu Thr Lys Pro Asp Val Ile Leu Arg Leu Glu Lys Gly Glu
            275                 280                 285

Glu Pro Trp Leu Val Glu Arg Glu Ile His Gln Glu Thr His Pro Asp
290                 295                 300

Ser Glu Thr Ala Phe Glu Ile Lys Ser Val Glu Gln Lys Leu Ile
305                 310                 315                 320

Ser Glu Glu Asp Leu
            325

<210> SEQ ID NO 97
<211> LENGTH: 325
<212> TYPE: PRT
<213> ORGANISM: Artificial
<220> FEATURE:
<223> OTHER INFORMATION: Six Finger Domain Protein and Repressor

<400> SEQUENCE: 97

Met Ala Glu Arg Pro Tyr Ala Cys Pro Val Glu Ser Cys Asp Arg Arg
1               5                   10                  15

Phe Ser Asp Asn Arg Asp Leu Ile Arg His Ile Arg Ile His Thr Gly
            20                  25                  30

Gln Lys Pro Phe Gln Cys Arg Ile Cys Met Arg Asn Phe Ser Arg Ser
            35                  40                  45

Asp Asp Leu Ser Arg His Ile Arg Thr His Thr Gly Glu Lys Pro Phe
        50                  55                  60

Ala Cys Asp Ile Cys Gly Arg Lys Phe Ala Arg Ser Asp Asn Arg Thr
65                  70                  75                  80

Lys His Thr Lys Ile His Thr Gly Gly Gly Ser Glu Arg Pro Tyr
            85                  90                  95

Ala Cys Pro Val Glu Ser Cys Asp Arg Arg Phe Ser Asp Ser Ala His
            100                 105                 110

Leu Ile Arg His Ile Arg Ile His Thr Gly Gln Lys Pro Phe Gln Cys
            115                 120                 125

Arg Ile Cys Met Arg Asn Phe Ser Thr Ser Ser Asp Leu Ser Arg His
        130                 135                 140

Ile Arg Thr His Thr Gly Glu Lys Pro Phe Ala Cys Asp Ile Cys Gly
145                 150                 155                 160

Arg Lys Phe Ala Gln Ser Ala His Arg Lys Thr His Thr Lys Ile His
            165                 170                 175

Leu Arg Gln Lys Asp Ala Ala Arg Asn Ser Gly Pro Lys Lys Lys Arg
            180                 185                 190

Lys Val Asp Gly Gly Ala Leu Ser Pro Gln His Ser Ala Val Thr
            195                 200                 205

Gln Gly Ser Ile Ile Lys Asn Lys Glu Gly Met Asp Ala Lys Ser Leu
        210                 215                 220

Thr Ala Trp Ser Arg Thr Leu Val Thr Phe Lys Asp Val Phe Val Asp
225                 230                 235                 240

Phe Thr Arg Glu Glu Trp Lys Leu Leu Asp Thr Ala Gln Gln Ile Val
            245                 250                 255

Tyr Arg Asn Val Met Leu Glu Asn Tyr Lys Asn Leu Val Ser Leu Gly
            260                 265                 270

Tyr Gln Leu Thr Lys Pro Asp Val Ile Leu Arg Leu Glu Lys Gly Glu
            275                 280                 285

Glu Pro Trp Leu Val Glu Arg Glu Ile His Gln Glu Thr His Pro Asp
```

```
            290                 295                 300
Ser Glu Thr Ala Phe Glu Ile Lys Ser Ser Val Glu Gln Lys Leu Ile
305                 310                 315                 320

Ser Glu Glu Asp Leu
                325
```

<210> SEQ ID NO 98
<211> LENGTH: 328
<212> TYPE: PRT
<213> ORGANISM: Artificial
<220> FEATURE:
<223> OTHER INFORMATION: Six Finger Domain Protein and Repressor

<400> SEQUENCE: 98

```
Met Ala Glu Arg Pro Tyr Ala Cys Pro Val Glu Ser Cys Asp Arg Arg
1               5                   10                  15

Phe Ser Arg Ser Asp Glu Leu Thr Arg His Ile Arg Ile His Thr Gly
                20                  25                  30

Gln Lys Pro Phe Gln Cys Arg Ile Cys Met Arg Asn Phe Ser Arg Ser
            35                  40                  45

Asp Asn Leu Ser Glu His Ile Arg Thr His Thr Gly Glu Lys Pro Phe
50                  55                  60

Ala Cys Asp Ile Cys Gly Arg Lys Phe Ala Arg Ser Asp Asn Arg Lys
65                  70                  75                  80

Thr His Thr Lys Ile His Thr Gly Gly Gly Ser Gly Gly Ser Glu
                85                  90                  95

Arg Pro Tyr Ala Cys Pro Val Glu Ser Cys Asp Arg Arg Phe Ser Asp
                100                 105                 110

Asn Arg Asp Leu Ile Arg His Ile Arg Ile His Thr Gly Gln Lys Pro
            115                 120                 125

Phe Gln Cys Arg Ile Cys Met Arg Asn Phe Ser Arg Ser Asp Asp Leu
        130                 135                 140

Ser Arg His Ile Arg Thr His Thr Gly Glu Lys Pro Phe Ala Cys Asp
145                 150                 155                 160

Ile Cys Gly Arg Lys Phe Ala Arg Ser Asp Asn Arg Thr Lys His Thr
                165                 170                 175

Lys Ile His Leu Arg Gln Lys Asp Ala Ala Arg Asn Ser Gly Pro Lys
                180                 185                 190

Lys Lys Arg Lys Val Asp Gly Gly Ala Leu Ser Pro Gln His Ser
            195                 200                 205

Ala Val Thr Gln Gly Ser Ile Ile Lys Asn Lys Glu Gly Met Asp Ala
                210                 215                 220

Lys Ser Leu Thr Ala Trp Ser Arg Thr Leu Val Thr Phe Lys Asp Val
225                 230                 235                 240

Phe Val Asp Phe Thr Arg Glu Glu Trp Lys Leu Leu Asp Thr Ala Gln
                245                 250                 255

Gln Ile Val Tyr Arg Asn Val Met Leu Glu Asn Tyr Lys Asn Leu Val
            260                 265                 270

Ser Leu Gly Tyr Gln Leu Thr Lys Pro Asp Val Ile Leu Arg Leu Glu
        275                 280                 285

Lys Gly Glu Glu Pro Trp Leu Val Glu Arg Ile His Gln Glu Thr
            290                 295                 300

His Pro Asp Ser Glu Thr Ala Phe Glu Ile Lys Ser Ser Val Glu Gln
305                 310                 315                 320

Lys Leu Ile Ser Glu Glu Asp Leu
                325
```

<210> SEQ ID NO 99
<211> LENGTH: 24
<212> TYPE: DNA
<213> ORGANISM: Artificial
<220> FEATURE:
<223> OTHER INFORMATION: 5' Primer

<400> SEQUENCE: 99
gcagagctct ctggctaact agag        24

<210> SEQ ID NO 100
<211> LENGTH: 9
<212> TYPE: PRT
<213> ORGANISM: Artificial
<220> FEATURE:
<223> OTHER INFORMATION: Antibody Epitope Tag

<400> SEQUENCE: 100

Tyr Pro Tyr Asp Val Pro Asp Tyr Ala
1               5

<210> SEQ ID NO 101
<211> LENGTH: 21
<212> TYPE: DNA
<213> ORGANISM: Homo sapiens

<400> SEQUENCE: 101
ccagcggcgc atgcgccgcg c        21

<210> SEQ ID NO 102
<211> LENGTH: 21
<212> TYPE: DNA
<213> ORGANISM: Artificial
<220> FEATURE:
<223> OTHER INFORMATION: Mutated Target Site

<400> SEQUENCE: 102
ccaatagcgc atgcgccgcg c        21

<210> SEQ ID NO 103
<211> LENGTH: 21
<212> TYPE: DNA
<213> ORGANISM: Artificial
<220> FEATURE:
<223> OTHER INFORMATION: Mutated Target Site

<400> SEQUENCE: 103
ccagcgatac atgcgccgcg c        21

<210> SEQ ID NO 104
<211> LENGTH: 21
<212> TYPE: DNA
<213> ORGANISM: Artificial
<220> FEATURE:
<223> OTHER INFORMATION: Mutated Target Site

<400> SEQUENCE: 104
ccaataatac atgcgccgcg c        21

<210> SEQ ID NO 105
<211> LENGTH: 21
<212> TYPE: DNA
<213> ORGANISM: Homo sapiens

<400> SEQUENCE: 105

```
ccagcgatac ataccgcg c                                              21

<210> SEQ ID NO 106
<211> LENGTH: 21
<212> TYPE: DNA
<213> ORGANISM: Artificial
<220> FEATURE:
<223> OTHER INFORMATION: Mutated Target Site

<400> SEQUENCE: 106
ccaataatac ataccgcg c                                              21

<210> SEQ ID NO 107
<211> LENGTH: 29
<212> TYPE: DNA
<213> ORGANISM: Homo sapiens

<400> SEQUENCE: 107
ccagcggcgc atgcgccgcg ctcggagcg                                    29

<210> SEQ ID NO 108
<211> LENGTH: 29
<212> TYPE: DNA
<213> ORGANISM: Artificial
<220> FEATURE:
<223> OTHER INFORMATION: Mutated Target Site

<400> SEQUENCE: 108
ggaggaggag gccacaggag gcgggagga                                    29

<210> SEQ ID NO 109
<211> LENGTH: 23
<212> TYPE: DNA
<213> ORGANISM: Homo sapiens

<400> SEQUENCE: 109
gcgcatgcgc cgcgctcgga gcg                                          23

<210> SEQ ID NO 110
<211> LENGTH: 29
<212> TYPE: DNA
<213> ORGANISM: Artificial
<220> FEATURE:
<223> OTHER INFORMATION: Mutated Target Site

<400> SEQUENCE: 110
ggaggaggag gccacaggag gcgggagga                                    29

<210> SEQ ID NO 111
<211> LENGTH: 30
<212> TYPE: DNA
<213> ORGANISM: Homo sapiens

<400> SEQUENCE: 111
gtcggattgg tgggttgggg gcacaaggca                                   30

<210> SEQ ID NO 112
<211> LENGTH: 30
<212> TYPE: DNA
<213> ORGANISM: Homo sapiens

<400> SEQUENCE: 112
tggaggagga ggccacagga ggcgggagga                                   30

<210> SEQ ID NO 113
```

```
<211> LENGTH: 30
<212> TYPE: DNA
<213> ORGANISM: Homo sapiens

<400> SEQUENCE: 113
caggaagagc tggaggagga ggccacagga                                              30

<210> SEQ ID NO 114
<211> LENGTH: 31
<212> TYPE: PRT
<213> ORGANISM: artificial
<220> FEATURE:
<223> OTHER INFORMATION: Zinc Finger Motif
<220> FEATURE:
<221> NAME/KEY: MISC_FEATURE
<222> LOCATION: (1)..(2)
<223> OTHER INFORMATION: Xaa = any amino acid
      Xaa can be present or absent
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
      Xaa can be present or absent
<220> FEATURE:
<221> NAME/KEY: MISC_FEATURE
<222> LOCATION: (10)..(18)
<223> OTHER INFORMATION: Xaa = any amino acid
<220> FEATURE:
<221> NAME/KEY: MISC_FEATURE
<222> LOCATION: (19)..(23)
<223> OTHER INFORMATION: Xaa = any amino acid
      Xaa can be present or absent
<220> FEATURE:
<221> NAME/KEY: MISC_FEATURE
<222> LOCATION: (25)..(27)
<223> OTHER INFORMATION: Xaa = any amino acid
<220> FEATURE:
<221> NAME/KEY: MISC_FEATURE
<222> LOCATION: (28)..(30)
<223> OTHER INFORMATION: Xaa = any amino acid
      Xaa can be present or absent
<220> FEATURE:
<221> NAME/KEY: MISC_FEATURE
<222> LOCATION: (31)..(31)
<223> OTHER INFORMATION: Xaa = His or Cys

<400> SEQUENCE: 114

Xaa Xaa Cys Xaa Xaa Xaa Xaa Xaa Cys Xaa Xaa Xaa Xaa Xaa Xaa
1               5                   10                  15

Xaa Xaa Xaa Xaa Xaa Xaa Xaa His Xaa Xaa Xaa Xaa Xaa Xaa Xaa
            20                  25                  30

<210> SEQ ID NO 115
<211> LENGTH: 31
<212> TYPE: PRT
<213> ORGANISM: artificial
<220> FEATURE:
<223> OTHER INFORMATION: Zinc Finger Motif
<220> FEATURE:
<221> NAME/KEY: MISC_FEATURE
<222> LOCATION: (1)..(2)
<223> OTHER INFORMATION: Xaa = any amino acid
      Xaa can be present or absent
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
```

```
       Xaa can be present or absent
<220> FEATURE:
<221> NAME/KEY: MISC_FEATURE
<222> LOCATION: (10)..(11)
<223> OTHER INFORMATION: Xaa = any amino acid
<220> FEATURE:
<221> NAME/KEY: MISC_FEATURE
<222> LOCATION: (12)..(16)
<223> OTHER INFORMATION: Xaa = any amino acid
       Xaa can be present or absent
<220> FEATURE:
<221> NAME/KEY: MISC_FEATURE
<222> LOCATION: (17)..(23)
<223> OTHER INFORMATION: Xaa = any amino acid
<220> FEATURE:
<221> NAME/KEY: MISC_FEATURE
<222> LOCATION: (25)..(27)
<223> OTHER INFORMATION: Xaa = any amino acid
<220> FEATURE:
<221> NAME/KEY: MISC_FEATURE
<222> LOCATION: (28)..(30)
<223> OTHER INFORMATION: Xaa = any amino acid
       Xaa can be present or absent
<220> FEATURE:
<221> NAME/KEY: MISC_FEATURE
<222> LOCATION: (31)..(31)
<223> OTHER INFORMATION: Xaa = His or Cys

<400> SEQUENCE: 115

Xaa Xaa Cys Xaa Xaa Xaa Xaa Xaa Cys Xaa Xaa Xaa Xaa Xaa Xaa Xaa
1               5                   10                  15

Xaa Xaa Xaa Xaa Xaa Xaa Xaa His Xaa Xaa Xaa Xaa Xaa Xaa Xaa
            20                  25                  30

<210> SEQ ID NO 116
<211> LENGTH: 25
<212> TYPE: PRT
<213> ORGANISM: artificial
<220> FEATURE:
<223> OTHER INFORMATION: Zinc Finger Motif
<220> FEATURE:
<221> NAME/KEY: MISC_FEATURE
<222> LOCATION: (1)..(2)
<220> FEATURE:
<221> NAME/KEY: MISC_FEATURE
<222> LOCATION: (1)..(2)
<223> OTHER INFORMATION: Xaa = any amino acid
       Xaa can be present or absent
<220> FEATURE:
<221> NAME/KEY: MISC_FEATURE
<222> LOCATION: (4)..(4)
<223> OTHER INFORMATION: Xaa = any amino acid (S, E, K, T, P, and R are
       preferred)
<220> FEATURE:
<221> NAME/KEY: MISC_FEATURE
<222> LOCATION: (5)..(5)
<223> OTHER INFORMATION: Xaa = any amino acid (E is preferred)
<220> FEATURE:
<221> NAME/KEY: MISC_FEATURE
<222> LOCATION: (6)..(7)
<223> OTHER INFORMATION: Xaa = any amino acid
       Xaa can be present or absent
<220> FEATURE:
<221> NAME/KEY: MISC_FEATURE
<222> LOCATION: (9)..(9)
<223> OTHER INFORMATION: Xaa = any amino acid (G is preferred)
<220> FEATURE:
<221> NAME/KEY: MISC_FEATURE
<222> LOCATION: (10)..(10)
<223> OTHER INFORMATION: Xaa = any amino acid (K is preferred)
<220> FEATURE:
<221> NAME/KEY: MISC_FEATURE
<222> LOCATION: (11)..(11)
<223> OTHER INFORMATION: Xaa = any amino acid (A, C, S, G are preferred)
       Xaa can be present or absent
<220> FEATURE:
<221> NAME/KEY: MISC_FEATURE
```

-continued

```
<222> LOCATION: (13)..(13)
<223> OTHER INFORMATION: Xaa = any amino acid (S and T are preferred)
<220> FEATURE:
<221> NAME/KEY: MISC_FEATURE
<222> LOCATION: (14)..(17)
<223> OTHER INFORMATION: Xaa = any amino acid
<220> FEATURE:
<221> NAME/KEY: MISC_FEATURE
<222> LOCATION: (19)..(20)
<223> OTHER INFORMATION: Xaa = any amino acid
<220> FEATURE:
<221> NAME/KEY: MISC_FEATURE
<222> LOCATION: (22)..(23)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = any amino acid (T or I are preferred)

<400> SEQUENCE: 116

Xaa Xaa Cys Xaa Xaa Xaa Xaa Cys Xaa Xaa Xaa Phe Xaa Xaa Xaa Xaa
1               5                   10                  15

Xaa Leu Xaa Xaa His Xaa Xaa Xaa His
            20                  25

<210> SEQ ID NO 117
<211> LENGTH: 21
<212> TYPE: DNA
<213> ORGANISM: Artificial
<220> FEATURE:
<223> OTHER INFORMATION: TNFR 1-7-9 Target Sequence

<400> SEQUENCE: 117
ccgcctcctg tggcctcctc c                                           21

<210> SEQ ID NO 118
<211> LENGTH: 22
<212> TYPE: DNA
<213> ORGANISM: Artificial
<220> FEATURE:
<223> OTHER INFORMATION: TNFR 1-9-12 Target Sequence

<400> SEQUENCE: 118
gtggcctcct cctccagctc tt                                          22

<210> SEQ ID NO 119
<211> LENGTH: 21
<212> TYPE: DNA
<213> ORGANISM: Artificial
<220> FEATURE:
<223> OTHER INFORMATION: TNFR 1-7-10 Target Sequence

<400> SEQUENCE: 119
ccgcctcctg tggcctcctc c                                           21

<210> SEQ ID NO 120
<211> LENGTH: 6
<212> TYPE: PRT
<213> ORGANISM: Artificial
<220> FEATURE:
<223> OTHER INFORMATION: Linker Sequence

<400> SEQUENCE: 120

Thr Gly Ser Glu Arg Pro
1               5

<210> SEQ ID NO 121
<211> LENGTH: 9
<212> TYPE: PRT
```

```
<213> ORGANISM: Artificial
<220> FEATURE:
<223> OTHER INFORMATION: Linker Sequence

<400> SEQUENCE: 121

Thr Gly Gly Gly Gly Ser Glu Arg Pro
1               5

<210> SEQ ID NO 122
<211> LENGTH: 12
<212> TYPE: PRT
<213> ORGANISM: artificial
<220> FEATURE:
<223> OTHER INFORMATION: Linker Sequence

<400> SEQUENCE: 122

Thr Gly Gly Gly Gly Ser Gly Gly Ser Glu Arg Pro
1               5                   10

<210> SEQ ID NO 123
<211> LENGTH: 22
<212> TYPE: PRT
<213> ORGANISM: artificial
<220> FEATURE:
<223> OTHER INFORMATION: Linker Sequence

<400> SEQUENCE: 123

Gly Gly Ala Thr Thr Gly Gly Thr Gly Gly Gly Thr Thr Gly Gly Gly
1               5                   10                  15

Gly Gly Cys Ala Cys Ala
                20
```

MODULATION OF HIV INFECTION

FIELD OF THE INVENTION

The present invention relates to molecules. In particular, the present invention relates to molecules capable of binding to receptor nucleotide sequences.

BACKGROUND OF THE INVENTION

Many diseases are caused by viral infections. Infection of humans with Human Immunodeficiency Virus such as HIV-1 causes a dramatic decline in the numbers of white blood cells, particularly in the numbers of CD4+ T-lymphocytes. When the number of such cells becomes low enough, opportunistic infections and neoplasms occur, and the pathology may progress to Acquired Immune Deficiency Syndrome (AIDS). Therapeutics aimed at combating HIV and other viruses, as well as research tools for their study, are extremely important.

Many viruses subvert host proteins to gain entry into cells, exploit their metabolic functions for replication, and evade immune surveillance. Furthermore, immune reactions that may be beneficial for clearing pathogens can be deleterious to the host if they persist or if they are triggered inappropriately, such as in autoimmune syndromes.

The present invention seeks to overcome one or more problem(s) associated with the prior art.

SUMMARY OF THE INVENTION

According to one aspect of the present invention, we provide a polypeptide capable of binding to a nucleic acid comprising a receptor nucleotide sequence.

Other aspects of the invention are set out below as independent claims. Preferred aspects of the invention are as set out in the subclaims, and also in the description below.

BRIEF DESCRIPTION OF THE DRAWINGS

FIGS. 1A, 1B and 1C show DNA-binding by the six-finger CXCR4 constructs using an in vitro (TNT) fluorescence ELISA assay. FIG. 1A. Binding of the six-zinc finger peptide, CXCR4-5-1, to its preferred target site and to 5 control sites containing base mutations (underlined). FIG. 1B. Binding of the six-zinc finger peptide, CXCR4-10-1, to its preferred target site and to a control site containing base mutations (underlined). FIG. 1C. Binding of the six-zinc finger peptide, CXCR4-10-3, to its preferred target site and to a control site containing base mutations (underlined).

FIG. 2A. Expression of CXCR4 at the surface of Jurkat cells. FIG. 2B. Expression of CXCR4 as assessed by FACS analysis on different population: non-transfected Jurkat cells which represent an internal control (R1) and sub populations R2, R3 and R4 exhibit 10, 100- and 1000-fold higher GFP fluorescence intensity relative to background, respectively. FIG. 2C. Down-regulation of CXCR4 observed with Jurkat cells transfected with zinc finger proteins 10-1 and 10-3.

FIG. 3A. Binding of TNFR1-4-2 to its preferred target, a control site, and no binding site (nbs). FIG. 3B. Binding of the six-zinc finger peptide TNFR1-7-9 to its preferred target, an overlapping site, a control site, and no binding site. FIG. 3C. Binding of the six-zinc finger peptide TNFR1-9-12 to its preferred target, an overlapping site, a control site, and no binding site. Sequences of target sites 4-2, 7-9 and 9-12 are shown under FIG. 3A. The target sites of TNFR1-9-12 and TNFR1-7-9 overlap over a distance corresponding to 4½ of the 6 fingers binding region.

FIG. 4A. Expression of TNFR1 on Jurkat T cells is indicated by the filled area, while the open area represents a negative staining control. FIG. 4B. Expression of TNFR1 after transient transfection with expression vectors encoding GFP only (pTracer, Invitrogen), or GFP and four different zinc finger proteins targetted at the TNFR1 promoter. An expression vector encoding the CXCR4 zinc finger protein used in FIGS. 2A,B is used as a control. The left panel depicts GFP fluorescence, which serves to identify transfected cells. Electronic gates are applied for GFP+ transfected cells (G1). The second panel shows TNFR1 expression on the total cell population. TNFR1 expression on the G1, GFP+ subpopulation is depicted in the third panel.

FIG. 6 shows the specific down-regulation of TNFR-1 and CXCR4 by TNFR1-4-2-Kox and CXCR4-5-1-Kox, respectively. Column 1, total cell population, with proportion of cells expressing GFP from the transfected plasmid indicated under the horizontal line; column 2, expression levels of TNFR-1 in cells also expressing GFP; column 3, expression levels of CXCR4 in cells also expressing GFP; column 4, expression levels of ICAM in cells also expressing GFP. Data in rows A, B, C and D is for cells transfected with empty pTracer vector, pTracer containing TNFR1-4-2-Kox; pTracer containing CXCR4-5-1-Kox; and both TNFR1-4-2-Kox and CXCR4-5-1-Kox-containing vectors, respectively.

DETAILED DESCRIPTION OF THE INVENTION

Figure 1A:
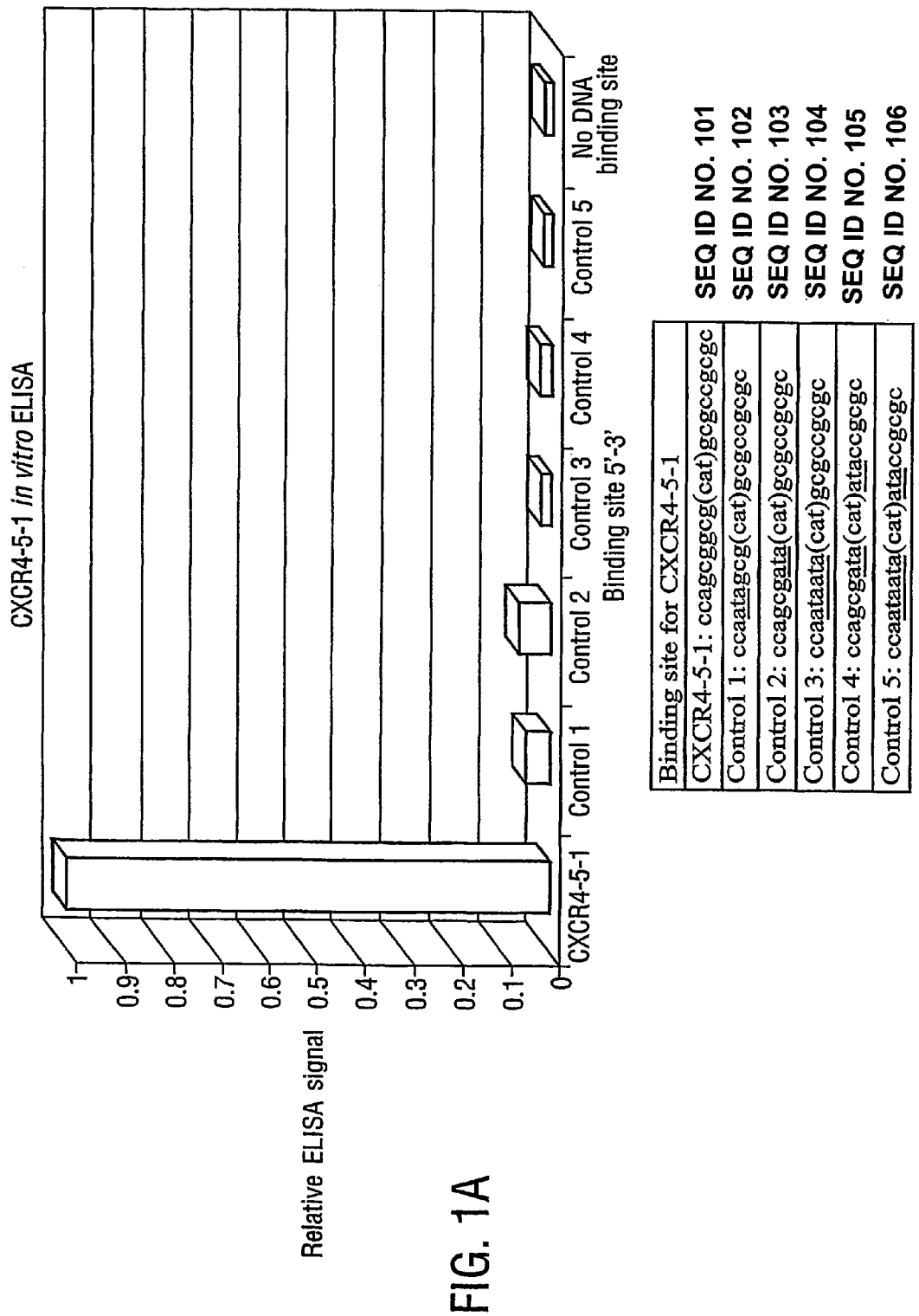

In general, the invention provides a polypeptide capable of binding to a nucleic acid comprising a receptor nucleotide sequence.

Polypeptides according to preferred embodiments of the invention include those which are capable of binding to receptor nucleotide sequences, in which the receptor is involved in any aspect of viral function, for example, viral binding, viral infection, etc. Such a viral receptor may be capable of mediating or facilitating etc the viral function. The receptor may be involved in viral infection of any kind, including HIV infection, for example, CD4, CXCR4, CCR5, CCR3 or CCR2b.

Furthermore, the invention includes polypeptides capable of binding receptor nucleotide sequences in which the receptor is capable of binding to one or more other molecules ("ligands"). Such a receptor may be involved in any form of signal transduction, and may in particular be involved in an immune reaction (whether appropriate or inappropriate) against any agent, including pathogens or other insults. It will be appreciated that receptors may have plural activities or functions, such that the above preferred embodiments are not to be considered mutually exclusive.

In a further preferred embodiment of the invention, the receptor is involved in transmitting signals upon binding of a ligand. Such a ligand may include proteins, or other chemical compounds that can act as agonists or antagonists of such molecules. Preferably, the receptor is involved in regulation of the immune system, preferably TNFR1 and other members of the TNF receptor family (TNFR2, Fas/Apo-1/CD95, lymphotoxin beta receptor, TRAIL receptor, osteoprotegerin, RANK), the IL-1 and IL-18 receptors, and the receptors for Type I and II Interferons.

Nucleic acid binding polypeptides according to the invention preferably comprise zinc finger polypeptides. Preferably, the nucleic acid binding polypeptide is capable of downregulating a receptor, preferably capable of transcriptional downregulation of a receptor. Highly preferred embodiments include zinc finger polypeptides selected from the group consisting of consensus sequences 1 to 18 (see Table 1), a variant of one or more thereof, and polypeptides comprising combinations of two or more thereof.

Preferred zinc fingers include those comprising three fingers, i.e., selected from the group consisting of zinc fingers comprising consensus sequences 1 to 3, zinc fingers comprising consensus sequences 4 to 6, zinc fingers comprising consensus sequences 7 to 9, zinc fingers comprising consensus sequences 10 to 12, zinc fingers comprising consensus sequences 13 to 15, and zinc fingers comprising consensus sequences 16 to 18 (see Table 1). Preferably, the zinc finger polypeptides comprise six zinc fingers, viz, zinc fingers comprising consensus sequences 1 to 6, consensus sequences 7 to 12 or consensus sequences 13 to 18 (see Table 1). In each of these cases, the individual finger modules may be linked by canonical, structured or flexible linkers (as described in further detail below), preferably, linkers comprising GERP, GGGGSGGSGGSERP or GGGGSGGSGGSGGSGGSERP. The nucleic acid binding polypeptides may further comprise one or more repressor domains, preferably, a KOX domain, as described below.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

Receptor

The term "receptor" as used in the present document is intended to refer to a molecule which is capable of binding to another molecule (the ligand). Preferably, the receptor is located in the plasma membrane of a cell (a cell surface receptor). More preferably, the receptor is a transmembrane receptor. The receptor may be a chemokine receptor or a cytokine receptor. Most preferably, the receptor is a G-protein coupled receptor. The receptor may be involved in the regulation (repression or activation) of a downstream a transcription factor. Such a transcription factor may for example include members of the NF-kB or STAT families of transcription factors. Transmembrane receptors, including G-protein coupled and cytokine receptors, their properties and sequences, are known in the art.

Binding of the ligand to the receptor may lead to the activation of one or more biological activities, such as a post-transcriptional modification (for example, phosphorylation), dimerisation, nuclear (or other subcellular) localisation, binding to a third molecule, etc.

In one aspect of the invention, a nucleic acid binding polypeptide is capable of binding to a nucleic acid comprising a nucleotide sequence of a receptor involved in a viral function. The viral function is preferably selected from the group consisting of: viral titre, viral infectivity, viral replication, viral packaging, viral transcription, viral entry, viral attachment and viral penetration. Most preferably, the receptor is involved in viral infection.

A single receptor appears to be necessary and sufficient for entry of many retroviruses, but there exist exceptions to this simple model. For example, HIV requires two proteins for cell entry, neither of which alone is sufficient; 10A1 murine leukemia virus can enter cells by using either of two distinct receptors; two retroviruses can use different receptors in some cells but use the same receptor for entry into other cells. The term "co-receptor" is used here to refer any one of two or more polypeptides which contribute to, or are necessary for, cellular entry of the virus. The invention thus encompasses use of one or more nucleic acid binding polypeptides capable of binding nucleic acid sequences comprising a co-receptor, where more than one receptor is necessary and/or sufficient for viral entry into the cell. As will be appreciated, two or more such nucleic acid binding polypeptides may be used, each one capable of targeting one or more co-receptors. For example, a nucleic acid binding polypeptide capable of targeting CD4 may be used in conjunction with a nucleic acid binding polypeptide capable of targeting CXCR4. The term "receptor" where the context admits includes reference to a "co-receptor".

Preferably, the receptor is capable of binding a ligand which is a viral protein, preferably a viral envelope protein. Preferably, binding of the receptor to the viral protein is involved in, results in, or leads to, infection of a cell with the virus. Preferably, the receptor is capable of binding a polypeptide ligand of a lentivirus, preferably Human Immunodeficiency Virus, preferably, HIV-1. Most preferably, the polypeptide ligand is a gp120 protein of HIV.

Preferably, the receptor is involved in infection by HW, for example, CD4, CXCR4, CCR5, CCR3, CCR2b, etc. In a highly preferred embodiment of the invention, the receptor is a CXCR4 receptor, as discussed in further detail below. Preferably, the nucleic acid binding polypeptide comprises a zinc finger polypeptide capable of binding to a CXCR4 receptor promoter sequence. Preferably, the CXCR4 receptor promoter sequence comprises a sequence selected from the group consisting of: 5'-Tccccgccccagcggcgcatgcgc-cgcgctcggagcgtgtttttata-3', 5'-CCGCCCCAGCGGCGCAT-GCGCCGCGCTCGGAGCGTGTT-3' (CXCR4-5-1, SEQ ID NO:4), 5'-CCGCCCCAGCGGCGCATGCGC-CGCGCTCGGAGCGTGTT-3' (CXCR4-10-1, SEQ ID NO:5), and 5'-CCGCCCCAGCGGCGCATGCGC-CGCGCTCGGAGCGTGTT-3' (CXCR4-10-3, SEQ ID NO:6).

In another aspect of the invention, the receptor is involved in regulation of a biological function. Preferably, the receptor is capable of binding a ligand which is either diffusible in bodily fluids, or integrated into or bound covalently or non-covalently to cell membranes or viral envelopes, the extracellular matrix, or any other substrate. Preferably, binding of the receptor to ligand is involved in, results in, or leads to, metabolic responses of a cell to the ligand. Preferably, the receptor is capable of binding a polypeptide ligand associated with an immune response, typically classified as cytokines or interleukins.

The biological function which is capable of being regulated by the receptor may include an immune function, for example, an immune response. The immune function is preferably associated with activation of cells associated with the immune system. Such cells may include B, T, NK, macrophages, neutrophils, and other lymphoid and myeloid cell types. The receptor may also be involved in any of the various metabolic responses of cells in the body to molecules in the circulation. Such molecules may be expressed and/or released by a variety of cell types, for example, lymphoid, myeloid, or stromal cells in response, to an immune stimulus. The receptor may in particular be involved in one or more anti-viral responses of the immune system. Preferred receptors include those which are involved in an autoimmune disease.

Preferred receptors of this aspect of the invention include TNFR1, TNFR2, IL-1R, IFN receptors, etc. In a highly preferred embodiment of the invention, the receptor comprises a TNFR1 receptor. Preferably, the nucleic acid binding polypeptide comprises a zinc finger polypeptide capable of binding to a TNFR1 receptor promoter sequence. Preferably, the TNFR1 receptor promoter sequence comprises a sequence selected from the group consisting of: 5'GTCG-GATTGGTGGG TTGGGGGCACAAGGCA-3' (TNFR1-4-2, SEQ ID NO:8); 5'TGGAGGAGGAGGCCACAGGAG-GCGGGAGGA-3' (TNFR1-7-9; TNFR1-7-10, SEQ ID NO:9); 5'CAGGAAGAGCTGGAGGAGGAGGCCCA-CAGGA-3' (TNFR1-9-12, SEQ ID NO:10).

A nucleic acid binding polypeptide according to the invention is preferably capable of down-regulating the receptor. The receptor may be down-regulated by a number of ways, including down-regulation of DNA replication of a sequence comprising the receptor, down-regulation of transcription of a gene encoding the receptor, down-regulation of RNA processing of a receptor transcript, down-regulation of transcript RNA turnover, down-regulation of translation, down-regulation of transport and/or intracellular localisation of polypeptide and/or RNA within the cell, down-regulation of post-transcriptional modification, down-regulation of protease or other activity which activates the receptor, down-regulation of receptor cofactors, down-regulation of activity of the receptor, up-regulation of breakdown of the receptor, etc. Accordingly, the invention encompasses any nucleic acid binding polypeptide capable of any of these activities through binding to its target. Preferably, down-regulation of the receptor is achieved through transcriptional regulation, as described below.

A "receptor nucleotide sequence" is intended to refer to any nucleotide sequence comprising, derived from, including or associated with, etc a gene encoding a receptor. In preferred embodiments of the invention, the receptor nucleotide sequence comprises a gene, or a portion of a gene, for the receptor. The receptor nucleotide sequence may comprise a nucleic acid sequence capable of encoding a receptor, or it may comprise any of the control sequences of the receptor gene, for example, a promoter sequence, an enhancer sequence, a transcription factor binding site, a splice site, a sequence controlling transcription termination, etc. What is important is that the sequence is in some way involved in the regulation of expression of the receptor gene. Preferably, binding of the nucleic acid binding polypeptide to its target results in down-regulation of expression of the receptor.

Chemokine Receptors

In a particular embodiment of the invention, we provide a polypeptide capable of binding to a nucleic acid comprising a chemokine nucleotide sequence.

Chemokines are a family of chemoattractive polypeptides, that are classified into 4 groups, depending on the position of conserved cysteine residues. Chemokines attract leukocyte subsets to inflammation sites and/or have homeostatic functions in regulating lymphocyte trafficking between and within lymphoid organs. A review of chemokines and their receptors is provided in Wells T N, Power C A, Proudfoot A E, 1998, *Definition, function and pathophysiological significance of chemokine receptors* Trends Pharmacol Sci 1998 September; 19(9):376-80; Wilkinson D, 1996, Curr Biol 1996 Sep. 1; 6(9):1051-3; Miller A D, 1996, Proc Natl Acad Sci USA 1996 Oct. 15; 93(21):11407-13.

Preferred chemokines and receptors for them according to the invention include the following: C Chemokines such as SCYC1, Lptn, CL1, Lymphotactin, SCM-1a, ATAC, SCYC2, CL2, SCM-1b; CC Chemokines, CXC Chemokines, CXXXC Chemokines and virus-encoded chemokines. In a particularly preferred embodiment of the invention, the receptor is a CXC chemokine receptor. Examples of CXC chemokine receptors include receptors for SCYB1, SCYB2, SCYB3, SCYB4, SCYB4V1, SCYB5, SCYB6, (GCP-2, like, SCYB7, SPBPBP, SCYB8, SCYB9, SCYB10, SCYB11, (SCYB9B), SCYB12, SCYB13, SCYB14, SCYB15, SCYB16, SCYB1P, NAP-4 and LFCA-1.

In particular, the receptor may be chosen from the group consisting of: a CCR3 receptor, a CCR2b receptor, a CCR5 receptor, and a CXCR-4 receptor.

CXCR4 Receptor

In a preferred embodiment of the invention, the receptor is a receptor capable of binding a SDF-1 ligand. Preferably, the receptor is a CXCR4 receptor. Stromal cell-derived factor-1 (SDF-1) is a CXC chemokine that binds to a unique transmembrane G protein-coupled receptor called CXCR4, is chemoattractive for hematopoietic progenitor cells, B lymphocytes, T lymphocytes, and monocytes. SDF-1 has been shown to regulates B lymphopoiesis and myelopoiesis by confining precursors within the supportive bone marrow microenvironment before further maturation. CXCR4 also acts as a co-receptor for the human immunodeficiency virus (HIV)-1 and 2.

The invention therefore relates in a particularly preferred embodiment to a molecule capable of binding to a nucleic acid comprising a CXCR4 receptor sequence, preferably a CXCR4 promoter sequence. Preferably, the molecule is capable of binding to and downregulating the expression of the CXCR4 gene.

CXCR4 (CXC chemokine receptor 4) is a co-receptor for T-cell-tropic HIV-1 strains, known also as X4 viruses (1, 6, reviewed in 7). CXCR4 is a G-protein-coupled, 7-transmembrane domain receptor whose physiological ligand is the Stromal Cell-Derived Factor-1 (SDF-1) chemokine (2, 13). CXCR4 is also known as CMKAR4, LCR1, NPY3R (systematic Human Genome nomenclature), fusin, HM89, LESTR, NPYRL, SDF-1R, D2S201E, CXCR4-Lo.

CXCR4 is expressed in dendritic cells (9), naive, non-memory T-cells (3), neurons and microglia (11), fresh primary monocytes (5, 16), endothelial cells (10, 15), neutrophils and B-cells (8). CXCR4 expression is induced by phytohemagglutinin (PHA) stimulation of peripheral blood mononuclear cells (PBMCs) (3). The first, second and third extracellular domains of CXCR4+ have been implicated in the recognition of CXCR4 by X4 HIV-1 strains. X4 strains differ significantly in their use of CXCR4 extracellular domains (4,12); for example: HIV-1 (NDK) and HIV-2

(ROD) are unable to use CXCR-4 in which most of the amino-terminal domain is deleted, while HIV-1 (LAI) is able to use the truncated receptor (4).

Several compounds with anti-HIV-1 activity are thought to function through disruption of the envelope: CXCR4 interaction: T22, AMD3100, and ALX40-4C. In addition, the CXCR4-specific 12G5 monoclonal antibody has been shown to have anti-HIV-1 activity in-vitro (12), as do the CXCR4 ligands SDF-1 and SDF-1a (2,13). SDF-1 and phorbol 12-myristate 13-acetate (PMA) also cause rapid CXCR4 endocytosis and down modulation, presumably rendering cells less susceptible to infection by X4 viruses (14). Accordingly, the invention comprises a method of treatment or prevention of a viral disease, comprising administering to a patient a polypeptide as described here, together with a molecule capable of disrupting the interaction of a viral envelope protein with a viral receptor.

Patients infected by the human immunodeficiency virus type 1 (HIV-1) exhibit an invariable loss of $CD4^+$ lymphocytes. However, primary isolates of HIV-1 show distinct differences in their biological properties, including differences in replication kinetics, tropism, and syncytium-inducing capacity. Cellular entry of HIV-1 requires binding to both CD4 and to one transmembrane chemokine co-receptors. CXCR-4 has been shown to mediate entry of T cell line-adapted syncytium-inducing (SI) strains of HIV-1 into $CD4^+$ T cells, but does not permit entry of NSI isolates whereas CCR5 has been identified as a coreceptor for macrophage-tropic, nonsyncytium-inducing (NSI) strains of HIV-1.

Isolates of HIV-1 from early in the course of infection predominantly used CCR5. In patients with disease progression, the virus however expanded its co-receptor use to include other chemokine receptor such as CCR3, CCR2b, and CXCR-4. More importantly, the emergence of variants using the CXCR-4 co-receptor is associated with a switch from NSI to SI phenotype, a decreasing $CD4^+$ T cell counts and therefore a progression to AIDS.

A highly preferred embodiment of a polypeptide according to the invention comprises a polypeptide which is capable of binding to a nucleic acid sequence comprising a CXCR4 nucleotide sequence or a nucleotide sequence from a promoter or enhancer of CXCR4. Preferably, the CXCR4 receptor is a human CXCR4 receptor. More preferably, the CXCR4 receptor is the human CXCR4 receptor having GenBank accession number X71635 (Loetscher, M., Geiser, T., O'Reilly, T., Zwahlen, R., Baggiolini, M., and Moser, B. (1994) J. Biol. Chem. 269, 232-237). The sequence of a preferred CXCR4 receptor (GenBank accession number X71635) nucleotide sequence is shown here:

```
                                                          (SEQ ID NO: 11)
   1 ttgcagatat acacttcaga taactacacc gaggaaatgg gctcagggga ctatgactcc 61 atgaaggaac cctgtttccg tgaagaaaat gctaatttca ataaaatctt cctgcccacc 121 atctactcca tcatcttctt aactggcatt gtgggcaatg gattggtcat cctggtcatg 181 ggttaccaga agaaactgag aagcatgacg gacaagtaca ggctgcacct gtcagtggcc 241 gacctcctct ttgtcatcac gcttcccttc tgggcagttg atgccgtggc aaactggtac 301 tttgggaact tcctatgcaa ggcagtccat gtcatctaca cagtcaacct ctacagcagt 361 gtcctcatcc tggccttcat cagtctggac cgctacctgg ccatcgtcca cgccaccaac 421 agtcagaggc caaggaagct gttggctgaa aaggtggtct atgttggcgt ctggatccct 481 gccctcctgc tgactattcc cgacttcatc tttgccaacg tcagtgaggc agatgacaga 541 tatatctgtg accgcttcta ccccaatgac ttgtgggtgg ttgtgttcca gtttcagcac 601 atcatggttg gccttatcct gcctggtatt gtcatcctgt cctgctattg cattatcatc 661 tccaagctgt cacactccaa gggccaccag aagcgcaagg ccctcaagac cacagtcatc 721 ctcatcctgg ctttcttcgc ctgttggctg ccttactaca ttgggatcag catcgactcc 781 ttcatcctcc tggaaatcat caagcaaggg tgtgagtttg agaacactgt gcacaagtgg 841 atttccatca ccgaggccct agcttcttc cactgttgtc tgaacccat cctctatgct 901 ttccttggag ccaaatttaa aacctctgcc cagcacgcac tcacctctgt gagcagaggg 961 tccagcctca agatcctctc caaaggaaag cgaggtggac attcatctgt ttccactgag 1021 tctgagtctt caagttttca ctccagctaa cacagatgta aaagacttt ttttatacga 1081 taaataactt ttttttaagt tacacatttt tcagatataa aagactgacc aatattgtac 1141 agtttttatt gcttgttgga tttttgtctt gtgtttcttt agttttgtg aagtttaatt 1201 gacttattta tataaatttt ttttgtttca tattgatgtg tgtctaggca ggacctgtgg 1261 ccaagttctt agttgctgta tgtctcgtgg taggactgta gaaagggaa ctgaacattc 1321 cagagcgtgt agtgaatcac gtaaagctag aaatgatccc cagctgttta tgcatagata 1381 atctctccat tcccgtggaa cgttttcct gttcttaaga cgtgattttg ctgtagaaga
```

```
                                      -continued
1441 tggcacttat aaccaaagcc caaagtggta tagaaatgct ggttttcag ttttcaggag 1501 tgggttgatt tcagcaccta caqtgtacag tcttgtatta agttgttaat aaaagtacat 1561 gttaaactta cttagtgtta tg
```

Preferably, the nucleotide sequence is chosen from the non-coding upstream region of the CXCR4 gene, for example, positions 1 to 68 of the above sequence.

Virus

In highly preferred embodiments, nucleic acid binding polypeptides of the present invention are capable of binding to nucleotide sequences of receptors or co-receptors involved in viral infection, preferably leading to their downregulation. Thus, they are capable of reducing, preventing, or alleviating the spread of infection of a number of viruses, and may hence be used for treating or preventing diseases associated with or caused by such viruses.

The virus may be an RNA virus or a DNA virus. Preferably, the virus is an integrating virus. Preferably, the virus is selected from a lentivirus and a herpesvirus. More preferably, the virus is an HIV virus or a HSV virus. The methods described here can therefore be used to prevent the development and establishment of diseases caused by or associated with any of the above viruses, including human immunodeficiency virus, such as HIV-1 and HIV-2, and herpesvirus, for example HSV-1, HSV-2, HSV-7 and HSV-8, as well as human cytomegalovirus, varicella-zoster virus, Epstein-Barr virus and human herpesvirus 6. in humans.

Examples of viruses which may be targeted using the present invention are given in the tables below.

| Family | Genus or [Subfamily] | Example | Diseases |
|---|---|---|---|
| DNA VIRUSES | | | |
| Herpesviridae | [Alphaherpesvirinae] | Herpes simplex virus type 1 (aka HHV-1) | Encephalitis, cold sores, gingivostomatitis |
| | | Herpes simplex virus type 2 (aka HHV-2) | Genital herpes, encephalitis |
| | | Varicella zoster virus (aka HHV-3) | Chickenpox, shingles |
| | [Gammaherpesvirinae] | Epstein Barr virus (aka HHV-4) | Mononucleoisis, hepatitis, tumors (BL, NPC) |
| | | Kaposi's sarcoma associated herpesvirus, KSHV (aka Human herpesvirus 8) | ?Probably: tumors, inc. Kaposi's sarcoma (KS) and some B cell lymphomas |
| | [Betaherpesvirinae] | Human cytomegalovirus (aka HHV-5) | Mononucleosis, hepatitis, pneumonitis, congenital |
| | | Human herpesvirus 6 | Roseola (aka *E. subitum*), pneumonitis |
| Adenoviridae | | Human herpesvirus 7 | Some cases of roseola? |
| Papovaviridae | Mastadenovirus | Human adenoviruses | 50 serotypes (species); respiratory infections |
| | Papillomavirus | Human papillomaviruses | 80 species; warts and tumors |
| Hepadnaviridae | Polyomavirus | JC, BK viruses | Mild usually; JC causes PML in AIDS |
| Poxviridae | Orthohepadnavirus | Hepatitis B virus (HBV) | Hepatitis (chronic), cirrhosis, liver tumors |
| | | Hepatitis C virus (HCV) | Hepatitis (chronic), cirrhosis, liver tumors |
| | Orthopoxvirus | Vaccinia virus | Smallpox vaccine virus |
| | | Monkeypox virus | Smallpox-like disease; a rare zoonosis (recent outbreak in Congo; 92 cases from 2/96-2/97) |
| Parvoviridae | Parapoxvirus | Orf virus | Skin lesions ("pocks") |
| | Erythrovirus | B19 parvovirus | *E. infectiousum* (aka Fifth disease), aplastic crisis, fetal loss |
| Circoviridae | Dependovirus | Adeno-associated virus | Useful for gene therapy; integrates into chromosome |
| | Circovirus | TT virus (TTV) | Linked to hepatitis of unknown etiology |
| RNA VIRUSES | | | |
| Picornaviridae | Enterovirus | Polioviruses | 3 types; Aseptic meningitis, paralytic poliomyelitis |
| | | Echoviruses | 30 types; Aseptic meningitis, rashes |
| | | Coxsackieviruses | 30 types; Aseptic meningitis, myopericarditis |
| | Hepatovirus | Hepatitis A virus | Acute hepatitis (fecal-oral spread) |
| | Rhinovirus | Human rhinoviruses | 115 types; Common cold |
| Caliciviridae | Calicivirus | Norwalk virus | Gastrointestinal illness |
| Paramyxoviridae | Paramyxovirus | Parainfluenza viruses | 4 types; Common cold, bronchiolitis, pneumonia |
| | Rubulavirus | Mumps virus | Mumps: parotitis, aseptic meningitis (rare: orchitis, encephalitis) |
| | Morbillivirus | Measles virus | Measles: fever, rash (rare: encephalitis, SSPE) |
| | Pneumovirus | Respiratory syncytial virus | Common cold (adults), bronchiolitis, pneumonia (infants) |
| Orthomyxoviridae | Influenzavirus A | Influenza virus A | Flu: fever, myalgia, malaise, cough, pneumonia |
| | Influenzavirus B | Influenza virus B | Flu: fever, myalgia, malaise, cough, pneumonia |

-continued

| Family | Genus or [Subfamily] | Example | Diseases |
|---|---|---|---|
| Rhabdoviridae | Lyssavirus | Rabies virus | Rabies: long incubation, then CNS disease, death |
| Filoviridae | Filovirus | Ebola and Marburg viruses | Hemorrhagic fever, death |
| Bornaviridae | Bornavirus | Borna disease virus | Uncertain; linked to schizophrenia-like disease in some animals |
| Retroviridae | Deltaretrovirus | Human T-lymphotropic virus type-1 | Adult T-cell leukemia (ATL), tropical spastic paraparesis (TSP) |
| | Spumavirus | Human foamy viruses | No disease known |
| | Lentivirus | Human immunodeficiency virus type-1 and -2 | AIDS, CNS disease |
| Togaviridae | Rubivirus | Rubella virus | Mild exanthem; congenital fetal defects |
| | Alphavirus | Equine encephalitis viruses (WEE, EEE, VEE) | Mosquito-born, encephalitis |
| Flaviviridae | Flavivirus | Yellow fever virus | Mosquito-born; fever, hepatitis (yellow fever!) |
| | | Dengue virus | Mosquito-born; hemorrhagic fever |
| | | St. Louis Encephalitis virus | Mosquito-born; encephalitis |
| | Hepacivirus | Hepatitis C virus | Hepatitis (often chronic), liver cancer |
| | | Hepatitis G virus | Hepatitis??? |
| Reoviridae | Rotavirus | Human rotaviruses | Numerous serotypes; Diarrhea |
| | Coltivirus | Colorado Tick Fever virus | Tick-born; fever |
| | Orthoreovirus | Human reoviruses | Minimal disease |
| Bunyaviridae | Hantavirus | Pulmonary Syndrome Hantavirus | Rodent spread; pulmonary illness (can be lethal, "Four Corners" outbreak) |
| | | Hantaan virus | Rodent spread; hemorrhagic fever with renal syndrome |
| | Phlebovirus | Rift Valley Fever virus | Mosquito-born; hemorrhagic fever |
| | Nairovirus | Crimean-Congo Hemorrhagic Fever virus | Mosquito-born; hemorrhagic fever |
| Arenaviridae | Arenavirus | Lymphocytic Choriomeningitis virus | Rodent-born; fever, aseptic meningitis |
| | | Lassa virus | Rodent-born; severe hemorrhagic fever (BL4 agents; also: Machupo, Junin) |
| | Deltavirus | Hepatitis Delta virus | Requires HBV to grow; hepatitis, liver cancer |
| Coronaviridae | Coronavirus | Human coronaviruses | Mild common cold-like illness |
| Astroviridae | Astrovirus | Human astroviruses | Gastroenteritis |
| Unclassified | "Hepatitis E-like viruses" | Hepatitis E virus | Hepatitis (acute); fecal-oral spread |

Receptors and co-receptors involved in viral functions of the above and other viruses, such as infection, are known in the art. For example, receptors for HIV infection include CD4, CCR5, CXCR4, etc. Reference is made to Rojo D, Suetomi K, Navarro J, 1999, Biol Res 1999; 32(4):263-72; D'Souza M P, Cairns J S, Plaeger S F, 2000, JAMA 2000 Jul. 12; 284(2):215-22.

Receptors for Herpes Simplex Virus infection include HveA, HveB and HveC. HveC allows both HSV-1 and -2 to enter skin cells at the site of infection and to spread into ells of the nervous system. In addition to serving as a co-receptor for HSV-1 and -2, this receptor permits entry of other closely related forms of herpesvirus, porcine pseudorabies virus, and bovine herpesvirus, into cells. HveA is a member of the tumor necrosis factor receptor family, while HveB and HveC belong to the immunoglobulin gene superfamily and are closely related to the poliovirus receptor (Pvr). These receptors mediate HSV-1 infection of various cell types, including lymphoid cells (HveA) and neurons (HveC); HveB mediates infection of cells by HSV-2 and by certain alphaherpesviruses of animals, but does allow infection of cells by wild-type HSV-1. Reference is made to Ramos-Kuri J M, 1992, Envelope and membrane glycoproteins of Herpes simplex virus, *Rev Latinoam Microbiol* 1992 January-March; 34(1):23-3: Rajcani J, Vojvodova A, *The role of herpes simplex virus glycoproteins in the virus replication cycle*, Acta Virol 1998 April; 42(2): 103-18. HAVcr-1 is a simian cellular receptor for the hepatitis A virus (HAV).

Methods of identifying receptors for viruses are known in the art, and are disclosed for example in Okuma K, Yanagi Y (1999), *Approach to the identification of virus receptor*, Uirusu 1999 June; 49(1):1-9.

Human Immunodeficiency Virus-1 (HIV-1)

The nucleic acid binding polypeptides of the present invention are capable of binding to nucleic acid sequences capable of encoding Human Immunodeficiency Virus (HIV) receptors and/or co-receptors such as CD4, CXCR4, CCR5, CCR2b, CCR3 etc. We also provide nucleic acid binding polypeptides capable of treating HIV infection. The methods described here can therefore be used to prevent the development and establishment of diseases caused by or associated with human immunodeficiency virus, such as HIV-1 and HIV-2.

Human Immunodeficiency Virus (HIV) is a retrovirus which infects cells of the immune system, most importantly CD4$^+$ T lymphocytes. CD4$^+$ T lymphocytes are important, not only in terms of their direct role in immune function, but also in stimulating normal function in other components of the immune system, including CD8$^+$ T-lymphocytes. These HIV infected cells have their function disturbed by several mechanisms and/or are rapidly killed by viral replication. The end result of chronic HIV infection is gradual depletion of CD4$^+$ T lymphocytes, reduced immune capacity, and ultimately the development of AIDS, leading to death.

HIV infection typically begins when an HIV particle, which contains two copies of the HIV RNA, encounters a cell with a surface molecule CD4. Cells with this molecule are known as CD4 positive (CD4+) cells. One or more of the virus's gp120 molecules binds tightly to CD4 molecule(s) on the cell's surface. The membranes of the virus and the cell fuse, a process that probably involves both gp41 and a second "fusion cofactor" molecule on the cell surface. Following fusion, the virus's RNA, proteins and enzymes are released into the cell. Although CD4+ T cells appear to be HIV's main target, other immune system cells with CD4 molecules on their surfaces are infected as well. Among these are long-lived cells called monocytes and macrophages, which apparently can harbor large quantities of the virus without being killed, thus acting as reservoirs of HIV. HIV may also may infect cells without CD4 on their surfaces, using other docking molecules. For example, cells of the central nervous system may be infected via a receptor known as galactosyl ceramide. The use of such receptors as targets is also encompassed by the present invention. Cell-to-cell spread of HIV also can occur through the CD4-mediated fusion of an infected cell with an uninfected cell.

Cytokine Receptors

In a particular embodiment of the invention, we provide a polypeptide capable of binding to a nucleic acid comprising a cytokine receptor nucleotide sequence.

Cytokines are polypeptides, typically but not exclusively produced by cells involved in the immune system, and for the purposes of this invention include those referred to as lymphokines, monokines, interleukins, and interferons. They are a diverse group of proteins, although sub-groups can be identified by virtue of sequence or structural homologies. The cellular responses elicited by the interaction of cytokines with their cognate receptors are also diverse, and even for a given cytokine can differ according to the responding cell type, its differentiation stage, or its history of stimulation by other cytokines. Broadly, cytokines can regulate cell survival, proliferation, differentiation, morphology, and transcriptional and translational activities. Collectively these responses serve to establish metabolic states that protect the organism against infection by pathogens such as bacteria or viruses. However, although the production of cytokines is highly regulated, inappropriate or excessive levels can cause life-threatening inflammatory episodes or lead to chronic disease.

Preferred cytokines and receptors for them according to the invention include the following: members of the TNF family (TNF α/β, lymphotoxin α/β, TRANCE/RANKL, TRAIL, FasL and all combinations of subunits that compose biologically active multimeric ligands) and their receptors; Interleukin-1 (IL-1) and its receptors; IL-18 and its receptors; type I interferons (all α forms, β, and ω) and their receptors; type II interferon (γ) and its receptors. In a particularly preferred embodiment of the invention, the receptor is a TNF receptor. Examples of TNF family receptors include TNFR1 (also p55, p60), TNFRII (also p75, p80), KILLER/DR5, Fas/CD95, RANK, and osteoprotegerin.

A preferred TNFR1 receptor has the accession number X69810; a preferred TNFR2 receptor has the accession number U53481 and a preferred CD95/Fas receptor has the accession number HSFASX1. It will however be appreciated that the sequences referred to using such accession numbers may only include cDNA (expressed sequence), or they may include only small regions of upstream sequence. In particular they may not include upstream regions which may include promoter and enhancer sequences. It is clear that such upstream sequences may be used as target sequences for designing zinc fingers capable of binding to these sequences and thereby regulating expression of the receptors under their control or influence. However, it is a simple matter for the skilled person to determine the nature or sequence of such control regions, using methods known in the art (for example, chromosome walking, primer extension, etc).

Furthermore, determination of a corresponding genomic sequence enables identification of promoter and enhancer or other control regions. Sequences identified in the various genome sequencing projects currently being conducted, including the Human Genome Sequence Project, will also enable the skilled person to choose sequences for targeting. Thus, for example, it is a simple matter for a person skilled in the art to identify a genomic sequence corresponding to, for example, the CD4 receptor sequence, and to identify the control regions. If necessary, reference may be made to "The International Workshop on Human Leukocyte Differentiation Antigens" (Tissue Antigens. 1996 October; 48(4 Pt2):352-508).

TNFα

Originally identified as a factor capable of inducing the death of transformed cells, TNFα has since been found to exert induce a range of cellular responses. TNFα is a homotrimeric molecule formed by specific association of three polypeptide chains encoded by the TNFα gene locus. The protein is produced as a transmembrane complex, and when expressed at the cell surface the receptor-interacting domains are exposed to the extracellular space and are capable of interacting with their cognate receptor on adjacent cells. Although biologically active in this membrane-bound form, TNFα is generally found as a secreted product that is produced by specific cleavage of the membrane form by metalloproteinases.

Produced by macrophages and T cells, particularly those of the Th1 type, TNFα is regarded as a key cytokine for inducing immune responses, particularly those associated with inflammation. When it binds to its receptors it can induce expression of MHC class I molecules that present antigen to cytotoxic T cells, and adhesion molecules such as ICAM that promote recruitment of cells of the immune system to sites of inflammation. Importantly, TNFα often induces transcription of genes for these molecules in a synergistic fashion with other cytokines, particularly the interferons.

While TNFα serves an important function in promoting inflammation in order to neutralise pathogens, it is often associated with a range of clinical problems (19, 24). Acute over-production of TNFα in response to bacterial toxins can cause septicaemia, toxic shock syndrome, and other forms of immune damage. Chronic autoimmune diseases and other syndromes including inflammatory bowel disease, rheumatoid arthritis, psoriasis, myocarditis, myelodysplasia, multiple sclerosis, and type II diabetes are also linked to TNFα. Murine models have shown that over-expression of TNFα can lead to myocardial fibrosis, and this could be ameliorated with adenoviral gene therapy with a decoy TNF receptor (23). The pivotal role of TNFα in rheumatoid arthritis is illustrated by the favourable clinical responses of patients to treatment with an antibody to TNFα, Infliximab (20), or a recombinant decoy receptor, Etanercept (21).

TNFR1 Receptor

In a preferred embodiment of the invention, the receptor is capable of binding a ligand that is a member of the TNF family. In a highly preferred embodiment, the ligand is TNFα. Preferably, the receptor is TNFR1 (also p55, p60, CD120a). More preferably, the TNFR1 receptor comprises a receptor having accession number TNFR1 is X69810.

TNFα is recognised by two distinct cell-surface, transmembrane receptors: TNFRI (p55, p60, CD120a), and TNFR11 (p75, p80, CD120b). Each appears to function as a homotrimer (17). They have strong homology in their extracellular ligand-binding domains, but diverge in their intracellular domains and thereby transmit overlapping but distinct patterns of signals when engaged by TNFα (17). Consequently TNFRI and TNFRII have distinct immunological functions, as found in studies of mouse strains where genes for one or both have been knocked-out. Mouse strains susceptible to myocarditis do not develop inflammatory heart disease when TNFR1 is not expressed but TNFRII is still present (22). In a murine model of experimental autoimmune encephalomyelitis (EAE), knock-out of TNFRI prevented EAE, while knockout of TNFRII exacerbated the disease (18).

Accordingly, the polypeptides provided here may be used to target any cytokine receptor, including the TNFR1 receptor, and to regulate their expression. Such polypeptides may therefore be used to treat or prevent various diseases or syndromes associated with or caused by malfunction (in particular, up-regulation or over-expression or inappropriate activation, etc) of the receptor such as the TNFR1 receptor. Such diseases and syndromes include autoimmune diseases such as inflammation, autoimmune encephalomyelitis (EAE), rheumatoid arthritis, myocarditis, etc.

Variants

A nucleic acid binding polypeptide molecule as provided by the present invention includes splice variants encoded by mRNA generated by alternative splicing of a primary transcript, amino acid mutants, glycosylation variants and other covalent derivatives of said molecule which retain the physiological and/or physical properties of said molecule, such as its nucleic acid binding activity. Exemplary derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope, or may be a molecule capable of facilitating crossing of cell membrane(s) etc.

Derivatives can be fragments of the nucleic acid binding molecule. Fragments of said molecule comprise individual domains thereof, as well as smaller polypeptides derived from the domains. Preferably, smaller polypeptides derived from the molecule according to the invention define a single epitope which is characteristic of said molecule. Fragments may in theory be almost any size, as long as they retain one characteristic of the nucleic acid binding molecule. Preferably, fragments may be at least 3 amino acids and in length.

Derivatives of the nucleic acid binding molecule also comprise mutants thereof, which may contain amino acid deletions, additions or substitutions, subject to the requirement to maintain at least one feature characteristic of said molecule. Thus, conservative amino acid substitutions may be made substantially without altering the nature of the molecule, as may truncations from the N- or C-terminal ends, or the corresponding 5'- or 3'-ends of a nucleic acid encoding it. Deletions or substitutions may moreover be made to the fragments of the molecule comprised by the invention. Nucleic acid binding molecule mutants may be produced from a DNA encoding a nucleic acid binding protein which has been subjected to in vitro mutagenesis resulting e.g. in an addition, exchange and/or deletion of one or more amino acids. For example, substitutional, deletional or insertional variants of the molecule can be prepared by recombinant methods and screened for nucleic acid binding activity as described herein.

The fragments, mutants and other derivatives of the polypeptide nucleic acid binding molecule preferably retain substantial homology with said molecule. As used herein, "homology" means that the two entities share sufficient characteristics for the skilled person to determine that they are similar in origin and/or function. Preferably, homology is used to refer to sequence identity. Thus, the derivatives of the molecule preferably retain substantial sequence identity with the sequence of said molecule. Examples of such sequences are presented as consensus sequences 1 to 8.

"Substantial homology", where homology indicates sequence identity, means more than 75% sequence identity and most preferably a sequence identity of 90% or more. Amino acid sequence identity may be assessed by any suitable means, including the BLAST comparison technique which is well known in the art, and is described in Ausubel et al., Short Protocols in Molecular Biology (1999) $4^{th}$ Ed, John Wiley & Sons, Inc.

Mutations

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A. Innis, D. H. Gelfand, J. J. Sninsky, T. J. White (eds.). Academic Press, New York, 1990). Preferably, the commercially available Altered Site II Mutagenesis System (Promega) may be employed, according to the directions given by the manufacturer.

Screening of the proteins produced by mutant genes is preferably performed by expressing the genes and assaying the binding ability of the protein product. A simple and advantageously rapid method by which this may be accomplished is by phage display, in which the mutant polypeptides are expressed as fusion proteins with the coat proteins of filamentous bacteriophage, such as the minor coat protein pII of bacteriophage m13 or gene III of bacteriophage Fd, and displayed on the capsid of bacteriophage transformed with the mutant genes. The target nucleic acid sequence is used as a probe to bind directly to the protein on the phage surface and select the phage possessing advantageous mutants, by affinity purification. The phage are then amplified by passage through a bacterial host, and subjected to further rounds of selection and amplification in order to enrich the mutant pool for the desired phage and eventually isolate the preferred clone(s). Detailed methodology for phage display is known in the art and set forth, for example, in U.S. Pat. No. 5,223,409; Choo and Klug, (1995) Current Opinions in Biotechnology 6:431-436; Smith, (1985) Science 228:1315-1317; and McCafferty et al., (1990) Nature 348:552-554; all incorporated herein by reference. Vector systems and kits for phage display are available commercially, for example from Pharmacia.

The present invention allows the production of what are essentially artificial nucleic acid binding proteins. In these proteins, artificial analogues of amino acids may be used, to impart the proteins with desired properties or for other reasons. Thus, the term "amino acid", particularly in the context where "any amino acid" is referred to, means any sort of natural or artificial amino acid or amino acid analogue that may be employed in protein construction according to methods known in the art. Moreover, any specific amino acid referred to herein may be replaced by a functional analogue thereof, particularly an artificial functional analogue. The nomenclature used herein therefore specifically comprises within its scope functional analogues of the defined amino acids.

The polypeptides which comprise the libraries according to the invention may comprise zinc finger polypeptides. In other words, they comprise a Cys2-His2 zinc finger motif.

Molecules according to the invention may advantageously comprise multiple zinc finger motifs. For example, molecules according to the invention may comprise any number of motifs, such as three zinc finger motifs, or may comprise four or five such motifs, or may comprise six zinc finger motifs, or even more. Advantageously, molecules according to the invention may comprise zinc finger motifs in multiples of three, such as three, six, nine or even more zinc finger motifs. Preferably, molecules according to the invention may comprise about three to about six zinc finger motifs.

Nucleic Acid Binding Polypeptides

This invention relates to nucleic acid binding polypeptides. The term "polypeptide" (and the terms "peptide" and "protein") are used interchangeably to refer to a polymer of amino acid residues, preferably including naturally occurring amino acid residues. Artificial analogues of amino acids may also be used in the nucleic acid binding polypeptides, to impart the proteins with desired properties or for other reasons. The term "amino acid", particularly in the context where "any amino acid" is referred to, means any sort of natural or artificial amino acid or amino acid analogue that may be employed in protein construction according to methods known in the art. Moreover, any specific amino acid referred to herein may be replaced by a functional analogue thereof, particularly an artificial functional analogue. Polypeptides may be modified, for example by the addition of carbohydrate residues to form glycoproteins.

As used herein, "nucleic acid" includes both RNA and DNA, constructed from natural nucleic acid bases or synthetic bases, or mixtures thereof. Preferably, however, the binding polypeptides of the invention are DNA binding polypeptides.

Particularly preferred examples of nucleic acid binding polypeptides are Cys2-His2 zinc finger binding proteins which, as is well known in the art, bind to target nucleic acid sequences via α-helical zinc metal atom co-ordinated binding motifs known as zinc fingers. Each zinc finger in a zinc finger nucleic acid binding protein is responsible for determining binding to a nucleic acid triplet, or an overlapping quadruplet, in a nucleic acid binding sequence. Preferably, there are 2 or more zinc fingers, for example 2, 3, 4, 5, 6, 7, 8, 9, 10, 11, 12, 13, 14, 15, 16, 17, 18 or more zinc fingers, in each binding protein. Advantageously, the number of zinc fingers in each zinc finger binding protein is a multiple of 2.

All of the DNA binding residue positions of zinc fingers, as referred to herein, are numbered from the first residue in the α-helix of the finger, ranging from +1 to +9. "−1" refers to the residue in the framework structure immediately preceding the α-helix in a Cys2-His2 zinc finger polypeptide. Residues referred to as "++" are residues present in an adjacent (C-terminal) finger. Where there is no C-terminal adjacent finger, "++" interactions do not operate.

The present invention is in one aspect concerned with the production of what are essentially artificial DNA binding proteins. In these proteins, artificial analogues of amino acids may be used, to impart the proteins with desired properties or for other reasons. Thus, the term "amino acid", particularly in the context where "any amino acid" is referred to, means any sort of natural or artificial amino acid or amino acid analogue that may be employed in protein construction according to methods known in the art. Moreover, any specific amino acid referred to herein may be replaced by a functional analogue thereof, particularly an artificial functional analogue. The nomenclature used herein therefore specifically comprises within its scope functional analogues or mimetics of the defined amino acids.

The α-helix of a zinc finger binding protein aligns antiparallel to the nucleic acid strand, such that the primary nucleic acid sequence is arranged 3' to 5' in order to correspond with the N terminal to C-terminal sequence of the zinc finger. Since nucleic acid sequences are conventionally written 5' to 3', and amino acid sequences N-terminus to C-terminus, the result is that when a nucleic acid sequence and a zinc finger protein are aligned according to convention, the primary interaction of the zinc finger is with the − strand of the nucleic acid, since it is this strand which is aligned 3' to 5'. These conventions are followed in the nomenclature used herein. It should be noted, however, that in nature certain fingers, such as finger 4 of the protein GLI bind to the + strand of nucleic acid: see Suzuki et al., (1994) NAR 22:3397-3405 and Pavletich and Pabo, (1993) Science 261:1701-1707. The incorporation of such fingers into DNA binding molecules according to the invention is envisaged.

The present invention may be integrated with the rules set forth for zinc finger polypeptide design in our copending European or PCT patent applications having publication numbers; WO 98/53057, WO 98/53060, WO 98/53058, WO 98/53059, describe improved techniques for designing zinc finger polypeptides capable of binding desired nucleic acid sequences. In combination with selection procedures, such as phage display, set forth for example in WO 96/06166, these techniques enable the production of zinc finger polypeptides capable of recognising practically any desired sequence.

Thus, in one embodiment, the invention provides a method for preparing a nucleic acid binding polypeptide of the Cys2-His2 zinc finger class capable of binding to a target DNA sequence comprising a receptor nucleotide sequence, in which binding to each base of a DNA triplet by an α-helical zinc finger DNA binding module in the polypeptide is determined as follows: if the 5' base in the triplet is G, then position +6 in the α-helix is Arg and/or position ++2 is Asp; if the 5' base in the triplet is A, then position +6 in the α-helix is Gln or Glu and ++2 is not Asp; if the 5' base in the triplet is T, then position +6 in the α-helix is Ser or Thr and position ++2 is Asp; or position +6 is a hydrophobic amino acid other than Ala; if the 5' base in the triplet is C, then position +6 in the α-helix may be any amino acid, provided that position ++2 in the α-helix is not Asp; if the central base in the triplet is G, then position +3 in the α-helix is His; if the central base in the triplet is A, then position +3 in the α-helix is Asn; if the central base in the triplet is T, then position +3 in the α-helix is Ala, Ser, Ile, Leu, Thr or Val; provided that if it is Ala, then one of the residues at −1 or +6 is a small residue; if the central base in the triplet is 5-meC, then position +3 in the α-helix is Ala, Ser, Ile, Leu, Thr or Val; provided that if it is Ala, then one of the residues at −1 or +6 is a small residue; if the 3' base in the triplet is G, then position −1 in the α-helix is Arg; if the 3' base in the triplet is A, then position −1 in the α-helix is Gln and position +2 is Ala; if the 3' base in the triplet is T, then position −1 in the α-helix is Asn; or position −1 is Gln and position +2 is Ser; if the 3' base in the triplet is C, then position −1 in the α-helix is Asp and Position +1 is Arg; where the central residue of a target triplet is C, the use of Asp at position +3 of a zinc finger polypeptide allows preferential binding to C over 5-meC.

The foregoing represents a set of rules which permits the design of a zinc finger binding protein specific for any given target DNA sequence, in particular a receptor nucleotide sequence.

A zinc finger binding motif is a structure well known to those in the art and defined in, for example, Miller et al., (1985) EMBO J. 4:1609-1614; Berg (1988) PNAS (USA) 85:99-102; Lee et al., (1989) Science 245:635-637; see International patent applications WO 96/06166 and WO 96/32475, corresponding to U.S. Ser. No. 08/422,107, incorporated herein by reference.

In general, a preferred zinc finger framework has the structure:

(A) $X_{0-2} \, C \, X_{1-5} \, C \, X_{9-14} \, H \, X_{3-6} \, H/C$ (SEQ ID NO:114)

where X is any amino acid, and the numbers in subscript indicate the possible numbers of residues represented by X.

The above framework may be further refined to include the structure:

(SEQ ID NO: 114)
$$(A') \quad X_{0-2} \, \underset{}{C} \, X_{3-5} \, \underset{}{C} \, X_{2-7} \, \underset{-1}{X} \, \underset{a}{X} \, \underset{2}{X} \, \underset{3}{X} \, \underset{4}{X} \, \underset{5}{X} \, \underset{6}{X} \, \underset{7}{X} \, \underset{}{H} \, X_{3-6} \, H/C$$

where X is any amino acid, and the numbers in subscript indicate the possible numbers of residues represented by X.

In a preferred aspect of the present invention, zinc finger nucleic acid binding motifs may be represented as motifs having the following primary structure:

(B)
(SEQ ID NO: 116)
$$X^a \, \underset{}{C} \, X_{2-4} \, \underset{}{C} \, X_{2-3} \, \underset{-1}{F} \, \underset{1}{X^c} \, \underset{2}{X} \, \underset{3}{X} \, \underset{4}{X} \, \underset{5}{L} \, \underset{6}{X} \, \underset{7}{X} \, \underset{8}{H} \, \underset{9}{X} \, X \, X^b \, H\text{-linker}$$

wherein X (including $X^a$, $X^b$ and $X^c$) is any amino acid. $X_{2-4}$ and $X_{2-3}$ refer to the presence of 2 or 4, or 2 or 3, amino acids, respectively. The Cys and His residues, which together co-ordinate the zinc metal atom, are marked in bold text and are usually invariant, as is the Leu residue at position +4 in the α-helix. The linker, as noted elsewhere, may comprise a canonical, structured or flexible linker. Structured and flexible linkers are described below, and in our UK application numbers GB 0001582.6, GB0013103.7, GB0013104.5 and our International Patent Application filed 19 Jan. 2001 PCT/GB01/00202 (WO01/53480), all of which are hereby incorporated by reference.

Modifications to this representation may occur or be effected without necessarily abolishing zinc finger function, by insertion, mutation or deletion of amino acids. For example it is known that the second His residue may be replaced by Cys (Krizek et al., (1991) J. Am. Chem. Soc. 113:4518-4523) and that Leu at +4 can in some circumstances be replaced with Arg. The Phe residue before $X_c$ may be replaced by any aromatic other than Trp. Moreover, experiments have shown that departure from the preferred structure and residue assignments for the zinc finger are tolerated and may even prove beneficial in binding to certain nucleic acid sequences. Even taking this into account, however, the general structure involving an α-helix coordinated by a zinc atom which contacts four Cys or His residues, does not alter. As used herein, structures (A) and (B) above are taken as an exemplary structure representing all zinc finger structures of the Cys2-His2 type.

Preferably, $X^a$ is $^F/_Y$-X or P-$^F/_Y$-X. In this context, X is any amino acid. Preferably, in this context X is E, K, T or S. Less preferred but also envisaged are Q, V, A and P. The remaining amino acids remain possible.

Preferably, $X_{2-4}$ consists of two amino acids rather than four. The first of these amino acids may be any amino acid, but S, E, K, T, P and R are preferred. Advantageously, it is P or R The second of these amino acids is preferably E, although any amino acid may be used.

Preferably, $X^b$ is T or I. Preferably, $X^c$ is S or T.

Preferably, $X_{2-3}$ is G-K-A, G-K-C, G-K-S or G-K-G. However, departures from the preferred residues are possible, for example in the form of M-R-N or M-R.

As set out above, the major binding interactions occur with amino acids −1, +3 and +6. Amino acids +4 and +7 are largely invariant. The remaining amino acids may be essentially any amino acids. Preferably, position +9 is occupied by Arg or Lys. Advantageously, positions +1, +5 and +8 are not hydrophobic amino acids, that is to say are not Phe, Trp or Tyr. Preferably, position ++2 is any amino acid, and preferably serine, save where its nature is dictated by its role as a ++2 amino acid for an N-terminal zinc finger in the same nucleic acid binding molecule.

The code provided by the present invention is not entirely rigid; certain choices are provided. For example, positions +1, +5 and +8 may have any amino acid allocation, whilst other positions may have certain options: for example, the present rules provide that, for binding to a central T residue, any one of Ala, Ser or Val may be used at +3. In its broadest sense, therefore, the present invention provides a very large number of proteins which are capable of binding to every defined target DNA triplet.

Preferably, however, the number of possibilities may be significantly reduced. For example, the non-critical residues +1, +5 and +8 may be occupied by the residues Lys, Thr and Gln respectively as a default option. In the case of the other choices, for example, the first-given option may be employed as a default. Thus, the code according to the present invention allows the design of a single, defined polypeptide (a "default" polypeptide) which will bind to its target triplet. Zinc fingers may be based on naturally occurring zinc fingers and consensus zinc fingers.

In general, naturally occurring zinc fingers may be selected from those fingers for which the DNA binding specificity is known. For example, these may be the fingers for which a crystal structure has been resolved: namely Zif 268 (Elrod-Erickson et al., (1996) Structure 4:1171-1180), GLI (Pavletich and Pabo, (1993) Science 261:1701-1707), Tramtrack (Fairall et al., (1993) Nature 366:483-487) and YY1 (Houbaviy et al., (1996) PNAS (USA) 93:13577-13582). Preferably, the modified nucleic acid binding polypeptide is derived from Zif 268, GAC, or a Zif-GAC fusion comprising three fingers from Zif linked to three fingers from GAC. By "GAC-clone", we mean a three-finger variant of ZIF268 which is capable of binding the sequence GCGGACGCG, as described in Choo & Klug (1994), Proc. Natl. Acad. Sci. USA, 91, 11163-11167.

The naturally occurring zinc finger 2 in Zif 268 makes an excellent starting point from which to engineer a zinc finger and is preferred.

Consensus zinc finger structures may be prepared by comparing the sequences of known zinc fingers, irrespective of whether their binding domain is known. Preferably, the consensus structure is selected from the group consisting of the consensus structure P Y K C P E C G K S F S Q K S D L V K H Q R T H T (SEQ ID NO:13), and the consensus structure P Y K C S E C G K A F S Q K S N L T R H Q R I H T (SEQ ID NO:14).

The consensuses are derived from the consensus provided by Krizek et al., (1991) J. Am. Chem. Soc. 113: 4518-4523 and from Jacobs, (1993) PhD thesis, University of Cambridge, UK. In both cases, canonical, structured or flexible linker sequences, as described below, may be formed on the ends of the consensus for joining two zinc finger domains together.

When the nucleic acid specificity of the model finger selected is known, the mutation of the finger in order to modify its specificity to bind to the target DNA may be directed to residues known to affect binding to bases at which the natural and desired targets differ. Otherwise, mutation of the model fingers should be concentrated upon residues −1, +3, +6 and ++2 as provided for in the foregoing rules.

In order to produce a binding protein having improved binding, moreover, the rules provided by the present invention may be supplemented by physical or virtual modelling of the protein/DNA interface in order to assist in residue selection.

In a further embodiment, the invention provides a method for producing a zinc finger polypeptide capable of binding to a target DNA sequence comprising a receptor nucleotide sequence, the method comprising: a) providing a nucleic acid library encoding a repertoire of zinc finger domains or modules, the nucleic acid members of the library being at least partially randomised at one or more of the positions encoding residues −1, 2, 3 and 6 of the α-helix of the zinc finger modules; b) displaying the library in a selection system and screening it against the target DNA sequence; and c) isolating the nucleic acid members of the library encoding zinc finger modules or domains capable of binding to the target sequence.

Methods for the production of libraries encoding randomised polypeptides are known in the art and may be applied in the present invention. Randomisation may be total, or partial; in the case of partial randomisation, the selected codons preferably encode options for amino acids as set forth in the rules above.

Zinc finger polypeptides may be designed which specifically bind to nucleic acids incorporating the base U, in preference to the equivalent base T.

In a further preferred aspect, the invention comprises a method for producing a zinc finger polypeptide capable of binding to a target DNA sequence comprising a receptor nucleotide sequence, the method comprising: a) providing a nucleic acid library encoding a repertoire of zinc finger polypeptides each possessing more than one zinc finger, the nucleic acid members of the library being at least partially randomised at one or more of the positions encoding residues −1, 2, 3 and 6 of the α-helix in a first zinc finger and at one or more of the positions encoding residues −1, 2, 3 and 6 of the α-helix in a further zinc finger of the zinc finger polypeptides; b) displaying the library in a selection system and screening it against the target DNA sequence; and d) isolating the nucleic acid members of the library encoding zinc finger polypeptides capable of binding to the target sequence.

In this aspect, the invention encompasses library technology described in our copending International patent application WO 98/53057, incorporated herein by reference in its entirety. WO 98/53057 describes the production of zinc finger polypeptide libraries in which each individual zinc finger polypeptide comprises more than one, for example two or three, zinc fingers; and wherein within each polypeptide partial randomisation occurs in at least two zinc fingers. This allows for the selection of the "overlap" specificity, wherein, within each triplet, the choice of residue for binding to the third nucleotide (read 3' to 5' on the +strand) is influenced by the residue present at position +2 on the subsequent zinc finger, which displays cross-strand specificity in binding. The selection of zinc finger polypeptides incorporating cross-strand specificity of adjacent zinc fingers enables the selection of nucleic acid binding proteins more quickly, and/or with a higher degree of specificity than is otherwise possible.

The above rules allow the engineering of a zinc finger capable of binding to a given nucleotide sequence. Engineering of zinc fingers which involves applying rules which specify the choice of amino acid residues based on the identity of residues in a target nucleic acid sequence is referred to here as "rule based" or "rational" design. Such rational design provides a great deal of versatility in zinc finger design, and may be used instead of, or to complement zinc finger production by selection from libraries.

Zinc finger binding motifs designed according to the invention may be combined into nucleic acid binding polypeptide molecules having a multiplicity of zinc fingers. Preferably, the proteins have at least two zinc fingers. The presence of at least three zinc fingers is preferred. Nucleic acid binding proteins may be constructed by joining the required fingers end to end, N-terminus to C-terminus, with canonical, flexible or structured linkers, as described below. Preferably, this is effected by joining together the relevant nucleic acid sequences which encode the zinc fingers to produce a composite nucleic acid coding sequence encoding the entire binding protein.

The invention therefore provides a method for producing a DNA binding protein as defined above, wherein the DNA binding protein is constructed by recombinant DNA technology, the method comprising the steps of preparing a nucleic acid coding sequence encoding a plurality of zinc finger domains or modules defined above, inserting the nucleic acid sequence into a suitable expression vector; and expressing the nucleic acid sequence in a host organism in order to obtain the DNA binding protein. A "leader" peptide may be added to the N-terminal finger. Preferably, the leader peptide is MAEEKP.

Flexible and Structured Linkers

The nucleic acid binding polypeptides according to the invention may comprise one or more linker sequences. The linker sequences may comprise one or more flexible linkers, one or more structured linkers, or any combination of flexible and structured linkers. Such linkers are disclosed in our co-pending British Patent Application Numbers 0001582.6, 0013102.9, 0013103.7, 0013104.5 and International Patent Application Number PCT/GB01/00202 (WO01/53480), which are incorporated by reference.

By "linker sequence" we mean an amino acid sequence that links together two nucleic acid binding modules. For example, in a "wild type" zinc finger protein, the linker sequence is the amino acid sequence lacking secondary structure which lies between the last residue of the c-helix in a zinc finger and the first residue of the β-sheet in the next zinc finger. The linker sequence therefore joins together two zinc fingers. Typically, the last amino acid in a zinc finger is a threonine residue, which caps the α-helix of the zinc finger, while a tyrosine/phenylalanine or another hydrophobic residue is the first amino acid of the following zinc finger. Accordingly, in a "wild type" zinc finger, glycine is the first residue in the linker, and proline is the last residue of the linker. Thus, for example, in the Zif268 construct, the linker sequence is G(E/Q)(K/R)P (SEQ ID NOs:16 to 19).

A "flexible" linker is an amino acid sequence which does not have a fixed structure (secondary or tertiary structure) in solution. Such a flexible linker is therefore free to adopt a variety of conformations. An example of a flexible linker is the canonical linker sequence GERP (SEQ ID NO:17)/GEKP (SEQ ID NO:16)/GQRP (SEQ ID NO:19)/GQKP (SEQ ID NO:18). Flexible linkers are also disclosed in WO99/45132 (Kim and Pabo). By "structured linker" we mean an amino acid sequence which adopts a relatively well-defined conformation when in solution. Structured linkers are therefore those which have a particular secondary and/or tertiary structure in solution.

Determination of whether a particular sequence adopts a structure may be done in various ways, for example, by sequence analysis to identify residues likely to participate in protein folding, by comparison to amino acid sequences which are known to adopt certain conformations (e.g., known alpha-helix, beta-sheet or zinc finger sequences), by NMR spectroscopy, by X-ray diffraction of crystallised peptide containing the sequence, etc as known in the art.

The structured linkers of our invention preferably do not bind nucleic acid, but where they do, then such binding is not sequence specific. Binding specificity may be assayed for example by gel-shift as described below.

The linker may comprise any amino acid sequence that does not substantially hinder interaction of the nucleic acid binding modules with their respective target subsites. Preferred amino acid residues for flexible linker sequences include, but are not limited to, glycine, alanine, serine, threonine proline, lysine, arginine, glutamine and glutamic acid.

The linker sequences between the nucleic acid binding domains preferably comprise five or more amino acid residues. The flexible linker sequences according to our invention consist of 5 or more residues, preferably, 5, 6, 7, 8, 9, 10, 11, 12, 13, 14, 15, 16, 17, 18, 19 or 20 or more residues. In a highly preferred embodiment of the invention, the flexible linker sequences consist of 5, 7 or 10 residues.

Once the length of the amino acid sequence has been selected, the sequence of the linker may be selected, for example by phage display technology (see for example U.S. Pat. No. 5,260,203) or using naturally occurring or synthetic linker sequences as a scaffold (for example, GQKP and GEKP, see Liu et al., 1997, Proc. Natl. Acad. Sci. USA 94, 5525-5530 and Whitlow et al., 1991, Methods: A Companion to Methods in Enzymology 2: 97-105). The linker sequence may be provided by insertion of one or more amino acid residues into an existing linker sequence of the nucleic acid binding polypeptide. The inserted residues may include glycine and/or serine residues. Preferably, the existing linker sequence is a canonical linker sequence selected from GEKP (SEQ ID NO:16), GERP (SEQ ID NO:17), GQKP (SEQ ID NO:18) and GQRP (SEQ ID NO:19). More preferably, each of the linker sequences comprises a sequence selected from GGEKP (SEQ ID NO:20), GGQKP (SEQ ID NO:21), GGS-GEKP (SEQ ID NO:22), GGSGQKP (SEQ ID NO:23), GGSGGSGEKP (SEQ ID NO:24), and GGSGGSGQKP (SEQ ID NO:25).

Structured linker sequences are typically of a size sufficient to confer secondary or tertiary structure to the linker; such linkers may be up to 30, 40 or 50 amino acids long. In a preferred embodiment, the structured linkers are derived from known zinc fingers which do not bind nucleic acid, or are not capable of binding nucleic acid specifically. An example of a structured linker of the first type is TFIIIA finger IV; the crystal structure of TFIIIA has been solved, and this shows that finger IV does not contact the nucleic acid (Nolte et al., 1998, *Proc. Natl. Acad. Sci. USA* 95, 2938-2943.). An example of the latter type of structured linker is a zinc finger which has been mutagenised at one or more of its base contacting residues to abolish its specific nucleic acid binding capability. Thus, for example, a ZIF finger 2 which has residues −1, 2, 3 and 6 of the recognition helix mutated to serines so that it no longer specifically binds DNA may be used as a structured linker to link two nucleic acid binding domains.

The use of structured or rigid linkers to jump the minor groove of DNA is likely to be especially beneficial in (i) linking zinc fingers that bind to widely separated (>3 bp) DNA sequences, and (ii) also in minimising the loss of binding energy due to entropic factors.

Typically, the linkers are made using recombinant nucleic acids encoding the linker and the nucleic acid binding modules, which are fused via the linker amino acid sequence. The linkers may also be made using peptide synthesis and then linked to the nucleic acid binding modules. Methods of manipulating nucleic acids and peptide synthesis methods are known in the art (see, for example, Maniatis, et al., 1991. *Molecular Cloning: A Laboratory Manual*. Cold Spring Harbor, N.Y., Cold Spring Harbor Laboratory Press).

Transcriptional Regulation

The nucleic acid binding polypeptides according to our invention may be linked to one or more transcriptional effector domains, such as an activation domain or a repressor domain. Examples of transcriptional activation domains include the VP16 and VP64 transactivation domains of Herpes Simplex Virus. Alternative transactivation domains are various and include the maize C1 transactivation domain sequence (Sainz et al., 1997, Mol. Cell. Biol. 17: 115-22) and P1 (Goff et al., 1992, Genes Dev. 6: 864-75; Estruch et al., 1994, Nucleic Acids Res. 22: 3983-89) and a number of other domains that have been reported from plants (see Estruch et al., 1994, ibid).

Instead of incorporating a transactivator of gene expression, a repressor of gene expression can be fused to the nucleic acid binding polypeptide and used to down regulate the expression of a gene contiguous or incorporating the nucleic acid binding polypeptide target sequence. Such repressors are known in the art and include, for example, the KRAB-A domain (Moosmann et al., Biol. Chem. 378: 669-677 (1997)) the engrailed domain (Han et al., Embo J. 12: 2723-2733 (1993)) and the snag domain (Grimes et al., Mol Cell. Biol. 16: 6263-6272 (1996)). These can be used alone or in combination to down-regulate gene expression.

It is known that zinc finger proteins may be fused to transcriptional repression domains such as the Kruppel-associated box (KRAB) domain to form powerful repressors. These fusions are known to repress expression of a reporter gene even when bound to sites a few kilobase pairs upstream from the promoter of the gene (Margolin et al., 1994, PNAS USA 91, 4509-4513). Thus, zinc finger-KRAB fusion proteins capable of binding to nucleic acid sequences comprising a receptor nucleotide sequence may be used to regulate expression, preferably enable down regulation, of receptors.

Multifinger Polypeptides

According to a preferred embodiment of the present invention, the nucleic acid binding polypeptides comprise a plurality of binding domains or motifs. For example, a preferred zinc finger polypeptide according the invention comprises 2, 3, 4, 5, 6, 7, 8, 9, 10, 11, 12, 13, 14, 15, 16, 17, 18, 19, 20, 21, 22, 23, 24, etc or more zinc finger binding domains or motifs. Highly preferred embodiments are zinc finger polypeptides which comprise three zinc finger motifs and those which comprise six finger motifs.

Zinc finger polypeptides comprising multiple fingers may be constructed by joining together two or more zinc finger polypeptides (which may themselves be selected using phage display, as described elsewhere in this document) with suitable linker sequences.

Means of joining polypeptide sequences, for example, by recombinant DNA technology are known in the art, and are for example disclosed in Sambrook et al (supra) and Ausubel et al (supra). Furthermore, other sequences such as nuclear localisation sequences and "tag" sequences for purification may be included as known in the art A specific example of production of a six finger protein 6F6 is described in the Examples below.

Vectors

The nucleic acid encoding the nucleic acid binding protein according to the invention may be incorporated into vectors for further manipulation. As used herein, vector (or plasmid) refers to discrete elements that are used to introduce heterologous nucleic acid into cells for either expression or replication thereof. Selection and use of such vehicles are well within the skill of the person of ordinary skill in the art. Many vectors are available, and selection of appropriate vector will depend on the intended use of the vector, i.e. whether it is to be used for DNA amplification or for nucleic acid expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2μ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast or mammalian cells even though it is not capable of replicating independently of the host cell chromosome. DNA may also be replicated by insertion into the host genome. However, the recovery of genomic DNA encoding the nucleic acid binding protein is more complex than that of exogenously replicated vector because restriction enzyme digestion is required to excise nucleic acid binding protein DNA. DNA can be amplified by PCR and be directly transfected into the host cells without any replication component.

Selectable Markers

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript© vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up nucleic acid binding protein nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the nucleic acid binding protein. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression

Expression and cloning vectors usually contain a promoter that is recognised by the host organism and is operably linked to nucleic acid binding protein encoding nucleic acid. Such a promoter may be inducible or constitutive. The promoters are operably linked to DNA encoding the nucleic acid binding protein by removing the promoter from the source DNA by restriction enzyme digestion and inserting the isolated promoter sequence into the vector. Both the native nucleic acid binding protein promoter sequence and many heterologous promoters may be used to direct amplification and/or expression of nucleic acid binding protein encoding DNA.

Promoters suitable for use with prokaryotic hosts include, for example, the β-lactamase and lactose promoter systems, alkaline phosphatase, the tryptophan (Trp) promoter system and hybrid promoters such as the tac promoter. Their nucleotide sequences have been published, thereby enabling the skilled worker operably to ligate them to DNA encoding nucleic acid binding protein, using linkers or adapters to supply any required restriction sites. Promoters for use in bacterial systems will also generally contain a Shine-Delgarno sequence operably linked to the DNA encoding the nucleic acid binding protein.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60-89, 1990). In the *E. coli* BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for over-production of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcHisXpressTm (Invitrogen) or pTrc99 (Pharmacia Biotech, SE) or vectors containing the tac promoter such as pKK223-3 (Pharmacia Biotech) or PMAL (New England Biolabs, MA, USA).

Moreover, the nucleic acid binding protein gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate. A "leader" peptide may be added to the N-terminal finger. Preferably, the leader peptide is MAEEKP.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

Nucleic acid binding protein gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with nucleic acid binding protein sequence, provided such promoters are compatible with the host cell systems.

Transcription of a DNA encoding nucleic acid binding protein by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to nucleic acid binding protein DNA, but is preferably located at a site 5' from the promoter.

Advantageously, a eukaryotic expression vector encoding a nucleic acid binding protein according to the invention may comprise a locus control region (LCR). LCRs are capable of directing high-level integration site independent expression of transgenes integrated into host cell chromatin, which is of importance especially where the nucleic acid binding protein gene is to be expressed in the context of a permanently-transfected eukaryotic cell line in which chromosomal integration of the vector has occurred, or in transgenic animals.

Eukaryotic vectors may also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding nucleic acid binding protein.

An expression vector includes any vector capable of expressing nucleic acid binding protein nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding nucleic acid binding protein may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding nucleic acid binding protein in mammalian cells. Transient expression usually involves the use of an expression vector that is able to replicate efficiently in a host cell, such that the host cell accumulates many copies of the expression vector, and, in turn, synthesises high levels of nucleic acid binding protein. For the purposes of the present invention, transient expression systems are useful e.g. for identifying nucleic acid binding protein mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing nucleic acid binding protein expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing the nucleic acid binding protein. Suitable prokaryotes include eubacteria, such as Gram-negative or Gram-positive organisms, such as *E. coli*, e.g. *E. coli* K-12 strains, DH5a and HB101, or Bacilli. Further hosts suitable for the nucleic acid binding protein encoding vectors include eukaryotic microbes such as filamentous fungi or yeast, e.g. *Saccharomyces cerevisiae*. Higher eukaryotic cells include insect and vertebrate cells, particularly mammalian cells including human cells or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of the nucleic acid binding protein-encoding nucleic acid to form the nucleic acid binding protein. The precise amounts of DNA encoding the nucleic acid binding protein may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby the nucleic acid binding protein encoded by the DNA is expressed. The composition of suitable media is known to those in the art, so that they can be readily prepared. Suitable culturing media are also commercially available.

Nucleic acid binding molecules according to the invention may be employed in a wide variety of applications, including diagnostics and as research tools. Advantageously, they may be employed as diagnostic tools for identifying the presence of nucleic acid molecules in a complex mixture.

Preferred molecules according to the invention have gene-specific DNA binding activity. These may be constructed by the engineering of DNA-binding polypeptide domains with given DNA sequence-specificity, to target the appropriate gene(s).

Given the speed and convenience with which a great number of selections can be performed in parallel using the bipartite library strategy, we believe that the system is of great utility. The 'bipartite' system is a most time- and cost-effective general method of engineering zinc fingers by phage display.

Described herein is a rapid and convenient method that can be used to design zinc finger proteins against an unlimited set of DNA binding sites. This is based on a pair of pre-made zinc finger phage display libraries, which are used in parallel to select two DNA-binding domains that each recognise given 5 bp sequences, and whose products are recombined to produce a single protein that recognises a composite (10 bp) site of predefined sequence. Engineering using this system can be completed in less than two weeks and yields polypeptide molecules that bind sequence-specifically to DNA with $K_d$s in the nanomolar range. Library selection is therefore suitable for production of zinc fingers capable of binding to sequences comprising receptor nucleotide sequences. Our methods enable the production of polypeptides capable of binding to any receptor nucleotide sequence, by identification of a motif or sequence within that sequence, and selection of one or more zinc fingers (or other nucleic acid binding polypeptides) which bind to that sequence or motif.

As used herein, the term 'region' may mean part, segment, locus, area, fragment, motif, domain, section, site or similar part of said promoter, and may even include the promoter in its entirety. Thus, the phrase 'region of the/a . . . promoter' includes segment(s), fragments etc. of the promoter, and may include the whole promoter, or motifs therein such as transcription factor binding site(s), or other such parts thereof.

Presented herein is a zinc finger engineering strategy which (i) yields zinc finger polymers that bind DNA specifically, with good affinity, and without significant sequence restrictions on the generation of such polymer molecules, (ii) can be executed relatively rapidly, and (iii) can be easily adapted to a high-throughput automated format. This strategy is based on recent advances in our understanding of zinc finger function, particularly the phenomenon of synergistic DNA recognition by adjacent zinc fingers (11, 18), in combination with certain technical advances in zinc finger library design as discussed herein. The invention thus relates to the construction of a zinc finger library according to the new strategy disclosed herein.

It should be noted that it is possible for the recombinant proteins of the present invention to feature idiosyncratic combinations of amino acids that would not necessarily have been predicted by a recognition code. This is particularly true of the combinations of amino acids that are responsible for the inter-finger synergy that allows any base-pair to be specified at the interface of zinc finger DNA subsites (11).

Zinc finger domains may be made by methods described and/or referred to herein. For example, said zinc finger DNA binding domains may be made as discussed in the examples, or as described in one or more of WO96/06166, WO98/53058, WO98/53057, or WO/98/53060.

Library

The nucleic acid binding polypeptides, including zinc finger polypeptides, capable of binding and preferably down-regulating nucleic acid sequences comprising receptor nucleotide sequences, may be selected from a library.

The term "library" is used according to its common usage in the art, to denote a collection of polypeptides or, preferably, nucleic acids encoding polypeptides. The polypeptides of the invention contain regions of randomisation, such that each library will comprise or encode a repertoire of polypeptides, wherein individual polypeptides differ in sequence from each other. The same principle is present in virtually all libraries developed for selection, such as by phage display.

Randomisation, as used herein, refers to the variation of the sequence of the polypeptides which comprise the library, such that various amino acids may be present at any given position in different polypeptides. Randomisation may be complete, such that any amino acid may be present at a given position, or partial, such that only certain amino acids are present. Preferably, the randomisation is achieved by mutagenesis at the nucleic acid level, for example by synthesising novel genes encoding mutant proteins and expressing these to obtain a variety of different proteins. Alternatively, existing genes can be themselves mutated, such by site-directed or random mutagenesis, in order to obtain the desired mutant genes.

The 'Bipartite' Library Strategy

Nucleic acids encoding nucleic acid binding polypeptides according to the invention may be selected using a 'bipartite-complementary' system for the construction of DNA-binding domains by phage display. This system comprises two master libraries, Lib12 and Lib23, each of which encodes variants of a three-finger DNA-binding domain based on that of the transcription factor Zif268 (6, 19). The two libraries are complementary because Lib12 contains randomisations in all the base-contacting positions of F1 and certain base-contacting positions of F2, while Lib23 contains randomisations in the remaining base-contacting positions of F2 and all the base-contacting positions of F3. The non-randomised DNA-contacting residues carry the nucleotide specificity of the parental Zif268 DNA-binding domain.

The design of the bipartite system features at least two modifications to the conventional zinc finger engineering strategies. As described above, each library contains members that are randomised in the α-helical DNA-contacting residues from more than one zinc finger. We have shown that the simultaneous randomisation of positions from adjacent fingers results in selected zinc finger pairs that can achieve comprehensive DNA recognition, i.e. bind DNA without significant sequence limitations.

The proteins produced by these libraries are therefore not limited to binding DNA sequences of the form GNNGNN..., as is the case with many prior art libraries (e.g. 9, 13, 20).

The repertoire of randomisations does not encode all 20 amino acids, rather representing only those residues that most frequently function in sequence-specific DNA binding from the respective α-helical positions. Excluding the residues that do not frequently function in DNA recognition advantageously helps to reduce the library size and/or the 'noise' associated with non-specific binding members of the library.

The bipartite selection strategy allows the recombination in vitro of the complementary portions of the two libraries, without the need for further purification steps. We take advantage of selective PCR, so as to amplify only the products of recombination. PCR with enzymes lacking 5'→3' exonuclease activity cannot proceed if primers contain one or more 3' mismatches against their template binding sites. The two complementary libraries may therefore be designed with unique sequences at their 5' and 3' termini, and the corresponding primers used to amplify any recombinants of the two libraries. Furthermore, the selection procedure is amenable to a microtitre plate format so that selections and most subsequent manipulations may be automated (e.g., be carried out using liquid handling robots).

Most of the steps of the engineering process using our bipartite protocol—bacterial growth, phage selection, colony picking, phage ELISA, PCR and cloning—may be automated using commercially available instruments. Microtitre plates, such as 96 or 384 well microtitre plates, may be used to carry out phage selections, ELISA reactions and PCR preparation on a liquid-handling robotic platform. A robotic arm shuttles the microtitre plates between a pipeting station, a plate hotel, a plate washer, a spectrophotometer, and a PCR block. A colony picking robot may be used to inoculate micro-cultures of bacteria in microtitre plates in order to provide monoclonal phage for ELISA. A robot may be used that interfaces with the spectrophotometer and which is capable of returning to the liquid culture archive in order to 'cherry-pick' particular clones that are suitable for recombination, or which should be archived. A bar-coding system may be used to keep track of the various plates used for phage selections, phage ELISAs or for archiving interesting clones.

The ability to carry out selective PCR implies that the protocol may even be adapted to selecting complementary library portions in the same tube or well. For example, both universal libraries may be co-screened in a single well, thereby increasing the efficiency of high throughput applications. The output of such combined selections may be monitored by any means, for example, by selective PCR, or by ELISA of samples of isolated clones, etc.

This system is further discussed elsewhere in this application, such as in the Examples section.

In a preferred embodiment, the nucleic acid binding molecules of the invention can be incorporated into an ELISA assay. For example, phage displaying the molecules of the invention can be used to detect the presence of the target nucleic acid, and visualised using enzyme-linked anti-phage antibodies. The sites at which molecules according to the invention bind the target nucleic acid molecule may be determined by methods known in the art for example using binding assays, footprinting, truncation or mutant analysis.

Engineering Zinc Finger Polypeptide Molecules

The engineering of zinc finger polypeptides according to the invention preferably utilises a strategy of engineering zinc finger DNA-binding domains by phage display which has distinct advantages over the existing methods (1, 2), resulting in an advance in our ability to select and/or produce DNA-binding proteins.

Such a strategy can produce zinc fingers binding to diverse DNA sequences, while other methods yield proteins that require the presence of G nucleotide at every third base position (13, 20). This feature is based upon an improvement of our understanding of the synergistic nature of zinc finger interactions, as discussed herein. Prior art techniques have been confined to small subsets of G-rich DNA sequences. The ability to bind a variety of DNA sequences enables targeting of any given promoter in the genome, and is an advantageous feature of at least one aspect of the present invention.

Another advantage of the methods described here is the speed with which DNA-binding domains may be produced. The main reason for the relatively fast turnover is that our new system takes advantage of pre-made phage display libraries, rather than being based on recurring library construction (2)

in order to assemble a zinc finger polymer. This in turn allows for parallel (c.f. serial) selection of zinc fingers from phage display libraries, thus saving time beyond that required simply for cloning. Additionally, the selective PCR protocols allow recombination to be advantageously carried out in vitro using a mixed population of zinc finger phage as starting material, thereby circumventing cumbersome clone isolation, DNA preparation and gel purification procedures. It is envisaged that the methods of the present invention may be useful in high-throughput protein engineering, such as via automation using liquid handling robotic systems.

Nucleic acid binding molecules according to the invention may comprise tag sequences to facilitate studies and/or preparation of such molecules. Tag sequences may include flag-tag, myc-tag, 6his-tag or any other suitable tag known in the art.

Another advantage of the methods described here is the ability to target nucleic acid sequences which comprise cis-acting elements. Examples of cis-acting elements include promoters, enhancers, repressors, transcription factor binding sites, initiators, and other such nucleic acid sequences. Molecules according to the invention may advantageously be targetted to bind at and/or adjacent and/or near to such cis-acting elements. Preferably, molecules according to the invention may be targetted to transcription factor binding sites. By directing or targeting the nucleic acid binding molecules of the invention to nucleic acid sequences in this manner, surprisingly high effects, such as repression effects, may be achieved. This is discussed further below. Such molecules may be advantageously targeted to bind at sites comprising all or part of, or adjacent to, transcription factor sites such as SP1 sites, NF-KB sites, or any other transcription factor binding sites. Preferably, such molecules are targetted to SP1 sites.

Preferably, the DNA-binding domains described herein are highly effective in repressing gene expression from nucleic acid molecules to which they bind. More preferably, the DNA-binding domains described herein are highly effective in repressing gene expression from the HIV-1 promoter. In a highly preferred embodiment, said repression of gene expression involves the binding of said DNA-binding domains to one or more region(s) of the HIV-1 promoter comprising or adjacent to one or more SP1 transcription factor binding site(s).

Advantageously, molecules according to the invention be used in combination. Use in combination includes both fusion of molecules into a single polypeptide as well as use of two or more discrete polypeptide molecules in solution.

The transcription factor binding site may be a binding site for a known transcription factor. The transcription factor may be an animal, preferably vertebrate, or plant transcription factor. Such transcription factors, and their putative or determined binding sites, including any consensus motifs, are known in the art, and may be found in (for example), the "Transcription Factor Database", at hsc.virginia-.edu/achs/molbio/databases/tfd_dat.html. Reference is also made to Nucleic Acids Res 21, 3117-8 (1993), Gene Transcription: A Practical Approach, 321-45 (1993) and Nucleic Acids Res 24, 238-41 (1996). A list of transcription factors, together with their binding sites, is contained in the file "tfsites.daf", is a composite of the datasets TFD (release 7.5) SITES dataset file, 3/96 and Transfac (release 2.5) SITES dataset selected entries, 1/96. The file "tfsites.dat" may be obtained using the GCG command "FETCH tfsites.dat". Any of these binding sites may be targeted according the invention. Preferred transcription factors include those comprising homeodomains. Specific transcription factors and sites include those for NF-kB (GGGAAATTCC), Sp1 (consensus sequence G/T-GGGCGG-GIA-G/A-C/T) Oct-1 (ATTTGCAT), p53, myC, myB, AP1 etc.

Pharmaceuticals

Moreover, the invention provides therapeutic agents and methods of therapy involving use of nucleic acid binding proteins as described herein. In particular, the invention provides the use of polypeptide fusions comprising an integrase, such as a viral integrase, and a nucleic acid binding protein according to the invention to target nucleic acid sequences in vivo (Bushman, (1994) PNAS (USA) 91:9233-9237). In gene therapy applications, the method may be applied to the delivery of functional genes into defective genes, or the delivery of nonsense nucleic acid in order to disrupt undesired nucleic acid Alternatively, genes may be delivered to known, repetitive stretches of nucleic acid, such as centromeres, together with an activating sequence such as an LCR This would represent a route to the safe and predictable incorporation of nucleic acid into the genome.

In conventional therapeutic applications, nucleic acid binding proteins according to the invention may be used to specifically knock out cell having mutant vital proteins. For example, if cells with mutant ras are targeted, they will be destroyed because ras is essential to cellular survival. Alternatively, the action of transcription factors may be modulated, preferably reduced, by administering to the cell agents which bind to the binding site specific for the transcription factor. For example, the activity of HIV tat may be reduced by binding proteins specific for HIV TAR.

Moreover, binding proteins according to the invention may be coupled to toxic molecules, such as nucleases, which are capable of causing irreversible nucleic acid damage and cell death. Such agents are capable of selectively destroying cells which comprise a mutation in their endogenous nucleic acid.

Nucleic acid binding proteins and derivatives thereof as set forth above may also be applied to the treatment of infections and the like in the form of organism-specific antibiotic or antiviral drugs. In such applications, the binding proteins may be coupled to a nuclease or other nuclear toxin and targeted specifically to the nucleic acids of microorganisms.

The invention likewise relates to pharmaceutical preparations which contain the compounds according to the invention or pharmaceutically acceptable salts thereof as active ingredients, and to processes for their preparation.

The pharmaceutical preparations according to the invention which contain the compound according to the invention or pharmaceutically acceptable salts thereof are those for enteral, such as oral, furthermore rectal, and parenteral administration to (a) warm-blooded animal(s), the pharmacological active ingredient being present on its own or together with a pharmaceutically acceptable carrier. The daily dose of the active ingredient depends on the age and the individual condition and also on the manner of administration.

The novel pharmaceutical preparations contain, for example, from about 10% to about 80%, preferably from about 20% to about 60%, of the active ingredient. Pharmaceutical preparations according to the invention for enteral or parenteral administration are, for example, those in unit dose forms, such as sugar-coated tablets, tablets, capsules or suppositories, and furthermore ampoules. These are prepared in a manner known per se, for example by means of conventional mixing, granulating, sugar-coating, dissolving or lyophilising processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Suitable carriers are, in particular, fillers, such as sugars, for example lactose, sucrose, mannitol or sorbitol, cellulose preparations and/or calcium phosphates, for example tricalcium phosphate or calcium hydrogen phosphate, furthermore binders, such as starch paste, using, for example, corn, wheat, rice or potato starch, gelatin, tragacanth, methylcellulose and/or polyvinylpyrrolidone, if desired, disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropylmethylcellulose phthalate. Colorants or pigments, for example to identify or to indicate different doses of active ingredient, may be added to the tablets or sugar-coated tablet coatings.

Other orally utilisable pharmaceutical preparations are hard gelatin capsules, and also soft closed capsules made of gelatin and a plasticiser, such as glycerol or sorbitol. The hard gelatin capsules may contain the active ingredient in the form of granules, for example in a mixture with fillers, such as lactose, binders, such as starches, and/or lubricants, such as talc or magnesium stearate, and, if desired, stabilisers. In soft capsules, the active ingredient is preferably dissolved or suspended in suitable liquids, such as fatty oils, paraffin oil or liquid polyethylene glycols, it also being possible to add stabilisers.

Suitable rectally utilisable pharmaceutical preparations are, for example, suppositories, which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons. Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilisers.

The dose of the active ingredient depends on the warm-blooded animal species, the age and the individual condition and on the manner of administration. In the normal case, an approximate daily dose of about 10 mg to about 250 mg is to be estimated in the case of oral administration for a patient weighing approximately 75 kg

EXAMPLES

Example 1

Zinc Finger Engineering Strategy (CXCR4 and TNFR1)

Sequences situated within the previously described minimal promoter and comprising the GC I box, the NRF-1 site and the TATA box are targeted (position −73 to −30). Zinc fingers are engineered to bind to the CXCR4 promoter using the 'bipartite' method described above and in WO98/53057. The bipartite method is based on a pair of pre-made zinc finger phage display libraries, which are used in parallel to select two DNA-binding domains that each recognise given 5 bp sequences, and whose products are recombined to produce a single protein that recognises a composite (9-10 bp) site of predefined sequence. Engineering using this system can be completed in less than two weeks and yields three-zinc finger polypeptide molecules that bind sequence-specifically to DNA with Kds in the nanomolar range. Having thus obtained three-zinc finger molecules, the genes for these peptides are linked together to make functional six-zinc finger proteins. In the present case, we generate three such six-zinc finger proteins, engineered to bind a promoter sequence of the CXCR4 receptor.

A similar strategy is used to generate three and six finger proteins engineered to bind a promoter sequence of the TNFR1 receptor.

Zinc finger proteins selected to bind to the CXCR4 or the TNFR1 promoter regions are then engineered into repressor polypeptides. These repressors contain the zinc finger DNA binding domain at the N-terminus fused in frame to the translation initiation sequence ATG. The 7 amino acid nuclear localisation sequence (NLS) of the wild-type Simian Virus 40 large-T antigen (Kalderon et al., Cell 39:499-509 (1984)) is fused to the C-terminus of the zinc finger sequence and the Kruppel-associated box (KRAB) repressor domain from human KOX1 protein (Margolin et al., PNAS 91:4509-4513 (1994)) is fused downstream of the NLS.

The sequence of the SV40-NLS-KOX1-c-myc repressor domain (NLS-KOX1-c-myc domain sequence) is as follows:

(SEQ ID NO: 27)
AARNSGPKKKRKVDGGGALSPQHSAVTQGSIIKNKEGMDAKSLTAWSRTL

VTFKDVFVDFTREEWKLLDTAQQIVYRNVMLENYKNLVSLGYQLTKPDVI

LRLEKGEEPWLVEREIHQETHPDSETAFEIKSSVEQKLISEEDL

The KOX1 domain contains amino acids 1-97 from the human KOX1 protein (database accession code P21506) in addition to 23 amino acids which act as a linker. In addition, a 10 amino acid sequence from the c-myc protein (Evan et al., Mol. Cell. Biol. 5: 3610 (1985)) is introduced downstream of the KOX1 domain as a tag to facilitate expression studies of the fusion protein.

Zinc finger constructs are then tested for specific target binding using a fluorescence ELISA, and for repression activity using FACS analysis.

Example 2

Sequences of Binding-Sites and Composition of Zinc Fingers Engineered Against the CXCR4 Gene Promoter A. DNA Binding Sites in the CXCR4 Promoter DNA sequences in the promoter region of the CXCR4 gene showing 9-bp binding sites (underlined), that are used as targets for engineering 3-finger proteins using the 'bipartite' protocol, are shown below. The resulting three-zinc finger proteins, that bind the 9-bp sites, are paired to generate the six-zinc finger proteins, CXCR4-5-1, CXCR4-10-1 and CXCR4-10-3, that bind 18-bp sites (underlined).

Sequence targeted within the CXCR4 promoter (position −73 to −30).

(SEQ ID NO: 28)
5'-TCCCCGCCCCAGCGGCGCATGCGCCGCGCTCGGAGCGTGTTTTTATA-3'

CXCR4-5-1
(SEQ ID NO: 29)
5'-CCGCCCCAGCGGCGCATGCGCCGCGCTCGGAGCGTGTT-3'
     1                5

CXCR4-10-1
(SEQ ID NO: 30)
5'-CCGCCCCAGCGGCGCATGCGCCGCGCTCGGAGCGTGTT-3'
     1                    10

CXCR4-10-3
(SEQ ID NO: 31)
5'-CCGCCCCAGCGGCGCATGCGCCGCGCTCGGAGGCGTGTT-3'
         3                    10

B. Zinc Finger Protein Sequences

Amino acid sequences of the helical regions from recombinant six-zinc finger DNA-binding domains engineered against the CXCR4 gene promoter. Residues are numbered relative to the first position in the a-helix (position 1) in each finger (F1-6).

CXCR4-5-1 (Linker A TGGGGSGGSGGSERP (SEQ ID NO:51) Between F3 and F4)

| F1 | F2 | F3 | F4 | F5 | F6 |
|---|---|---|---|---|---|
| CXCR4-5-1 (Linker A TGGGGSGGSGGSERP (SEQ ID NO: 51) between F3 and F4) | | | | | |
| −1123456 DSATLTE (SEQ ID NO: 32) | −1123456 RRDDLSR (SEQ ID NO: 33) | −1123456 RKSDRTR (SEQ ID NO: 34) | −1123456 RSDELTR (SEQ ID NO: 35) | −1123456 RSDTLSK (SEQ ID NO: 36) | −1123456 QKHDRTQ (SEQ ID NO: 37) |
| CXCR4-10-1 (Linker B TGGGGSGGSGGSGGSGGSERP (SEQ ID NO: 52) between F3 and F4) | | | | | |
| −1123456 KSNDLIR (SEQ ID NO: 38) | −1123456 QSAHLSR (SEQ ID NO: 39) | −1123456 DNRDRTK (SEQ ID NO: 40) | −1123456 RSDELTR (SEQ ID NO: 35) | −1123456 RSDTLSK (SEQ ID NO: 36) | −1123456 QKHDRTQ (SEQ ID NO: 37) |
| CXCR4-10-3 (Linker B TGGGGSGGSGGSGGSGGSERP (SEQ ID NO: 52) between F3 and F4) | | | | | |
| −1123456 KSNDLIR (SEQ ID NO: 38) | −1123456 QSAHLSR (SEQ ID NO: 39) | −1123456 DNRDRTK (SEQ ID NO: 40) | −1123456 RSTDLIR (SEQ ID NO: 47) | −1123456 TSSNLSA (SEQ ID NO: 48) | −1123456 RNADRTK (SEQ ID NO: 49) |

C. Peptide Linkers Between Fingers 3 and 4

Amino acid composition of peptide linkers (A and B), used to link the three-finger units shown above into six-finger constructs. Different lengths of linker are used to span different lengths of gap between the binding sites of the subunits.

| | |
|---|---|
| Wild-type linker =TGERP | (SEQ ID NO: 50) |
| LINKER-A =TGGGGSGGSGGSERP | (SEQ ID NO: 51) |
| LINKER-B =TGGGGSGGSGGSGGSGGSERP | (SEQ ID NO: 52) |

D. Sequences of CXCR4 Six Finger Domains

CXCR4 5-1
(SEQ ID NO: 53)
MAERPYACPVESCDRRFSDSATLTEHIRIHTGQKPFQCRICMRNFSRRDD

LSRHIRTHTGEKPFACDICGRKFARKSDRTRHTKIHTGGGGSGGSGGSER

PYACPVESCDRRFSRSDELTRHIRIHTGQKPFQCRICMRNFSRSDTLSKH

IRTHTGEKPFACDICGRKFAQKHDRTQHTKIHLRQKD

CXCR4-10-1
(SEQ ID NO: 54)
MAERPYACPVESCDRRFSKSNDLIRHIRIHTGQKPFQCRICMRNFSQSAH

LSRHIRTHTGEKPFACDICGRKFADNRDRTKHTKIHTGGGGSGGSGGSGG

SGGSERPYACPVESCDRRFSRSDELTRHIRIHTGQKPFQCRICMRNFSRS

DTLSKHIRTHTGEKPFACDICGRKFAQKHDRTQHTKIHLRQKD

CXCR4 10-3
(SEQ ID NO: 55)
MAERPYACPVESCDRRFSKSNDLIRHIRIHTGQKPFQCRICMRNFSQSAH

LSRHIRTHTGEKPFACDICGRKFADNRDRTKHTKIHTGGGGSGGSGGSGG

SGGSERPYACPVESCDRRFSRSTDLIRHIRIHTGQKPFQCRICMRNFSTS

SNLSAHIRTHTGEKPFACDICGRKFARNADRTKHTKIHLRQKD

E. Sequences of Constructs Comprising Repressor Domains

CXCR4 5-1 +Repressor
(SEQ ID NO: 56)
MAERPYACPVESCDRRFSDSATLTEHIRIHTGQKPFQCRICMRNFSRRDD

LSRHIRTHTGEKPFACDICGRKFARKSDRTRHTKIHTGGGGS-GGSGGSER

PYACPVESCDRRFSRSDELTRHIRIHTGQKPFQCRICMRNFSRSDTLSK-H

IRTHTGEKPFACDICGRKFAQKHDRTQHTKIHLRQKDAARNSGPKKKRKV

DGGGALSPQHSAVTQGSIIKNKEGMDAKSLTAWSRTLVTFKDVFVDFTRE

EWKLLDTAQQIVYRNVMLENYKNLVSLGYQLTKPDVILRLEKGEEPWLVE

REIHQETHPDSETAFEIKSSVEQKLISEEDL

CXCR4-10-1 +Repressor
(SEQ ID NO: 57)
MAERPYACPVESCDRRFSKSNDLIRHIRIHTGQKPFQCRICMRNFSQSAH

LSRHIRTHTGEKPFACDICGRKFADNRDRTKHTKIETGGGGSGGSGGSGG

SGGSERPYACPVESCDRRFSRSDELTRHIRIHTGQKPFQCRICMRNFSRS

DTLSKHIRTHTGEKPFACDICGRKFAQKHDRTQHTKIHLRQKDAARNSGP

KKKRKVDGGGALSPQHSAVTQGSIIKNKEGMDAKSLTAWSRTLVTFKDVF

VDFTREEWKLLDTAQQIVYRNVMLENYKNLVSLGYQLTKPDVILRLEKGE

EPWLVEREIHQETHPDSETAFEIKSSVEQKLISEEDL

CXCR4-10-3 +Repressor
(SEQ ID NO: 58)
MAERPYACPVESCDRRFSKSNDLIRHIRIHTGQKPFQCRICMRNFSQSAH

LSRHIRTHTGEKPFACDICGRKFADNRDRTKHTKIHTGGGGSGGSGGSGG

SGGSERPYACPVESCDRRFSRSTDLIRHIRIHTGQKPFQCRICMRNFSTS

SNLSAHIRTHTGEKPFACDICGRKFARNADRTKHTKIHLRQKDAARNSGP

KKKRKVDGGGALSPQHSAVTQGSIIKNKEGMDAKSLTAWSRTLVTFKDVF

VDFTREEWKLLDTAQQIVYRNVMLENYKNLVSLGYQLTKPDVILRLEKGE

EPWLVEREIHQETHPDSETAFEIKSSVEQKLISEEDL

Example 3

Sequences of Binding-Sites and Composition of Zinc Fingers Engineered Against the TNFR1 Gene Promoter

A. DNA Binding Sites in the TNFR1 Promoter

DNA sequences in the promoter region of the TNFR1 gene showing 9-bp binding sites (underlined), that are used as targets for engineering 3-finger proteins using the 'bipartite' protocol, are shown below. The resulting three-zinc finger proteins that bind the 9-bp sites, are paired to generate the six-zinc finger proteins, TNFR1-4-2, TNFR1-7-9, TNFR1-7-10 and TNFR1-9-12.

Sequences Targeted within the TNFR1 Promoter

-331 GCCTCCTCCTCCCGCCTCCTGTGGCCTCCTCCTCCAGCTCTTCCTGTCCCGCTG -278 (SEQ ID NO: 59)
(REF. 25)

-420 TGGTCGGATTGGTGGGTTGGGGGCACAAGGCA -389 (REF. 25)  (SEQ ID NO: 60)

TNFR1-4-2
5'GTCGGATTGGTGGGTTGGGGGCACAAGGCA-3' (TNFR1-4-2, SEQ ID NO: 61)

TNFR1-7-9 and TNFR1-7-10
5'TGGAGGAGGAGGCCACAGGAGGCGGGAGGA-3' (RNFR1-7-9; TNFR1-7-10, SEQ ID NO: 62)

TNFR1-9-12
5'CAGGAAGAGCTGGAGGAGGAGGCCCACAGGA-3' (TNFR1-9-12, SEQ ID NO: 63)

TNFR-1-4-2 recognises underlined sites in GG ATTGGTGGG TTGGGGGCACA (SEQ ID NO:64); TNFR1-7-9 and TNFR1-7-10 recognise underlined sites in C CGCCTCCTGTGGCCTCCTCC (SEQ ID NO:65); and TNFR1-9-12 recognises underlined sites in GT GGGCCTCCTCCTCCAGCTCTT (SEQ ID NO:66)

B. Zinc Finger Protein Sequences

Amino acid sequences of the helical regions from recombinant six-zinc finger DNA-binding domains engineered against the TNFR1 gene promoter. Residues are numbered relative to the first position in the a-helix (position 1) in each finger (F1-6).

| F1 | F2 | F3 | F4 | F5 | F6 |
|---|---|---|---|---|---|
| TNFR1-4-2 (Linker TGSERP (SEQ ID NO: 120) between F3 and F4) | | | | | |
| −1123456 ASADLTR (SEQ ID NO: 67) | −1123456 RRDHLSE (SEQ ID NO: 68) | −1123456 RNDSRTN (SEQ ID NO: 69) | −1123456 RSQHLTE (SEQ ID NO: 70) | −1123456 TSSHLSV (SEQ ID NO: 71) | −1123456 HSNARKT (SEQ ID NO: 72) |
| TNFR1-7-9 (Linker TGGGGSERP (SEQ ID NO: 121) between F3 and F4) | | | | | |
| −1123456 RSDELTR (SEQ ID NO: 73) | −1123456 RSDNLSE (SEQ ID NO: 74) | −1123456 RSDNRKT (SEQ ID NO: 75) | −1123456 DNRDLIR (SEQ ID NO: 76) | −1123456 RSDDLSR (SEQ ID NO: 77) | −1123456 RSDNRTK (SEQ ID NO: 78) |
| TNFR1-9-12 (Linker TGGGGSERP (SEQ ID NO: 121) between F3 and F4) | | | | | |
| −1123456 DNRDLIR (SEQ ID NO: 79) | −1123456 RSDDLSR (SEQ ID NO: 80) | −1123456 RSDNRTK (SEQ ID NO: 81) | −1123456 DSAHLIR (SEQ ID NO: 82) | −1123456 TSSDLSR (SEQ ID NO: 83) | −1123456 QSAHRKT (SEQ ID NO: 84) |
| TNFR1-7-10 (Linker TGGGGSGGSERP (SEQ ID NO: 122) between F3 and F4) | | | | | |
| −1123456 RSDELTR (SEQ ID NO: 85) | −1123456 RSDNLSE (SEQ ID NO: 86) | −1123456 RSDNRKT (SEQ ID NO: 87) | −1123456 DNRDLIR (SEQ ID NO: 88) | −1123456 RSDDLSR (SEQ ID NO: 89) | −1123456 RSDNRTK (SEQ ID NO: 90) |

Amino acid linkers as shown above are used to link the three-finger units shown above into six-finger constructs. Different lengths of linker are used to span different lengths of gap between the binding sites of the subunits.

C. Sequences of TNFR1 Six Finger Domains

TNFR1-4-2, recognising GGATTGGTGGG TTGGGGGCACA (SEQ ID NO: 123)

(SEQ ID NO: 91)
```
  1    M A H R P Y A C P V E S C D R
 16    R F S A S A D L T R H I R I H
 31    T G Q K P F Q C R I C M R N F
 46    S R R D H L S E H I R T H T G
 61    E K P F A C D I C G R K F A R
 76    N D S R T N H T K I H T G S E
 91    R P Y A C P V H S C D R R F S
106    R S Q H L T E H I R I H T G Q
121    K P F Q C R I C N R N F S T S
136    S H L S V H I R T H T G H K P
151    F A C D I C G R K F A H S N A
166    R K T H T K I H L R Q K D
```

TNFR1-7-9, recognising CCGCCTCCTGTGGCCTCCTCC (SEQ ID NO: 117)

(SEQ ID NO: 92)
```
  1    N A E R P Y A C P V H S C D R
 16    R F S R S D E L T R H I R I H
 31    T G Q K P F Q C R I C M R N F
 46    S R S D N L S E H I R T H T G
 61    H K P F A C D I C G R K F A R
 76    S D N R K T H T K I H T Q G G
 91    G S E R P Y A C P V H S C D R
106    R F S D N R D L I R H I R I H
121    T G Q K P F Q C R I C N R N F
136    S R S D D L S R H I R T H T G
151    E K P F A C D I C G R K F A R
166    S D N R T K H T K I H L R Q K
181    D
```

TNFR1-9-12, recognising GTGGCCTCCTCCTCCAGCTCTT (SEQ ID NO: 118)

(SEQ ID NO: 93)
```
  1    N A H R P Y A C P V E S C D R
 16    R F S D N R D L I R H I R I H
 31    T G Q K P F Q C R I C N R N F
 46    S R S D D L S R H I R T H T G
 61    E K P F A C D I C G R K F A R
 76    S D N R T K H T K I H T G G G
 91    G S E R P Y A C P V H S C D R
```

```
106     R F S D S A H L I R H I R I H
121     T G Q K P F Q C R I C M R N F
136     S T S S D L S R H I R T H T G
151     E K P F A C D I C G R K F A Q
166     S A H R K T H T K I H L R Q K
181     D
```

TNFR1-7-10, recognising CCGCCTCCTGTGGCCTCCTCC
(SEQ ID NO: 119)

(SEQ ID NO: 94)
```
  1     N A H R P Y A C P V E S C D R
 16     R F S R S D E L T R H I R I H
 31     T G Q K P F Q C R I C N R N F
 46     S R S D N L S E H I R T H T G
 61     E K P F A C D I C G R K F A R
 76     S D N R K T H T K I H T G G G
 91     G S G G S E R P Y A C P V E S
106     C D P R F S D N P D L I R H I
121     R I H T G Q K P F Q C P I C M
136     R N F S P S D D L S R H I P T
151     H T G E K P F A C D I C G R K
166     F A R S D N R T K H T K I H L
181     R Q K D
```

D. Sequences of Constructs Comprising Repressor Domains (Linkers Underlined)

TNFR1-4-2 +Repressor
(SEQ ID NO: 95)
MAERPYACPVESCDRRFSASADLTRHIRIHTGQKPFQCRICMRNFSRRDHLSEHIRTETGEKPFACDIC
GRKFARNDSRTNHTKIH<u>TGSERP</u>YACPVESCDRRFSRSQHLTEHIRIHTGQKPFQCRICMRNFSTSSHL
SVHIRTHTGEKPFACDICGRKFAHSNARXTHTKIHLRQKD**AARNSGPKRKRKVDGGGALSPQHSAVTQG
SIIKNKEGMDAKSLTAWSRTLVTFKDVFVDFTREEWKLLDTAQQIVYRNVMLENYKNLVSLGYQLTKPD
VILRLEKGEEPWLVEREIHQETHPDSETAFEIKSSVEQKLISEEDL**

TNFR1-7-9 +Repressor
(SEQ ID NO: 96)
MAERPYACPVESCDRRFSRSDELTRHIRIHTGQKPFQCRICMRNFSRSDNLSEHIRTHTGEKPFACDIC
GRKFARSDNRKTHTKIH<u>TGGGSERP</u>YACPVESCDRRFSDNRDLIRHIRIHTGQKPFQCRICMRNFSRS
DDLSRHIRTHTGEKPFACDICGRKFARSDNRTKHTKIHLRQKD**AARNSGPKKKRXVDGGGALSPQHSAV
TQGBIIKNKEGMDAXSLTAWSRTLVTFKDVFVDFTREEWKLLDTAQQIVYENVMLENYKNLVSLGYQLT
KPDVILRLEKGEEPWLVEREIHQETHPDSETAFEIKSSVEQKLISEEDL**

TNFR1-9-12 +Repressor
(SEQ ID NO: 97)
MAERPYACPVESCDERFSDNRDLIRHIRIHTGQKPFQCRICMRNFSRSDDLSRHIRTHTGEKPFACDIC
GRKFARSDNRTKHTKIH<u>TGGGSERP</u>YACPVESCDRRFSDSAHLIRHIRIHTGQKPFQCRICMRNFSTS
SDLSRHIRTRTGEKPFACDICGRKFAQSAHRKTHTKIBLRQKD**AARNSGPKKKEXVDGGGALSPQHSAV
TQGSIIKNKEGMDAKSLTAWSRTLVTFKDVFVDFTRBEWKLLDTAQQIVYRNVMLENYKNLVSLGYQLT
KPDVILRLEKGEEPWLVEREIHQETHPDSETAFEIKSSVEQKLISEEDL**

TNFR1-7-10 +Repressor
(SEQ ID NO: 98)
MAERPYACPVESCDRRFSRSDELTRHIRIHTGQKPFQCRICMRNFSRSDNLSEHIRTHTGEKPFACDIC
GRKFARSDNRKTHTKIHTGGGSGGSERPYACPVESCDRRFSDNRDLIRHIRIHTGQKPFQCRICMRNF
SRSDDLSRHIRTHTGEKPFACDICGRKFARSDNRTKHTKIHLRQKD**AARNSGPKKKEKVDGGGALSPQH
SAVTQGSIIKNKEGMDAKSLTAWSRTLVTFKDVFVDFTREEWKLLDTAQQIVYRNVMLENYKNLVSLGY
QLTKPDVILRLEKGEEPWLVEREIHQETHPDSETAFEIKSSVEQKLISEEDL**

Example 4

Experimental Protocol for In Vitro Fluorescence ELISA

The binding properties of the six-finger proteins are assayed using an in vitro zinc finger fluorescence ELISA DNA-binding assay to assess whether the proteins bind specifically to their respective target sequences.

Preparation of Template

Zinc finger constructs are inserted into the protein expression vector pTracer (Invitrogen), downstream of the T7 RNA transcription promoter. Suitable templates for in vitro ELISA are created by PCR using the 5' primer (GCA-GAGCTCTCTGGCTAACTAGAG, SEQ ID NO:99), which binds upstream of the T7 promoter and a 3' primer, which binds to the 3' end of the zinc finger construct and adds a sequence encoding for the HA-antibody epitope tag (YPYD-VPDYA, SEQ ID NO:100)

Zinc Finger Expression

In vitro transcription and translation are performed using the T7 TNT Quick Coupled Transcription/Translation System for PCR templates (Promega), according to the manufacturers instructions, except that the medium is supplemented with 500 µM $ZnCl_2$.

Fluorescence ELISA

DNA binding reactions contained the appropriate zinc finger peptide, biotinylated binding site (10 nM) and 5 µg competitor. DNA (sonicated salmon sperm DNA), in a total volume of 50 µl, which contained: 1×PBS (pH 7.0), $1.25 \times 10^{-3}$ U high affinity anti-HA-Peroxidase antibody (Boehringer Mannheim), 50 µM $ZnCl_2$, 0.01 mg/ml BSA, and 0.5% Tween 20. Incubations are performed at room temperature for 40 minutes. Black streptavidin-coated wells are blocked with 4% marvel for 1 hour. Binding reactions are added to the streptavidin-coated wells and incubated for a further 40 minutes at room temperature. Wells are washed 5 times in 100 µl wash buffer (1×PBS (pH 7.0), 50 µM $ZnCl_2$, 0.01 mg/ml BSA, and 0.5% Tween 20), and finally 50 µl QuantaBlu peroxidase substrate solution (Pierce) is added to detect bound HA-tagged zinc finger peptide. ELISA signals are read in a SPECTRAmax GeminiXS spectrophotometer (Molecular Devices) and analysed using SOFTmax Pro 3.1.2 (Molecular Devices).

Example 5

Experimental Protocol for Transient Assay (FACS)

Jurkat T cells are grown according to supplier instructions in RPMI 1640 L-glutamine containing medium (Life Technology) supplemented with penicillin/streptomycin and fetal calf serum. $5 \times 10^6$ cells in 0.2 ml of culture medium are transfected in a 0.4 cm gap electroporation cuvette at 0.20 kV and 960 µF with 20 µg pTracerTM-CMV/Bsd zinc finger expressing plasmid. An empty pTracerTM-CMV/Bsd vector plasmid is used as control. The electroporated samples are transferred to 27 $cm^2$ cell culture flask containing 30 ml Jurkat T cell growth media and incubated for 24 to 72 hours at 37° C. and 5% $CO_2$.

Cells are harvested and pelleted at 1000 rpm for 5 minutes at room temperature. Pellets are resuspended in ice-cold 50 µl staining buffer (PBS, 0.5% BSA, 0.01% sodium azide) and incubated for 30 minutes on ice with saturating amounts of antibodies.

To assess for CXCR4 expression, cells are stained with biotinylated mouse-anti-human CXCR4 antibody (clone 44716.111 or clone 44717.111, R&Dsystem, dilution 1:10 in staining buffer) which is detected with streptavidin-PE (R&Dsystem, dilution 1:20 in staining buffer).

To assess for TNFR1 expression, cells are stained with a mouse-anti-human TNFR1 antibody (550514, Pharmingen, 1:25 dilution), which is then bound by a biotinylated anti-mouse IgG, Fab-specific (Sigma), and detected with streptavidin-Cychrome (Pharmingen).

Between each step, cells are pelleted at 1000 rpm for 5 minutes and washed twice in 150 µl ice-cold staining buffer. Flow cytometric analysis is performed on a FACSCalibur using the CellQuest software package (Becton Dickinson). About 300,000 events corresponding to 15,000 events gated on GFP positive cells are collected per sample.

Example 6

DNA-Binding by CXCR4 Constructs Using an In Vitro Fluorescence ELISA Assay

Zinc finger peptides are expressed using the T7 TNT Quick Coupled Transcription/Translation System for PCR templates (Promega) and assayed for DNA-binding by fluorescence ELISA (see above; FIG. 1). Binding is plotted vertically, on a relative scale. Sequences of the DNA target sites used in each binding reaction are shown below the figure. Bases expected to be in the linker region between F3 and F4 are indicated by brackets [eg (cat)].

Figure 1C:
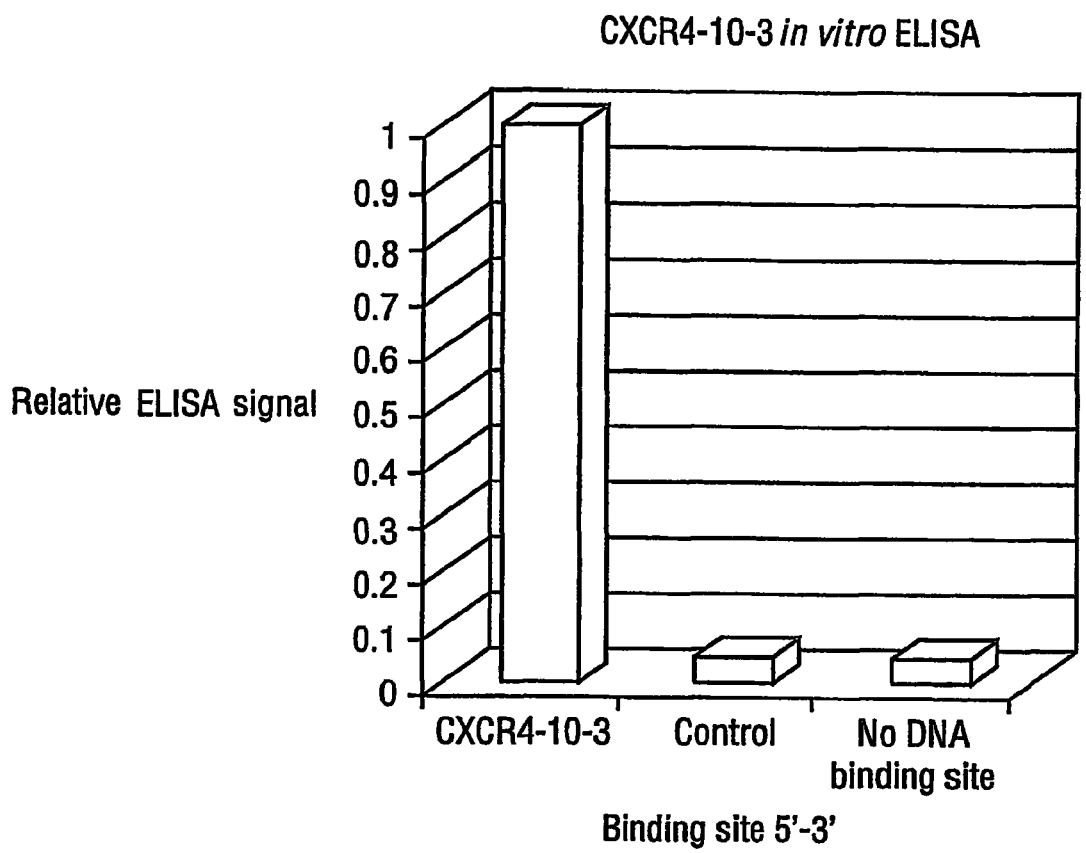

FIG. 1A shows binding of the six-zinc finger peptide, CXCR4-5-1, to its preferred target site and to 5 control sites containing base mutations (underlined). FIG. 1B shows binding of the six-zinc finger peptide, CXCR4-10-1, to its preferred target site and to a control site containing base mutations (underlined). FIG. 1C shows binding of the six-zinc finger peptide, CXCR4-10-3, to its preferred target site and to a control site containing base mutations (underlined).

The above assays reveal that the proteins bind specifically to their respective target sequences.

Example 7

Specific Down-Regulation of Endogenous CXCR4 by Selected Zinc Finger Proteins (FACS Analysis)

The Jurkat T-cell line is a human derived lymphoblast T cell shown to express high levels of CXCR4 receptor. This line is used to validate the ability of selected zinc finger protein to control the expression of CXCR4 receptor. Using fluorescence activated cell sorting (FACS), the Jurkat T-cell line is used in a transient transfection assay to validate the selected zinc finger constructs.

The zinc finger constructs containing the repressor domain, generated as described above, are subcloned in the pTracerTM-CMV/Bsd plasmid vector (Invitrogen) for expression in Jurkat T cells. Expression of the zinc finger protein in transfected cells is monitored by the co-expression of the green fluorescent protein (GFP) gene also encode by the pTracerTM-CMV/Bsd plasmid vector. An empty pTracerTM-CMV/Bsd plasmid vector are used as a control. Jurkat T cells are transfected by electroporation and after 24 to 72 hours, CXCR4 expression is assay by fluorescence activated cell sorting (FACS) analysis.

Figure 2A:
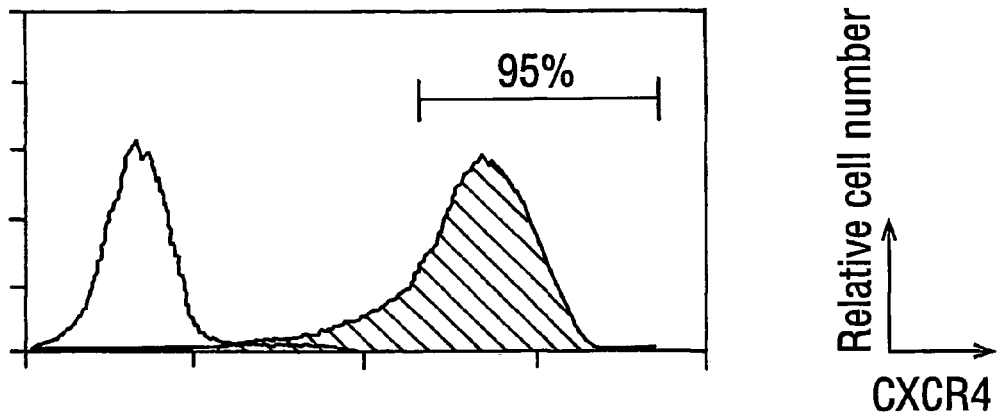
FIGS. 2A, 2B and 2C show specific down-regulation of endogenous CXCR4 by selected zinc finger protein.

Expression of CXCR4 at the surface of Jurkat cells is first measured, and the results are as shown in FIG. 2A. $10^6$ cells are stained with biotinylated mouse-anti-human CXCR4 antibody which is subsequently detected with streptavidin- PE. Unstained cells are used as control (unfilled). 95% of Jurkat expressed CXCR4 at their surface.

Figure 2C:
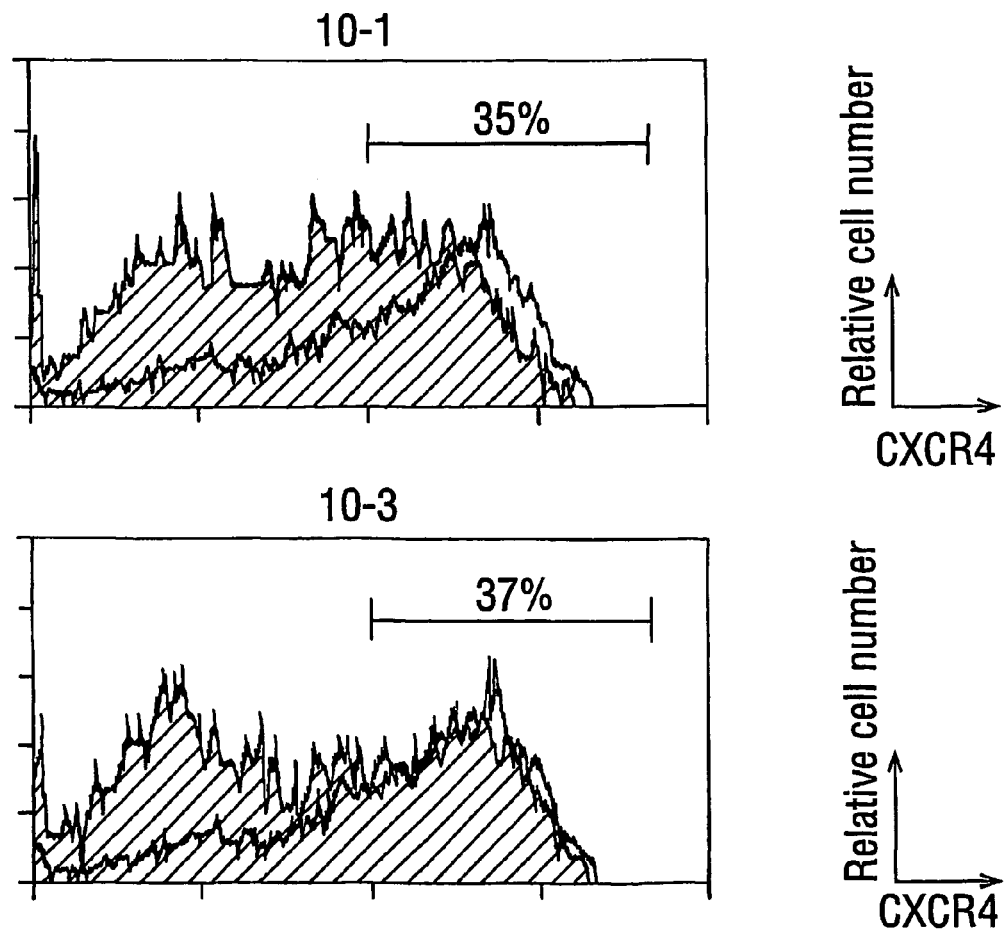
Figure 2B:
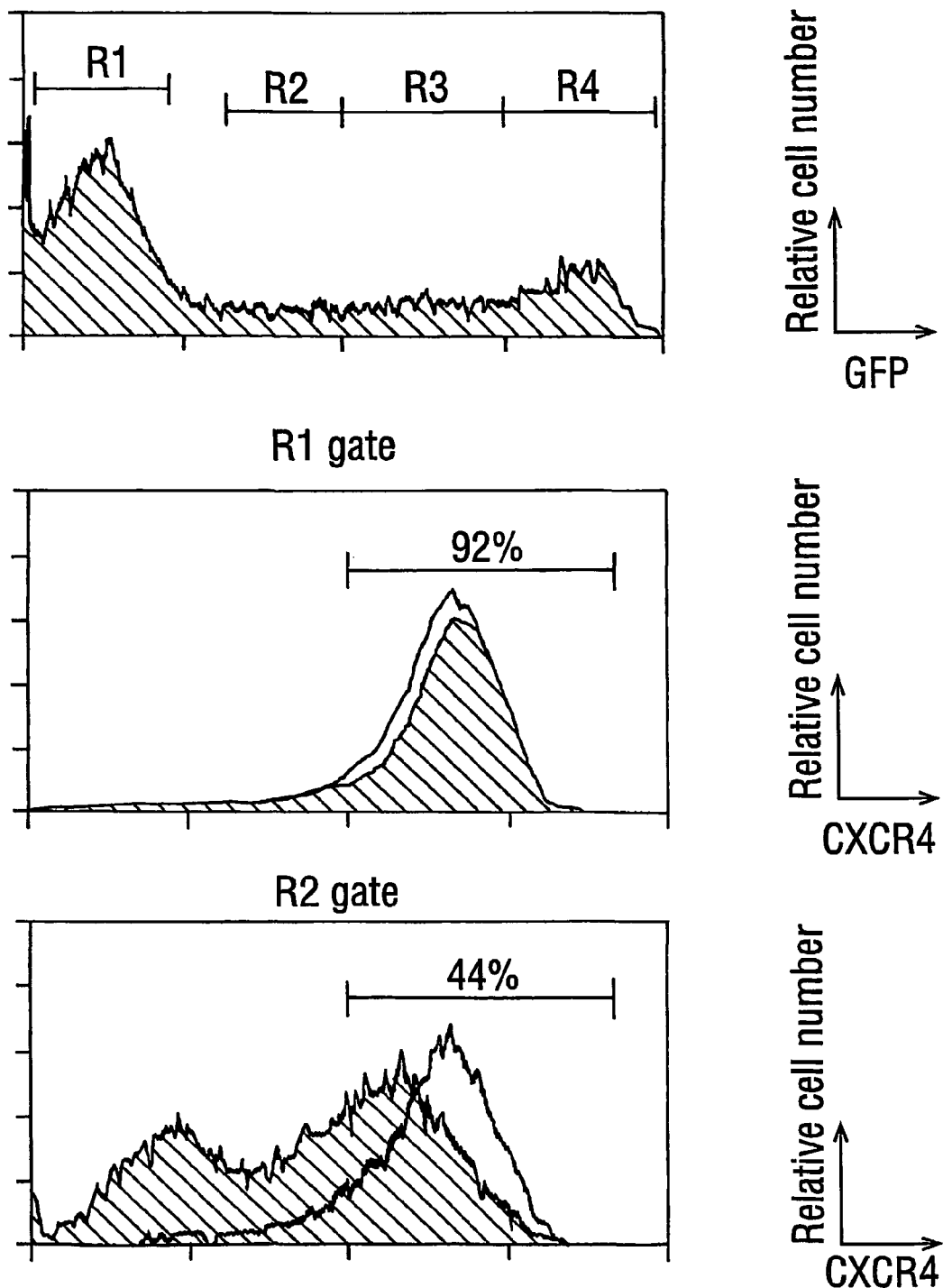

FIG. 2B shows the results of experiments in which Jurkat T-cells are transfected by electroporation with pTracerTM-CMV/Bsd zinc finger expressing plasmid. An empty pTracerTM-CMV/Bsd plasmid is used as control. From 24 hours post transfection, the expression of the zinc finger protein 5-1 is monitored by expression of GFP. Expression of CXCR4 is assess by FACS analysis on different population: non-transfected Jurkat cells which represent an internal control (R1) and sub populations R2, R3 and R4 exhibited 10-, 100- and 1000-fold higher GFP fluorescence intensity relative to background, respectively. As expected the population R1 expressed high levels of CXCR4, which was comparable to cells transduced with the empty pTracer (unfilled). Population R2, R3 and R4 present a specific inhibition of CXCR4 expression, compared to the control (unfilled), which seems to correlate with the level of expression of the zinc finger. The percentage of cells expressing CXCR4 is shown.

FIG. 2C shows that downregulation of CXCR4 is also observed with Jurkat cells transfected with zinc finger proteins 10-1 and 10-3, compared to the cell transfected with an empty control vector (unfilled). The percentage of cells expressing CXCR4 is shown.

The expression of zinc fingers 5-1, 10-1 and 10-3, monitored by the GFP expression, in transfected Jurkat cells results in the specific down-regulation of CXCR4 in comparison to the control. Moreover the down-regulation of CXCR4 on transduced Jurkat cells by the zinc finger protein 5-1 is also observed at low level of expression, relative to GFP expression which presume to high binding specificity of this zinc finger on its endogenous target sequence. Exposure of such transfected cells to HIV results in lower levels of infection and viral titre than in un-transfected cells.

Example 8

DNA-Binding by TNFR1 Constructs Using an In Vitro Fluorescence ELISA Assay

Zinc finger peptides are expressed using the T7 TNT Quick Coupled Transcription/Translation System for PCR templates (Promega) and assayed for DNA-binding by fluorescence ELISA, as described above in Examples 4 and 6. Sequences of the DNA target sites used in each binding reaction are shown below FIG. 3A.

Figure 3A:
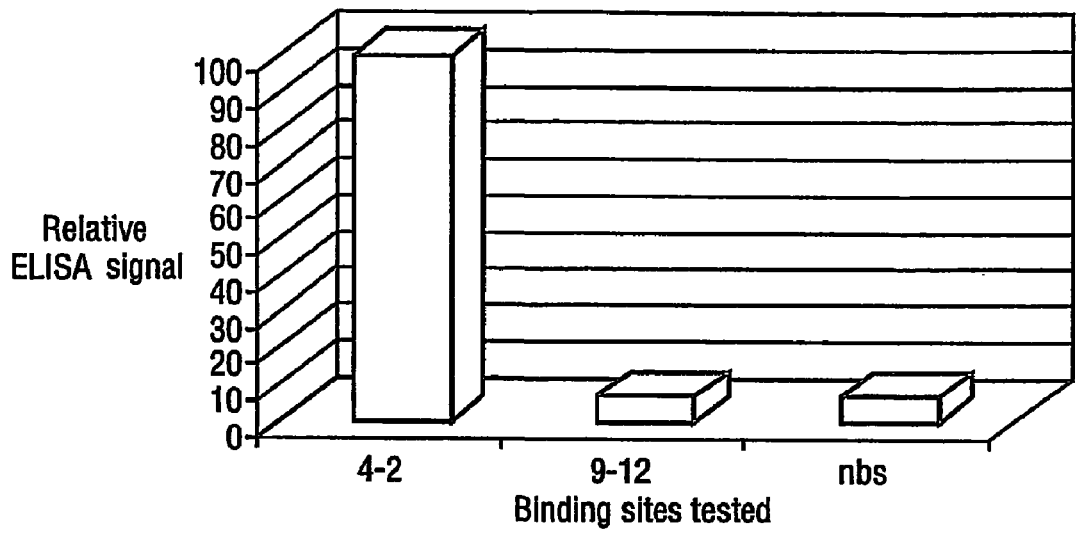
FIGS. 3A, 3B and 3C show binding by the TNF six-zinc finger peptides using an in vitro (TNT) fluorescence ELISA assay.
Figure 3B:
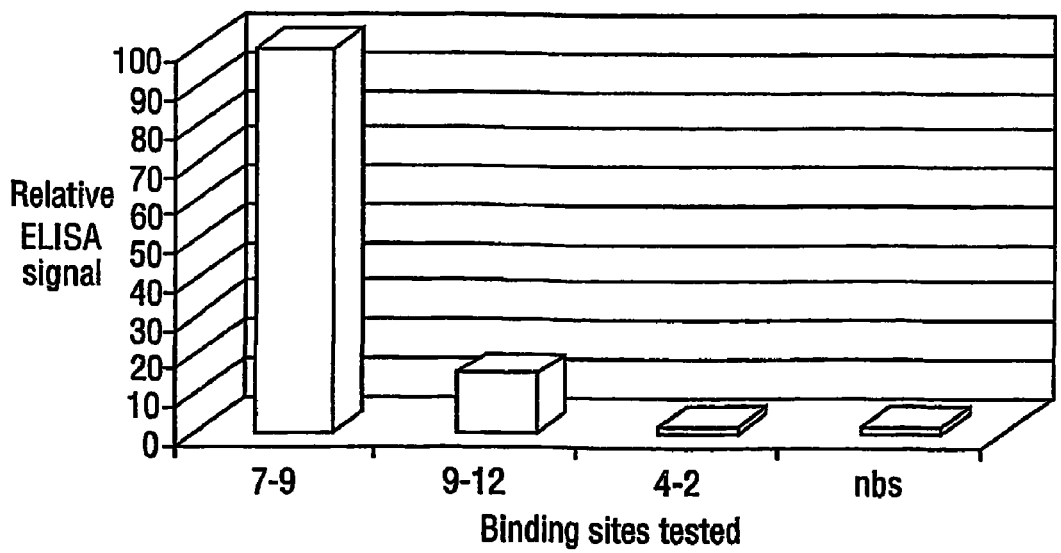
Figure 3C:
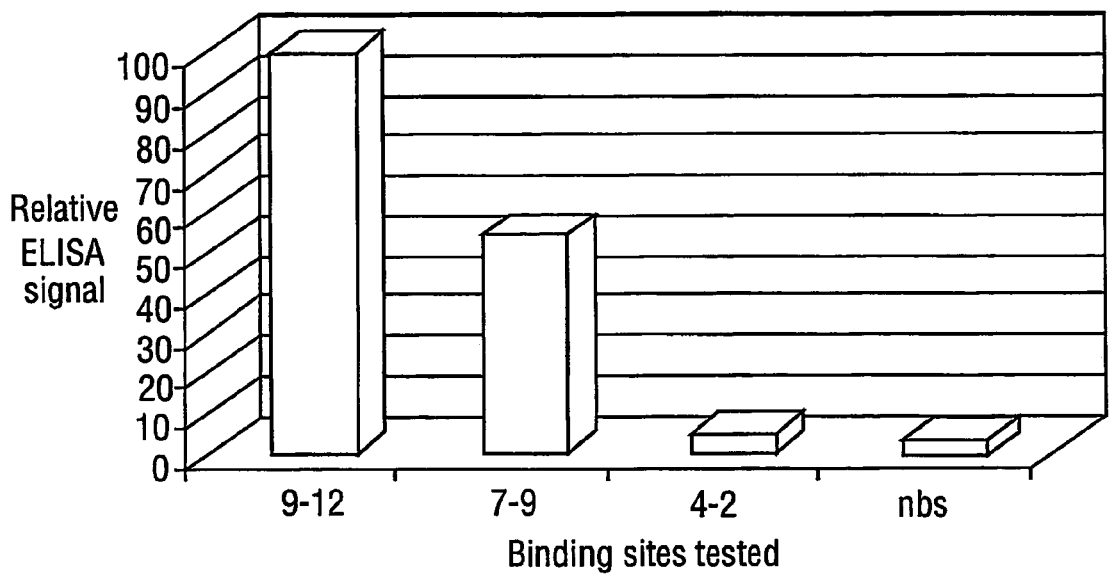

FIG. 3A shows binding of the six-zinc finger peptide, TNFR1-4-2, to its preferred target site and to a control site from elsewhere in the TNFR1 promoter (9-12). FIG. 3B shows binding of the six-zinc finger peptide, TNFR1-7-9, to its preferred target site, an overlapping site (9-12), and to a control site from elsewhere in the TNFR1 promoter (4-2). FIG. 3C shows binding of the six-zinc finger peptide, TNFR1-9-12, to its preferred target site, an overlapping site (7-9), and to a control site from elsewhere in the TNFR1 promoter (4-2).

The above assays reveal that the proteins bind specifically to their respective target sequences.

Example 9

Specific Down-Regulation of Endogenous TNFR1 by Selected Zinc Finger Proteins (FACS Analysis)

Figure 4A:
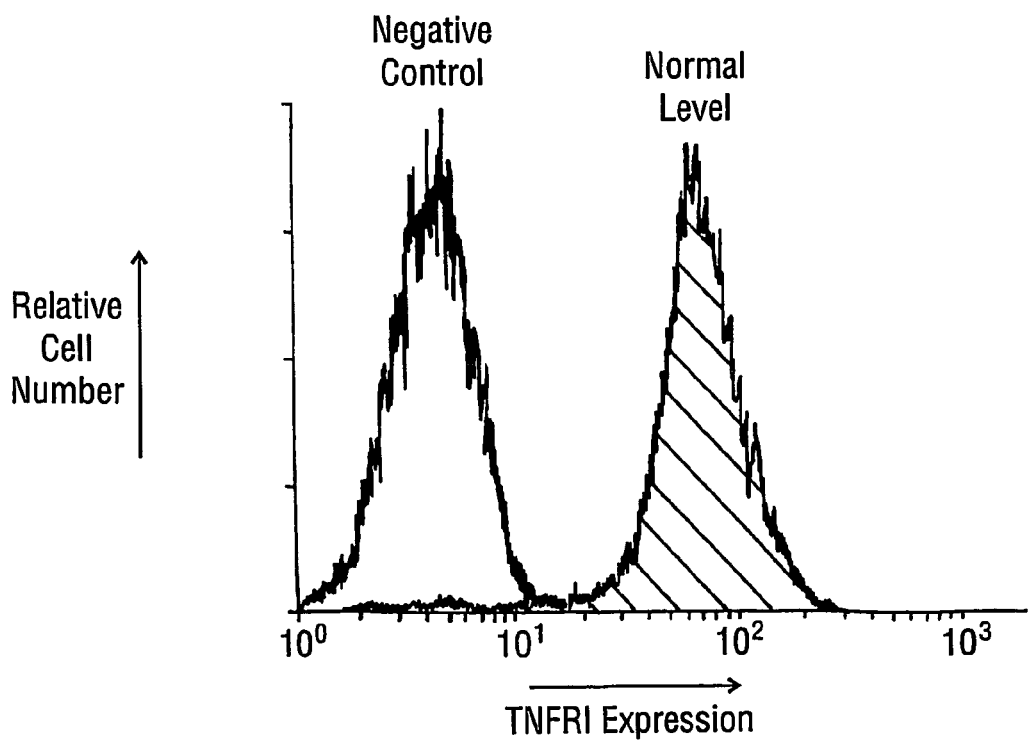
FIGS. 4A and 4B show specific down-regulation of endogenous TNFR1 expression by four distinct zinc finger proteins, as assayed by FACS analysis.

The Jurkat T-cell line is used in a transient transfection assay to validate the selected zinc finger constructs. Expression of TNFR1 at the surface of unmanipulated Jurkat cells is measured by FACS analysis as described in Example 7, and the results are as shown in FIGS. 4A and 4B.

Figure 4B:
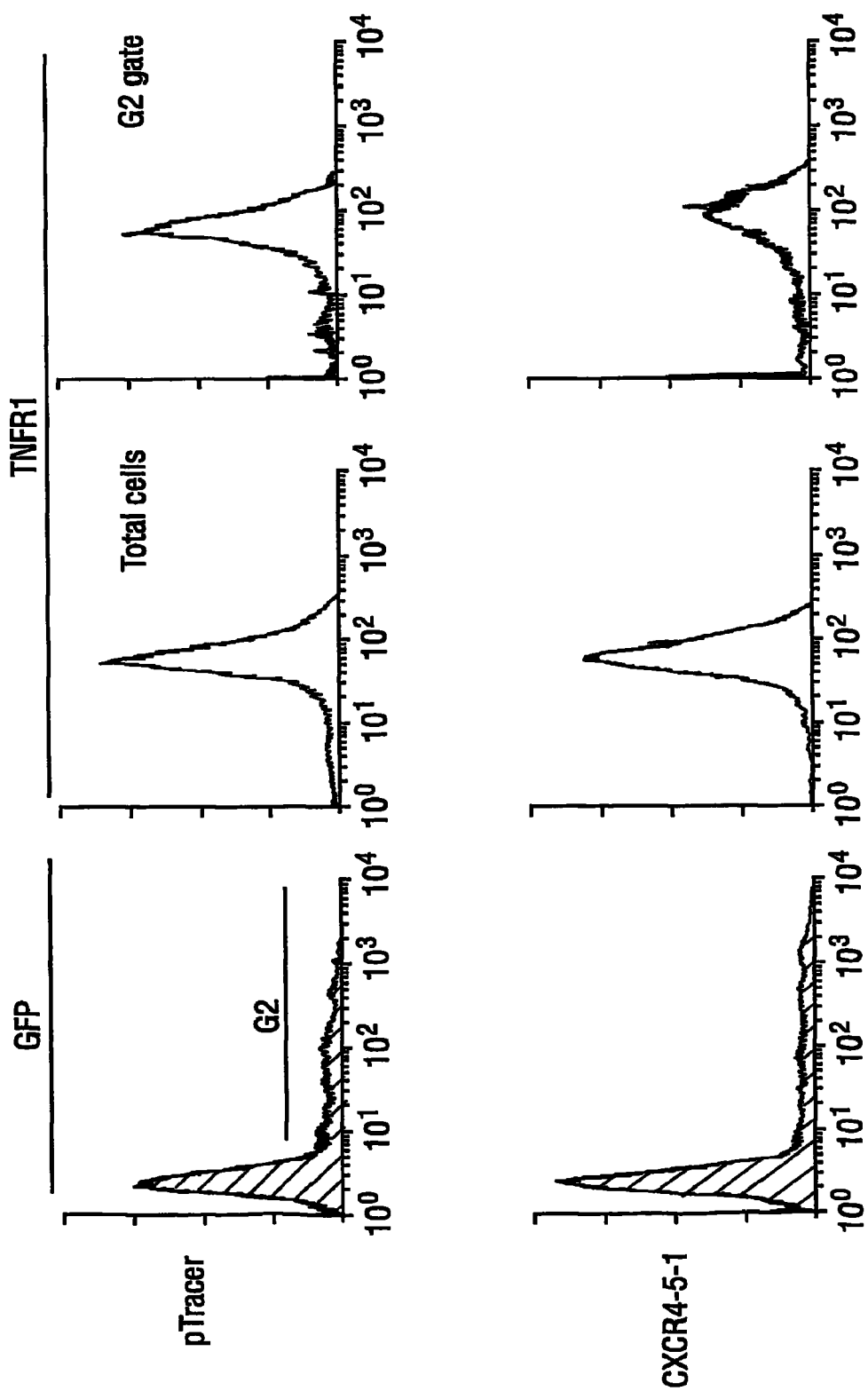

FIG. 4 shows the results of experiments in which Jurkat T-cells are transfected by electroporation with pTracerTM-CMV/Bsd zinc finger-expressing plasmids. An empty pTracer plasmid is used as a general control, and the CXCR4-5-1 zinc finger expression vector described above is used as a control to demonstrate specificity of the zinc fingers. Analysis is performed 40 hours post-electroporation, and GFP expression is used to identify the transfected cells (left column, normally 20-30% of the population). As seen in FIG. 4B (middle column), transfection with each of the TNFR1-specific zinc fingers, but not the pTracer and CXCR4-5-1 control vectors, produces a population of cells that has lost expression of TNFR1. Electronic gating on the GFP+ cells (right column) demonstrates that the TNFR1-negative population corresponds to the cells that have been transfected with the expression vector. TNFR1 expression in GFP+ cells transfected with the pTracer or CXCR4-5-1 vectors is normal.

Example 10

Specific Downregulation of a Reporter Gene Under Control of the TNFR1 Promoter by Selected Zinc Finger Proteins The region upstream of the TNFR1 gene from −163 to −790 (25) is obtained by standard PCR amplification of normal human genomic DNA obtained from peripheral blood. A proof-reading polymerase system is used (High Fidelity, Roche) and the recombinant product is sequenced after cloning into the reporter vector to confirm that the orientation is correct and that the product conformed to published TNFR1 sequences. The control reporter vector used is pMet-CAT (26), with a basal metallothionein promoter upstream of the CAT (chloramphenicol acetyl transferase) gene. This promoter is removed by HinDIII digestion and replaced with the TNFR1 PCR product for the specific reporter.

Figure 5:
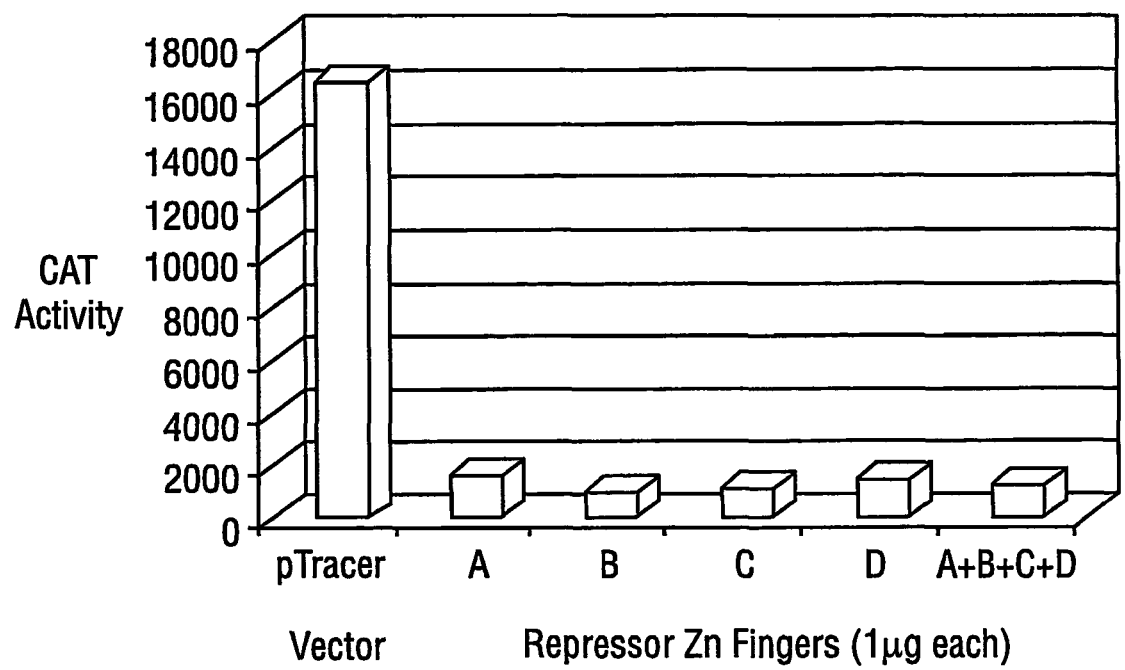
FIG. 5 shows down-regulation of expression from a TNFR promoter as assayed by a CAT assay. The figure demonstrates down-regulation with TNFR1-4-2 (A), TNFR1-9-12 (B), TNFR1-7-9 (C), TNFR1-7-10 (D), as well as a combination of all four of these (A+B+C+D). No down-regulation is seen with a pTracer only control.

Jurkat T cells are used for the reporter gene analysis, using the transfection conditions described above. 15 μg of the CAT reporter is mixed with 3 μg of pTracer, or 1 μg of the zinc finger expression vectors plus 2 μg of pTracer. Cells are harvested 22 hours after electroporation and CAT activities are measured with a radioactive assay (QuanT-CAT, Amersham). As shown in FIG. 5 all four zinc fingers directed at the TNFR1 sequence substantially reduced promoter activity, and the level of repressed activity is below that generated from the metallothionein minimal promoter. Inclusion of all four zinc finger vectors did not further repress activity, but this is most likely due to the complete repression by constructs rather than by the lack of additive or cooperative repression by multiple finger zinc finger proteins directed at distinct sites associated with the gene.

Example 11

Down-Regulation of CXCR4 and TNFR-1 in the Same Cell

Jurkat T cells are grown according to supplier instructions in RPMI 1640 L-glutamine containing medium (Life Technology) supplemented with penicillin/streptomycin and fetal calf serum $5 \times 10^6$ cells in 0.2 ml of culture medium are transfected in a 0.4 cm gap electroporation cuvette at 0.20 kV and 960 μF with a total of 20 μg plasmid DNA, comprising 15 μg of a 'carrier' plasmid, such as pBluescript (Stratagene), or equivalent, and 5 μg of the appropriate test expression vector.

pTracerTM-CMV/Bsd zinc finger expressing plasmid. An empty pTracerTM-CMV/Bsd vector plasmid is used as control. The electroporated samples are transferred to 25 cm² cell culture flask containing 10 ml Jurkat T cell growth media and incubated for 24 to 72 hours at 37° C. and 5% $CO_2$.
Duplicate wells are transfected with:
A. 5 µg empty pTracerTM-CMV/Bsd plasmid as a control
B. 2.5 µg TNFR1-4-2-Kox expressing pTracer plus 2.5 µg empty pTracer
C. 2.5 µg CXCR4-5-1-Kox expressing pTracer plus 2.5 µg empty pTracer
D. 2.5 µg TNFR1-4-2-Kox expressing pTracer plus 2.5 µg CXCR4-5-1-Kox expressing pTracer Cells are harvested and pelleted at 1000 rpm for 5 minutes at room temperature in a desk-top centrifuge. Pellets are resuspended in ice-cold 50 µl staining buffer (PBS, 0.5% BSA, 0.01% sodium azide) and incubated for 30 minutes on ice with saturating amounts of antibodies.

To assess for CXCR4 expression, cells are stained with biotinylated mouse-anti-human CXCR4 antibody (clone 44716.111 or clone 44717.111, R&Dsystem, diluted 1:10 in staining buffer) which is detected with streptavidin-PE (R&Dsystem, diluted 1:20 in staining buffer).

To assess for TNFR-1 expression, cells are stained with a mouse-anti-human TNFR1 antibody (550514, Pharmingen, 1:25 dilution), which is then bound by a biotinylated anti-mouse IgG, Fab-specific (1:100 dilution, Sigma), and detected with streptavidin-Cychrome (1:200 dilution, Pharmingen).

To assess for ICAM expression, cells are stained with a mouse-anti-human ICAM antibody (MCA532, Serotec, 1:25 dilution), which is then bound by a biotinylated anti-mouse IgG, Fab-specific (1:100 dilution, Sigma), and detected with streptavidin-Cychrome (1:200 dilution, Pharmingen).

Between each step, cells are pelleted at 1000 rpm for 5 minutes and washed twice in 150 µl ice-cold staining buffer. Flow cytometric analysis is performed on a FACSCalibur using the CellQuest software package (Becton Dickinson). About 300, 000 events corresponding to 15,000 events gated on GFP positive cells are collected per sample.

FIG. 6 shows the results of the experiment described above. The first column shows the total cell population, analysed according to GFP expression (dark filled area), with the population of cells expressing GFP (and therefore containing the zinc finger construct) indicated by a horizontal line. Columns 2, 3 and 4 show the expression levels of TNFR-1, CXCR4 and ICAM (a non-target cell-surface protein, which acts as a control), respectively, in the cell populations which express GFP. The graphs further show that cells expressing only the TNFR1-4-2-Kox peptide have greatly reduced expression of TNFR-1 while having normal levels of CXCR4 and ICAM. Cells expressing only the CXCR4-5-1-Kox protein display greatly reduced levels of CXCR4 and unaltered levels of TNFR-1 and ICAM. More importantly, cells expressing both the CXCR4 and TNFR-1 inhibitory proteins display greatly reduced expression of both CXCR4 and TNFR-1, but do not show a change in the level of the control protein, ICAM.

The above experiments show that zinc finger polypeptides engineered against receptor nucleotide sequences are capable of down-regulating expression of receptor polypeptides, in their native environment, as well as assayed by reporter systems.

REFERENCES

1. Berger, E. a.; Doms, R. W.; Fenyo, E. M.; Korber, B. T.; Littman, D. R.; Moore, J. P.; Sattentau, Q. J.; Schuitemaker, H.; Sodroski, J.; Weiss, R. a., a New Classification for Hiv-1. Nature 391(6664):240 (1998).
2. Bleul, C. C.; Farzan, M.; Choe, H.; Parolin, C.; Clark-Lewis, I.; Sodroski, J.; Springer, T. a., the Lymphocyte Chemoattractant Sdf-1 is a Ligand for Lestr/Fusin and Blocks Hiv-1 Entry. Nature 382(6594):829-833 (1996).
3. Bleul, C. C.; Wu, L.; Hoxie, J. a.; Springer, T. a.; Mackay, C. R., the Hiv Coreceptors Cxcr4 and Ccr5 Are Differentially Expressed and Regulated On Human T Lymphocytes. Proc Natl Acad Sci Usa 94(5):1925-1930 (1997).
4. Brelot, a.; Heveker, N.; Pleskoff, O.; Sol, N.; Alizon, M., Role of the First and Third Extracellular Domains of Cxcr-4 in Human Immunodeficiency Virus Coreceptor Activity. J Virol 71(6):4744-4751 (1997).
5. Di Marzio, P.; Tse, J.; Landau, N. R., Chemokine Receptor Regulation and Hiv Type 1 Tropism in Monocyte-Macrophages. Aids Res Hum Retroviruses 14(2):129-138 (1998).
6. D'souza, M. P.; Harden, V. a., Chemokines and Hiv-1 Second Receptors. Nature Medicine 2:1293-1300 (1996).
7. Feng, Y.; Broder, C. C.; Kennedy P. E.; Berger E. a., Hiv-1 Entry Cofactor: Functional C-Dna Cloning of a Seven-Transmembrane, G Protein-Coupled Receptor. Science 272:872-877 (1996).
8. Forster, R.; Kremmer, E.; Schubel, a.; Breitfeld, D.; Kleinschmidt, a; Nerl, C.; Bernhardt, G.; Lipp, M.; Intracellular and Surface Expression of the Hiv-1 Coreceptor Cxcr4/Fusin On Various Leukocyte Subsets: Rapid Internalization and Recycling Upon Activation. J Immunol 160(3): 1522-1531 (1998).
9. Granelli-Piperno, a.; Moser, B.; Pope, M.; Chen, D.; Wei, Y.; Isdell, F.; O'doherty, U.; Paxton, W.; Koup, R.; Mojsov, S.; Bhardwaj, N.; Clark-Lewis, I.; Baggiolini, M.; Steinman, R. M.; Efficient Interaction of Hiv-1 with Purified Dendritic Cells Via Multiple Chemokine Coreceptors. J Exp Med 184(6):2433-2438 (1996).
10. Gupta, S. K.; Lysko, P. G.; Pillarisetti, K.; Ohlstein, E.; Stadel, J. M.; Chemokine Receptors in Human Endothelial Cells—Functional Expression of Cxcr4 and Its Transcriptional Regulation By Inflammatory Cytokines. J Biol Chem 273(7):4282-4287 (1998).
11. Lavi, E.; Strizki, J. M.; Ulrich, a. M.; Zhang, W.; Fu, L.; Wang, Q.; O'connor, M.; Hoxie, J. a.; Gonzalez-Scarano, F.; Cxcr-4 (Fusin), a Co-Receptor for the Type 1 Human Immunodeficiency Virus (Hiv-1), is Expressed in the Human Brain in a Variety of Cell Types, Including Microglia and Neurons. Am J Pathol 151(4):1035-1042 (1997).
12. Lu, Z. H.; Berson, J. F.; Chen, Y. H.; Turner, J. D.; Zhang, T. Y.; Sharron, M.; Jenks, M. H.; Wang, Z. X.; Kim, J.; Rucker, J.; Hoxie, J. a.; Peiper, S. C.; Doms, R. W., Evolution of Hiv-1 Coreceptor Usage Through Interactions with Distinct Ccr5 and Cxcr4 Domains. Proc Natl Acad Sci Usa 94(12):6426-6431 (1997).
13. Oberlin, E.; Amara, a.; Bachelerie, F.; Bessia, C.; Virelizier, J.-L.; Arenzana-Seisdedos, F.; Schwartz, O.; Heard, J.-M.; Clark-Lewis, I.; Legler, D. F.; Loetscher, M.; Baggiolini, M.; Moser, B., the Cxc Chemokine Sdf-1 is the Ligand for Lestr/Fusin and Prevents Infection By T-Cell-Line-Adapted Hiv-1. Nature 382(6594):833-835 (1996).
14. Signoret, N.; Oldridge, J.; Pelchen-Matthews, a.; Klasse, P. J.; Tran, T.; Brass, L. F.; Rosenkilde, M. M.; Schwartz, T. W.; Holmes, W.; Dallas, W.; Luther, M. a.; Wells, T. N. C.; Hoxie, J. a.; Marsh, M., Phorbol Esters and Sdf-1 Induce Rapid Endocytosis and Down Modulation of the Chemokine Receptor Cxcr4. J Cell Biol 139(3):651-664 (1997).

15. Volin, M. V.; Joseph, E.; Shockley, M. S.; Davies, P. F., Chemokine Receptor Cxcr4 Expression in Endothelium. Biochem Biophys Res Commun 242(1):46-53 (1998).
16. Yi, Y. J.; Rana, S.; Turner, J. D.; Gaddis, N.; Collman, R. G., Cxcr-4 is Expressed By Primary Macrophages and Supports Ccr5-Independent Infection By Dual-Tropic But Not T-Tropic Isolates of Human Immunodeficiency Virus Type 1. J Virol 72(1):772-777 (1998).
17. Chan, F. K., Siegel, R M., Lenardo, M. J., Signaling by the TNF Receptor Superfamily and T Cell Homeostasis. Immunity 13: 419422 (2000).
18. Suvannavejh, G. C., Lee, H. O., Padilla, J., Dal Canto, M. C., Barret, T. A., Miller, S. D., Divergent roles for p55 and p75 tumour necrosis factor receptors in the pathogenesis of MOG(35-55)-induced experimental autoimmune encephalomyelitis. Cell. Immunology 205: 24-33 (2000).
19. Immunology. Eds Roitt, I., Brostoff, J., Male, D. Mosby, London, $4^{th}$ edition (1996).
20. Maini, R. N., Taylor, P. C., Paleolog, E., Charles, P., Ballara, S., Brennan, F. M., Feldmann, M., Anti-tumour necrosis factor specific antibody (infliximab) treatment provides insights into the pathophysiology of rheumatoid arthritis. Ann. Rheum. Disease 58:I56-I60 (1999).
21. Garrison, L., McDonnell, N. D., Etanercept: therapeutic use in patients with rheumatoid arthritis. Ann. Rheum. Disease 58:I65-I69 (1999).
22. Bachmaier, K., Pummerer, C., Kozieradzki, I., Pfeffer, K., Mak, T. W., Neu., N., Penninger, J. M. Low-molecular-weight tumour necrosis factor receptor p55 controls induction of autoimmune heart disease. Circulation 95: 655-661 (1997).
23. Li, Y. Y., Feng, Y. Q., Kadokami, T., Mctiernan, C. F., Draviam, R., Watkins, S. C., Feldman, A. M., Myocardial extracellular matrix remodeling in transgenic mice overexpressing tumor necrosis factor α can be modulated by anti-tumor necrosis factor α therapy. Proc. Natl. Acad. Sci. USA 97: 12746-12751 (2000).
24. Kollias, G., Douni, E., Kassiotis, G., Kontoyiannis, D., On the role of tumour necrosis factor and receptors in models of multi-organ failure, rheumatoid arthritis, multiple sclerosis and inflammatory bowel disease. Immunol. Rev. 169: 175-194 (1999).
25. Kemper, O., Wallach, D., Cloning and partial characterization of the promoter for the human p55 tumor necrosis factor (TNF) receptor. Gene 134: 209-216 (1993).
26. Luscher B, Mitchell P J, Williams T, Tjian R. Regulation of transcriptional factor AP-2 by the morphogen retinoic acid and by second messengers. Genes Dev. 3:1507-1517 (1989).

Each of the applications and patents mentioned above, and each document cited or referenced in each of the foregoing applications and patents, including during the prosecution of each of the foregoing applications and patents ("application cited documents") and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference. In particular, we hereby incorporate by reference International Patent Application Numbers PCT/GB00/02080 (WO01/00815), PCT/GB00/02071 (WO00/73434), PCT/GB00/03765 (WO01/25417), United Kingdom Patent Application Numbers GB0001582.6, GB0001578.4, and GB9912635.1 as well as US09/478,513.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

ZINC FINGER CONSENSUS SEQUENCES:

CONSENSUS SEQUENCE 1
$X_{0-2}$ C $X_{1-5}$ C $X_{2-7}$ D S A T L T E H $X_{3-6}$ H/C

CONSENSUS SEQUENCE 2
$X_{0-2}$ C $X_{1-5}$ C $X_{2-7}$ R R D D L S R H $X_{3-6}$ H/C

CONSENSUS SEQUENCE 3
$X_{0-2}$ C $X_{1-5}$ C $X_{2-7}$ R K S D R T R H $X_{3-6}$ H/C

CONSENSUS SEQUENCE 4
$X_{0-2}$ C $X_{1-5}$ C $X_{2-7}$ R S D E L T R H $X_{3-6}$ H/C

CONSENSUS SEQUENCE 5
$X_{0-2}$ C $X_{1-5}$ C $X_{2-7}$ R S D T L S K H $X_{3-6}$ H/C

CONSENSUS SEQUENCE 6
$X_{0-2}$ C $X_{1-5}$ C $X_{2-7}$ Q K H D R T Q H $X_{3-6}$ H/C

CONSENSUS SEQUENCE 7
$X_{0-2}$ C $X_{1-5}$ C $X_{2-7}$ K S N D L I R H $X_{3-6}$ H/C

CONSENSUS SEQUENCE 8
$X_{0-2}$ C $X_{1-5}$ C $X_{2-7}$ Q S A H L S R H $X_{3-6}$ H/C

CONSENSUS SEQUENCE 9
$X_{0-2}$ C $X_{1-5}$ C $X_{2-7}$ D N R D R T K H $X_{3-6}$ H/C

CONSENSUS SEQUENCE 10
$X_{0-2}$ C $X_{1-5}$ C $X_{2-7}$ R S D E L T R H $X_{3-6}$ H/C

CONSENSUS SEQUENCE 11
$X_{0-2}$ C $X_{1-5}$ C $X_{2-7}$ R S D T L S K H $X_{3-6}$ H/C

CONSENSUS SEQUENCE 12
$X_{0-2}$ C $X_{1-5}$ C $X_{2-7}$ Q K H D R T Q H $X_{3-6}$ H/C

CONSENSUS SEQUENCE 13
$X_{0-2}$ C $X_{1-5}$ C $X_{2-7}$ K S N D L I R H $X_{3-6}$ H/C

CONSENSUS SEQUENCE 14
$X_{0-2}$ C $X_{1-5}$ C $X_{2-7}$ Q S A H L S R H $X_{3-6}$ H/C

CONSENSUS SEQUENCE 15
$X_{0-2}$ C $X_{1-5}$ C $X_{2-7}$ D N R D R T K H $X_{3-6}$ H/C

CONSENSUS SEQUENCE 16
$X_{0-2}$ C $X_{1-5}$ C $X_{2-7}$ R S T D L I R H $X_{3-6}$ H/C

CONSENSUS SEQUENCE 17
$X_{0-2}$ C $X_{1-5}$ C $X_{2-7}$ T S S N L S A H $X_{3-6}$ H/C

CONSENSUS SEQUENCE 18
$X_{0-2}$ C $X_{1-5}$ C $X_{2-7}$ R N A D R T K H $X_{3-6}$ H/C

CONSENSUS SEQUENCE 19
$X_{0-2}$ C $X_{1-5}$ C $X_{2-7}$ A S A D L T R H $X_{3-6}$ H/C

CONSENSUS SEQUENCE 20
$X_{0-2}$ C $X_{1-5}$ C $X_{2-7}$ R R D H L S E H $X_{3-6}$ H/C

CONSENSUS SEQUENCE 21
$X_{0-2}$ C $X_{1-5}$ C $X_{2-7}$ R N D S R T N H $X_{3-6}$ H/C

TABLE 1-continued

ZINC FINGER CONSENSUS SEQUENCES:

CONSENSUS SEQUENCE 22
$X_{0-2}$ C $X_{1-5}$ C $X_{2-7}$ R S Q H L T E H $X_{3-6}$ H/C

CONSENSUS SEQUENCE 23
$X_{0-2}$ C $X_{1-5}$ C $X_{2-7}$ T S S H L S V H $X_{3-6}$ H/C

CONSENSUS SEQUENCE 24
$X_{0-2}$ C $X_{1-5}$ C $X_{2-7}$ H S N A R K T H $X_{3-6}$ H/C

CONSENSUS SEQUENCE 25
$X_{0-2}$ C $X_{1-5}$ C $X_{2-7}$ R S D E L T R H $X_{3-6}$ H/C

CONSENSUS SEQUENCE 26
$X_{0-2}$ C $X_{1-5}$ C $X_{2-7}$ R S D N L S E H $X_{3-6}$ H/C

CONSENSUS SEQUENCE 27
$X_{0-2}$ C $X_{1-5}$ C $X_{2-7}$ R S D N R K T H $X_{3-6}$ H/C

CONSENSUS SEQUENCE 28
$X_{0-2}$ C $X_{1-5}$ C $X_{2-7}$ D N R D L I R H $X_{3-6}$ H/C

CONSENSUS SEQUENCE 29
$X_{0-2}$ C $X_{1-5}$ C $X_{2-7}$ R S D D L S R H $X_{3-6}$ H/C

CONSENSUS SEQUENCE 30
$X_{0-2}$ C $X_{1-5}$ C $X_{2-7}$ R S D N R T K H $X_{3-6}$ H/C

CONSENSUS SEQUENCE 31
$X_{0-2}$ C $X_{1-5}$ C $X_{2-7}$ D N R D L I R H $X_{3-6}$ H/C

CONSENSUS SEQUENCE 32
$X_{0-2}$ C $X_{1-5}$ C $X_{2-7}$ R S D D L S R H $X_{3-6}$ H/C

CONSENSUS SEQUENCE 33
$X_{0-2}$ C $X_{1-5}$ C $X_{2-7}$ R S D N R T K H $X_{3-6}$ H/C

CONSENSUS SEQUENCE 34
$X_{0-2}$ C $X_{1-5}$ C $X_{2-7}$ D S A H L I R H $X_{3-6}$ H/C

CONSENSUS SEQUENCE 35
$X_{0-2}$ C $X_{1-5}$ C $X_{2-7}$ T S S D L S R H $X_{3-6}$ H/C

CONSENSUS SEQUENCE 36
$X_{0-2}$ C $X_{1-5}$ C $X_{2-7}$ Q S A H R K T H $X_{3-6}$ H/C

ADDITIONAL ZINC FINGER CONSENSUS SEQUENCES:
$X^a$ C $X_{2-4}$ C $X_{2-3}$ F $X^C$ D S A T L T E H X X $X^b$ H

$X^a$ C $X_{2-4}$ C $X_{2-3}$ F $X^C$ R R D D L S R H X X $X^b$ H

$X^a$ C $X_{2-4}$ C $X_{2-3}$ F $X^C$ R K S D R T R H X X $X^b$ H

$X^a$ C $X_{2-4}$ C $X_{2-3}$ F $X^C$ R S D E L T R H X X $X^b$ H

$X^a$ C $X_{2-4}$ C $X_{2-3}$ F $X^C$ R S D T L S K H X X $X^b$ H

$X^a$ C $X_{2-4}$ C $X_{2-3}$ F $X^C$ Q K H D R T Q H X X $X^b$ H

$X^a$ C $X_{2-4}$ C $X_{2-3}$ F $X^C$ K S N D L I R H X X $X^b$ H

$X^a$ C $X_{2-4}$ C $X_{2-3}$ F $X^C$ Q S A H L S R H X X $X^b$ H

$X^a$ C $X_{2-4}$ C $X_{2-3}$ F $X^C$ D N R D R T K H X X $X^b$ H

$X^a$ C $X_{2-4}$ C $X_{2-3}$ F $X^C$ R S D E L T R H X X $X^b$ H

$X^a$ C $X_{2-4}$ C $X_{2-3}$ F $X^C$ R S D T L S K H X X $X^b$ H

$X^a$ C $X_{2-4}$ C $X_{2-3}$ F $X^C$ Q K H D R T Q H X X $X^b$ H

$X^a$ C $X_{2-4}$ C $X_{2-3}$ F $X^C$ K S N D L I R H X X $X^b$ H

$X^a$ C $X_{2-4}$ C $X_{2-3}$ F $X^C$ Q S A H L S R H X X $X^b$ H

$X^a$ C $X_{2-4}$ C $X_{2-3}$ F $X^C$ D N R D R T K H X X $X^b$ H

$X^a$ C $X_{2-4}$ C $X_{2-3}$ F $X^C$ R S T D L I R H X X $X^b$ H

$X^a$ C $X_{2-4}$ C $X_{2-3}$ F $X^C$ T S S N L S A H X X $X^b$ H

$X^a$ C $X_{2-4}$ C $X_{2-3}$ F $X^C$ R N A D R T K H X X $X^b$ H

$X^a$ C $X_{2-4}$ C $X_{2-3}$ F $X^C$ A S A D L T R H X X $X^b$ H

$X^a$ C $X_{2-4}$ C $X_{2-3}$ F $X^C$ R R D H L S E H X X $X^b$ H

$X^a$ C $X_{2-4}$ C $X_{2-3}$ F $X^C$ R N D S R T N H X X $X^b$ H

$X^a$ C $X_{2-4}$ C $X_{2-3}$ F $X^C$ R S Q H L T E H X X $X^b$ H

$X^a$ C $X_{2-4}$ C $X_{2-3}$ F $X^C$ T S S H L S V H X X $X^b$ H

$X^a$ C $X_{2-4}$ C $X_{2-3}$ F $X^C$ H S N A R K T H X X $X^b$ H

$X^a$ C $X_{2-4}$ C $X_{2-3}$ F $X^C$ R S D E L T R H X X $X^b$ H

$X^a$ C $X_{2-4}$ C $X_{2-3}$ F $X^C$ R S D N L S E H X X $X^b$ H

$X^a$ C $X_{2-4}$ C $X_{2-3}$ F $X^C$ R S D N R K T H X X $X^b$ H

$X^a$ C $X_{2-4}$ C $X_{2-3}$ F $X^C$ D N R D L I R H X X $X^b$ H

$X^a$ C $X_{2-4}$ C $X_{2-3}$ F $X^C$ R S D D L S R H X X $X^b$ H

$X^a$ C $X_{2-4}$ C $X_{2-3}$ F $X^C$ R S D N R T K H X X $X^b$ H

$X^a$ C $X_{2-4}$ C $X_{2-3}$ F $X^C$ D N R D L I R H X X $X^b$ H

$X^a$ C $X_{2-4}$ C $X_{2-3}$ F $X^C$ R S D D L S R H X X $X^b$ H

$X^a$ C $X_{2-4}$ C $X_{2-3}$ F $X^C$ R S D N R T K H X X $X^b$ H

$X^a$ C $X_{2-4}$ C $X_{2-3}$ F $X^C$ D S A H L I R H X X $X^b$ H

$X^a$ C $X_{2-4}$ C $X_{2-3}$ F $X^C$ T S S D L S R H X X $X^b$ H

$X^a$ C $X_{2-4}$ C $X_{2-3}$ F $X^C$ Q S A H R K T H X X $X^b$ H

The invention claimed is:

1. A method of down-regulating expression of a CXCR4 receptor in an isolated cell, the method comprising the step of:
Expressing, in the isolated cell, a fusion protein comprising a repression domain and at least one engineered zinc finger protein comprising 3 zinc fingers, wherein the zinc finger protein binds to a target site in the non-coding region of a CXCR4 gene, the target site comprising the sequence GNN and further wherein the fusion protein down-regulates expression of the CXCR4 receptor.

2. The method of claim 1, wherein the zinc finger protein comprises 6 zinc fingers.

* * * * *